US011872034B2

(12) United States Patent
Escobar et al.

(10) Patent No.: US 11,872,034 B2
(45) Date of Patent: Jan. 16, 2024

(54) MACHINE LEARNING IN AN ARTIFICIAL PANCREAS

(71) Applicant: DexCom, Inc., San Diego, CA (US)

(72) Inventors: Derek James Escobar, Escondido, CA (US); Naresh C. Bhavaraju, San Diego, CA (US); Gary A. Morris, La Jolla, CA (US); Jorge Valdes, San Diego, CA (US)

(73) Assignee: DEXCOM, INC., San Diego, CA (US)

( * ) Notice: Subject to any disclaimer, the term of this patent is extended or adjusted under 35 U.S.C. 154(b) by 458 days.

(21) Appl. No.: 17/114,190

(22) Filed: Dec. 7, 2020

(65) Prior Publication Data

US 2021/0260288 A1 Aug. 26, 2021

Related U.S. Application Data

(60) Provisional application No. 62/979,347, filed on Feb. 20, 2020.

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0004* (2013.01); *A61B 5/425* (2013.01);
(Continued)

(58) Field of Classification Search
None
See application file for complete search history.

(56) References Cited

U.S. PATENT DOCUMENTS

2008/0206799 A1  8/2008  Blomquist
2011/0124996 A1  5/2011  Reinke et al.
(Continued)

OTHER PUBLICATIONS

International Search Report and Written Opinion dated Apr. 6, 2021 for Application No. PCT/US2020/063652, filed Dec. 7, 2020; 12 pages.
(Continued)

*Primary Examiner* — Manuel A Mendez
(74) *Attorney, Agent, or Firm* — Stuart H. Mayer; Kaplan Breyer Schwarz LLP

(57) ABSTRACT

Machine learning in an artificial pancreas is described. An artificial pancreas system may include a wearable glucose monitoring device, an insulin delivery system, and a computing device. Broadly speaking, the wearable glucose monitoring device provides glucose measurements of a person continuously. The artificial pancreas algorithm, which may be implemented at the computing device, determines doses of insulin to deliver to the person based on a variety of aspects for the purpose of maintaining the person's glucose within a target range, as indicated by those glucose measurements. The insulin delivery system then delivers those determined doses to the person. As the artificial pancreas algorithm determines insulin doses for the person over time and effectiveness of the insulin doses to maintain the person's glucose level in the target range is observed, an underlying model of the artificial pancreas algorithm may be updated to better determine insulin doses.

25 Claims, 19 Drawing Sheets

(51) Int. Cl.
<table>
<tr><td>A61M 5/172</td><td>(2006.01)</td></tr>
<tr><td>A61M 5/142</td><td>(2006.01)</td></tr>
<tr><td>G16H 20/17</td><td>(2018.01)</td></tr>
<tr><td>G16H 40/67</td><td>(2018.01)</td></tr>
<tr><td>G06N 20/00</td><td>(2019.01)</td></tr>
<tr><td>H04W 12/037</td><td>(2021.01)</td></tr>
<tr><td>H04L 9/30</td><td>(2006.01)</td></tr>
<tr><td>G06N 20/20</td><td>(2019.01)</td></tr>
<tr><td>G16H 10/60</td><td>(2018.01)</td></tr>
<tr><td>G16H 50/30</td><td>(2018.01)</td></tr>
<tr><td>G16H 50/20</td><td>(2018.01)</td></tr>
<tr><td>H04W 12/033</td><td>(2021.01)</td></tr>
</table>

(52) U.S. Cl.
CPC ............ *A61B 5/6801* (2013.01); *A61B 5/743* (2013.01); *A61B 5/7475* (2013.01); *A61M 5/14244* (2013.01); *A61M 5/1723* (2013.01); *G06N 20/00* (2019.01); *G06N 20/20* (2019.01); *G16H 10/60* (2018.01); *G16H 20/17* (2018.01); *G16H 40/67* (2018.01); *G16H 50/20* (2018.01); *G16H 50/30* (2018.01); *H04L 9/30* (2013.01); *H04W 12/033* (2021.01); *H04W 12/037* (2021.01); *A61M 2205/18* (2013.01); *A61M 2205/3553* (2013.01); *A61M 2205/3584* (2013.01); *A61M 2205/3592* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/8206* (2013.01); *A61M 2230/201* (2013.01)

(56) References Cited

U.S. PATENT DOCUMENTS

<table>
<tr><td>2015/0207626 A1*</td><td>7/2015</td><td>Neftel ................... G16H 40/67<br>713/168</td></tr>
<tr><td>2016/0038673 A1*</td><td>2/2016</td><td>Morales ................ G16H 50/50<br>700/282</td></tr>
<tr><td>2016/0038675 A1*</td><td>2/2016</td><td>Estes ................... A61M 5/1723<br>604/151</td></tr>
<tr><td>2017/0173261 A1</td><td>6/2017</td><td>O'Connor et al.</td></tr>
<tr><td>2017/0173262 A1</td><td>6/2017</td><td>Veltz</td></tr>
<tr><td>2017/0189614 A1</td><td>7/2017</td><td>Mazlish et al.</td></tr>
<tr><td>2019/0076072 A1</td><td>3/2019</td><td>Simmons et al.</td></tr>
<tr><td>2019/0298920 A1</td><td>10/2019</td><td>Haider et al.</td></tr>
<tr><td>2019/0385752 A1</td><td>12/2019</td><td>Bowland et al.</td></tr>
<tr><td>2020/0060624 A1</td><td>2/2020</td><td>Atlas et al.</td></tr>
<tr><td>2021/0050085 A1</td><td>2/2021</td><td>Hayter et al.</td></tr>
<tr><td>2022/0257857 A1</td><td>8/2022</td><td>Dassau et al.</td></tr>
</table>

OTHER PUBLICATIONS

International Preliminary Report on Patentability for Application No. PCT/US2020/063652, dated Sep. 1, 2022, 8 pages.

* cited by examiner

1800

1802
Generate an encrypted message by encrypting an insulin delivery request, the insulin delivery request requesting delivery of insulin by an insulin delivery system to a person wearing the insulin delivery system

1804
Communicate the encrypted message to an insulin application for decryption and for further communication of instructions, based on the insulin delivery request, to the insulin delivery system

1902
Receive an encrypted message comprising an insulin delivery request

1904
Decrypt the encrypted message to reveal the insulin delivery request

1906
Communicate instructions to an insulin delivery system over a wireless connection, the instructions instructing the insulin delivery system to deliver insulin to a person wearing the insulin delivery system according to the insulin delivery request

Fig. 19

# MACHINE LEARNING IN AN ARTIFICIAL PANCREAS

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Patent Application No. 62/979,347, filed Feb. 20, 2020, and titled "Machine Learning in An Artificial Pancreas". The aforementioned application is incorporated by reference herein in its entirety, and is hereby expressly made a part of this specification.

BACKGROUND

Diabetes is a metabolic condition affecting hundreds of millions of people, and is one of the leading causes of death worldwide. For people living with diabetes, access to treatment is critical to their survival. With proper treatment, serious damage to the heart, blood vessels, eyes, kidneys, and nerves, due to diabetes can be largely avoided. Proper treatment for a person with Type I diabetes generally involves monitoring glucose levels throughout the day and regulating those levels—oftentimes using insulin—so that the levels stay within a target range. Insulin therapy may also be prescribed for many with Type II diabetes as part of their treatment.

Developing an insulin therapy plan and then administering it typically requires oversight of a health care provider, at least initially and at regular intervals, e.g., to ensure proper bodily responses to and effectiveness of the therapy. Conventional insulin therapy techniques also generally involve rigor on the part of the person undergoing the therapy. In order to determine a basal rate of insulin, for example, a person may need to follow an incremental process of delivering insulin at a particular rate (initially low), observing how his or her glucose measurements are affected at the particular rate, and then, until the person's glucose measurements remain in a target range consistently, manually adjusting the rate on his or her insulin pump a small amount upward at each increment by referencing generic adjustment tables. This process can take months, however, and thus be cumbersome for the person. Determining bolus insulin doses can also be arduous—doing so may involve observing the person's glucose several times after eating a same, measured amount of a particular carbohydrate (e.g., white rice separately from brown rice) or after eating a same meal (in terms of food and its amount) and also involve delivering a measured amount of bolus insulin, which the person may also need to adjust manually depending on the observed glucose.

Even after determining basal rates and bolus doses, the person must remain vigilant to ensure timely delivery of insulin according to those doses and, further, must continue to monitor his or her body's ongoing response, i.e., in case further adjustments to the doses are needed. Some examples of factors for which those doses may be further adjusted include dietary changes, weight loss, changes in exercise routine, and various medical conditions (e.g., pregnancy), to name just a few. Although insulin therapy can mean the difference between relatively normal occurrence of negative health events (experienced by most persons) and very serious ones (due specifically to diabetes), the process of customizing the therapy and then administering it can nevertheless be a burden. In addition and because of this burden, many persons who should receive insulin therapy avoid it while others neglect to adequately adhere to the parameters of their therapy.

SUMMARY

To overcome these problems, machine learning in an artificial pancreas is leveraged. In one or more implementations, an artificial pancreas system includes a wearable glucose monitoring device, an insulin delivery system, and a computing device, which are communicatively coupled to carry out various aspects of the system. Broadly speaking, the wearable glucose monitoring device provides glucose measurements of a person continuously. The artificial pancreas algorithm, which may be implemented at the computing device, determines doses of insulin to deliver to the person based on a variety of aspects and for the purpose of maintaining the person's glucose level within a target range, as indicated by those glucose measurements. The insulin delivery system then delivers the determined doses to the person for absorption by his or her body to maintain balanced glucose within the target range. As the artificial pancreas algorithm determines insulin doses for the person over time, and the effectiveness of those doses to maintain the person's glucose level is observed, e.g., based on the glucose measurements, an underlying model of the artificial pancreas algorithm may be optimized to better determine insulin doses for the person in the future.

This Summary introduces a selection of concepts in a simplified form that are further described below in the Detailed Description. As such, this Summary is not intended to identify essential features of the claimed subject matter, nor is it intended to be used as an aid in determining the scope of the claimed subject matter.

BRIEF DESCRIPTION OF THE DRAWINGS

The detailed description is described with reference to the accompanying figures.

FIG. 18 depicts a procedure in an example implementation in which an insulin delivery request is encrypted and communicated for decryption by an application.

FIG. 19 depicts a procedure in an example implementation in which an encrypted insulin delivery request is received, decrypted, and instructions for delivering insulin a communicated to an insulin delivery system based on the request.

DETAILED DESCRIPTION

Overview

Figure 1:
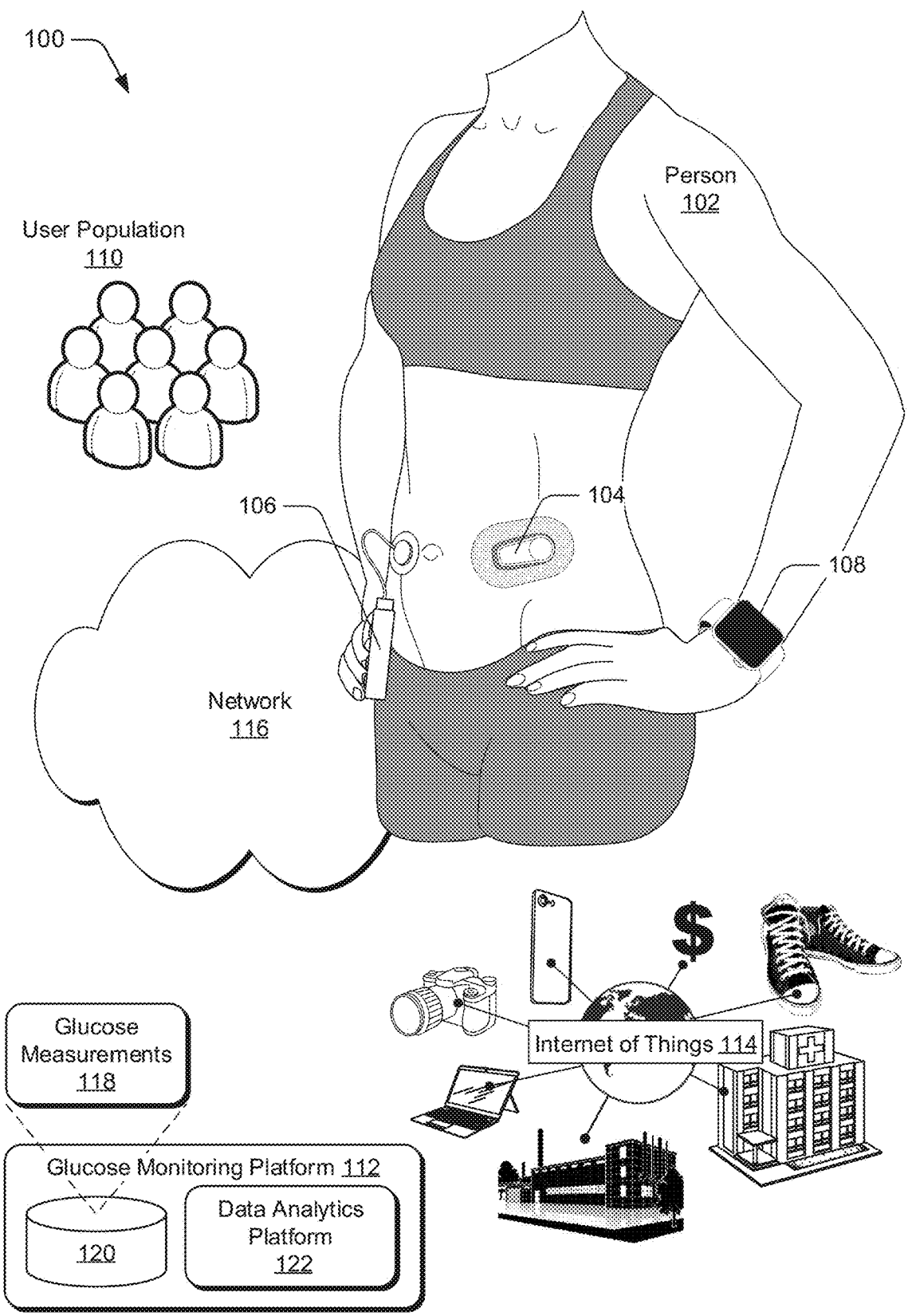
FIG. 1 is an illustration of an environment in an example implementation that is operable to employ techniques described herein.

Insulin therapy can mean the difference between relatively normal occurrence of negative health events experienced by most persons and very serious ones due specifically to diabetes. However, the process of customizing the therapy and then administering it can nevertheless be a burden. In addition and because of this burden, many persons who should receive insulin therapy avoid it while others neglect to adequately adhere to the parameters of their therapy.

Machine learning in an artificial pancreas is described herein. In one or more implementations, an artificial pancreas system includes a wearable glucose monitoring device, an insulin delivery system, and a computing device, which are communicatively coupled to carry out various aspects of the system. Broadly speaking, the wearable glucose monitoring device provides glucose measurements of a person continuously. The artificial pancreas algorithm, which may be implemented at the computing device, determines doses of insulin to deliver to the person based on a variety of aspects and for the purpose of maintaining the person's glucose level within a target range, as indicated by those glucose measurements. The insulin delivery system then delivers the determined doses to the person for absorption by his or her body to maintain balanced glucose within the target range.

As the artificial pancreas algorithm determines insulin doses for the person over time, and the effectiveness of those doses to maintain the person's glucose level is observed, e.g., based on the glucose measurements, an underlying model of the artificial pancreas algorithm may be updated to better determine insulin doses for the person in the future. By programmatically reinforcing determinations that result in stable glucose measurements within the target range and programmatically discouraging determinations that result in unstable measurements and/or measurements outside the target range, the artificial pancreas algorithm learns to more often keep the person's glucose level within the target range and/or more stable than when the algorithm is first deployed.

Using machine learning in a fully closed, automated loop between continuous glucose monitoring and delivery of determined insulin doses may remove many of the burdens of conventional systems and processes attendant to insulin therapy. For example, allowing the artificial pancreas algorithm to be adjusted automatically based on data patterns present in the continuous glucose measurements can significantly reduce a time to determine basal insulin dose rates, e.g., from nearly a year in some cases to weeks. Not only may the artificial pancreas algorithm determine and improve bolus insulin doses for a person over time based on user input of upcoming meals (e.g., grams of carbohydrates), but the artificial pancreas algorithm may also learn to predict upcoming events that may affect the person's glucose (e.g., meals and exercise) and automatically deliver insulin in anticipation of a predicted upcoming event—without receiving user input for the particular event. In addition, the artificial pancreas algorithm may learn to detect the occurrence of events as they happen that may affect the person's glucose (e.g., meals and exercise) and automatically deliver insulin to mitigate any effects of such a detected event—also without receiving user input for the particular event. These and other advantages of the artificial pancreas system may be described further below. Moreover, the artificial pancreas system may be implemented in a modular fashion, i.e., so that any of a plurality of insulin delivery system providers approved by a glucose monitoring platform are able to securely interface with the platform's components comprising the artificial pancreas system—the wearable glucose monitoring device and the artificial pancreas algorithm.

In the following discussion, an example environment is first described that may employ the techniques described herein. Example implementation details and procedures are then described which may be performed in the example environment as well as other environments. Performance of the example procedures is not limited to the example environment and the example environment is not limited to performance of the example procedures.

Example Environment

FIG. 1 is an illustration of an environment 100 in an example implementation that is operable to employ machine learning in an artificial pancreas as described herein. The illustrated environment 100 includes person 102, who is depicted wearing a wearable glucose monitoring device 104, insulin delivery system 106, and computing device 108. The illustrated environment 100 also includes other users in a user population 110 of the wearable glucose monitoring device, glucose monitoring platform 112, and Internet of Things 114 (IoT 114). The wearable glucose monitoring device 104, insulin delivery system 106, computing device 108, user population 110, glucose monitoring platform 112, and IoT 114 are communicatively coupled, including via a network 116.

Alternately or additionally, the wearable glucose monitoring device 104, the insulin delivery system 106, and the computing device 108 may be communicatively coupled in other ways, such as using one or more wireless communication protocols or techniques. The wearable glucose monitoring device 104, the insulin delivery system 106, and the computing device 108 can be communicatively coupled, for instance, to form an artificial pancreas system as discussed above and below, and particularly in relation to FIG. 4.

The wearable glucose monitoring device 104, the insulin delivery system 106, and the computing device 108 may communicate with one another using one or more of Bluetooth (e.g., Bluetooth Low Energy links), near-field communication (NFC), 5G, and so forth. The wearable glucose monitoring device 104, the insulin delivery system 106, and the computing device 108 may leverage these types of communication to form a closed-loop system between one another, such as an artificial pancreas system. In this way, the insulin delivery system 106 may deliver insulin based on sequences of glucose measurements in real-time as those glucose measurements are obtained by the wearable glucose monitoring device 104.

In accordance with the described techniques, the wearable glucose monitoring device 104 is configured to monitor glucose of the person 102, e.g., continuously. In one or more implementations, the wearable glucose monitoring device 104 may thus be configured as a continuous glucose monitoring (CGM) system. Regardless, the wearable glucose monitoring device 104 may be configured with a glucose sensor, for instance, that continuously detects analytes indicative of the person 102's glucose and enables generation of glucose measurements. In the illustrated environment 100 these measurements are represented as glucose measurements 118. This functionality along with further aspects of the wearable glucose monitoring device 104's configuration are discussed in more detail in relation to FIG. 2.

In one or more implementations, the wearable glucose monitoring device 104 transmits the glucose measurements 118 to the computing device 108, such as via a wireless connection. The wearable glucose monitoring device 104 may communicate these measurements in real-time, e.g., as they are produced using a glucose sensor. Alternately or in addition, the wearable glucose monitoring device 104 may communicate the glucose measurements 118 to the computing device 108 at set time intervals, e.g., every 30 seconds, every minute, every 5 minutes, every hour, every 6 hours, every day, and so forth. Further still, the wearable glucose monitoring device 104 may communicate these measurements responsive to a request from the computing device 108, e.g., communicated to the wearable glucose monitoring device 104 when the computing device 108 causes display of a user interface having information about the person 102's glucose level, updates such a display, uses one of the person 102's glucose measurements (or a sequence of them) for the purpose of delivering insulin, and so forth. Accordingly, the computing device 108 may maintain the glucose measurements 118 of the person 102 at least temporarily, e.g., in computer readable storage media of the computing device 108.

Although illustrated as a wearable device (e.g., a smart watch), the computing device 108 may be configured in a variety of ways without departing from the spirit or scope of the described techniques. By way of example and not limitation, the computing device 108 may be configured as a different type of mobile device (e.g., a mobile phone or tablet device). In one or more implementations, the computing device 108 may be configured as a dedicated device associated with the glucose monitoring platform 112, e.g., with functionality to obtain the glucose measurements 118 from the wearable glucose monitoring device 104, perform various computations in relation to the glucose measurements 118, display information related to the glucose measurements 118 and the glucose monitoring platform 112, communicate the glucose measurements 118 to the glucose monitoring platform 112, receive communications from the insulin delivery system 106, control the insulin delivery system 106 to deliver doses of insulin to the person 102, and so forth. In contrast to implementations where the computing device 108 is configured as a mobile phone, however, the computing device 108 may not include some functionality available with mobile phone or wearable configurations when configured as a dedicated glucose monitoring device, such as the ability to make phone calls, camera functionality, the ability to utilize social networking applications, and so on.

Additionally, the computing device 108 may be representative of more than one device in accordance with the described techniques. In one or more scenarios, for instance, the computing device 108 may correspond to both a wearable device (e.g., a smart watch) and a mobile phone. In such scenarios, both of these devices may be capable of performing at least some of the same operations, such as to receive the glucose measurements 118 from the wearable glucose monitoring device 104, communicate them via the network 116 to the glucose monitoring platform 112, display information related to the glucose measurements 118, receive communications from the insulin delivery system 106, control the insulin delivery system 106 to deliver units of insulin to the person 102, and so forth. Alternately or in addition, different devices may have different capabilities that other devices do not have or that are limited through computing instructions to specified devices.

In the scenario where the computing device 108 corresponds to a separate smart watch and a mobile phone, for instance, the smart watch may be configured with various sensors and functionality to measure a variety of physiological markers (e.g., heartrate, breathing, rate of blood flow, and so on) and activities (e.g., steps) of the person 102. In this scenario, the mobile phone may not be configured with these sensors and functionality or may include a limited amount of that functionality—although in other scenarios a mobile phone may be able to provide the same functionality. Continuing with this particular scenario, the mobile phone may have capabilities that the smart watch does not have, such as a camera to capture images of meals used to predict effective insulin doses, an amount of computing resources (e.g., battery and processing speed) that enables the mobile phone to more efficiently carry out computations in relation to the glucose measurements 118. Even in scenarios where a smart watch is capable of carrying out such computations, computing instructions may limit performance of those computations to the mobile phone so as not to burden both devices and to utilize available resources efficiently. To this extent, the computing device 108 may be configured in different way and represent different numbers of devices than discussed herein without departing from the spirit and scope of the described techniques.

The computing device 108 also includes functionality (e.g., one or more algorithms) to determine insulin doses that are based on the glucose measurements 118 and that are predicted to prevent the person 102's future glucose measurements from departing from a target glucose range. In connection with this, the computing device 108 may control the insulin delivery system 106 to deliver the determined insulin dose, such as by communicating instructions via control signals over a wireless connection established with the insulin delivery system 106, e.g., a Bluetooth Low Energy link. In one or more implementations, the insulin delivery system 106 includes an insulin reservoir and is configured to deliver doses of insulin to the person 102 from this reservoir according to the instructions. This functionality along with further aspects of the insulin delivery system 106 are discussed in more detail in relation to FIG. 3.

As mentioned above, the computing device 108 communicates the glucose measurements 118 to the glucose monitoring platform 112. In the illustrated environment 100, the glucose measurements 118 are shown stored in storage device 120 of the glucose monitoring platform 112. The storage device 120 may represent one or more databases and also other types of storage capable of storing the glucose measurements 118. The storage device 120 also stores a variety of other data. In accordance with the described techniques, for instance, the person 102 corresponds to a user of at least the glucose monitoring platform 112 and may also be a user of one or more other, third party service providers. To this end, the person 102 may be associated with a username and be required, at some time, to provide authentication information (e.g., password, biometric data, and so forth) to access the glucose monitoring platform 112 using the username. This information, along with other information about the user, may be maintained in the storage device 120, including, for example, demographic information describing the person 102, information about a health care provider, payment information, prescription information, determined health indicators, user preferences, account information for other service provider systems (e.g., a service provider associated with a wearable, social networking systems, and so on), and so forth.

The storage device 120 also maintains data of the other users in the user population 110. Given this, the glucose measurements 118 in the storage device 120 include the glucose measurements from a glucose sensor of the wearable glucose monitoring device 104 worn by the person 102 and also include glucose measurements from glucose sensors of wearable glucose monitoring devices worn by persons corresponding to the other users in the user population 110. It follows also that the glucose measurements 118 of these other users are communicated by their respective devices via the network 116 to the glucose monitoring platform 112 and that these other users have respective user profiles with the glucose monitoring platform 112.

The data analytics platform 122 represents functionality to process the glucose measurements 118—alone and/or along with other data maintained in the storage device 120—to generate a variety of predictions, such as by using various machine learning models. Based on these predictions, the glucose monitoring platform 112 may provide recommendations and/or other information about the predictions. Although depicted as separate from the computing device 108, portions or an entirety of the data analytics platform 122 may alternately or additionally be implemented at the computing device 108. The data analytics platform 122 may also generate these predictions using additional data obtained via the IoT 114.

It is to be appreciated that the IoT 114 represents various sources capable of providing data that describes the person 102 and the person 102's activity as a user of one or more service providers and activity with the real world. By way of example, the IoT 114 may include various devices of the user, e.g., cameras, mobile phones, laptops, and so forth. To this end, the IoT 114 may provide information about interaction of the user with various devices, e.g., interaction with web-based applications, photos taken, communications with other users, and so forth. The IoT 114 may also include various real-world articles (e.g., shoes, clothing, sporting equipment, appliances, automobiles, etc.) configured with sensors to provide information describing behavior, such as steps taken, force of a foot striking the ground, length of stride, temperature of a user (and other physiological measurements), temperature of a user's surroundings, types of food stored in a refrigerator, types of food removed from a refrigerator, driving habits, and so forth. The IoT 114 may also include third parties to the glucose monitoring platform 112, such as medical providers (e.g., a medical provider of the person 102) and manufacturers (e.g., a manufacturer of the wearable glucose monitoring device 104, the insulin delivery system 106, or the computing device 108) capable of providing medical and manufacturing data, respectively, that can be leveraged by the data analytics platform 122. Certainly, the IoT 114 may include devices and sensors capable of providing a wealth of data used to predict insulin doses to control glucose levels without departing from the spirit or scope of the described techniques. In the context of measuring glucose, e.g., continuously, and obtaining data describing such measurements, consider the following discussion of FIG. 2.

Figure 2:
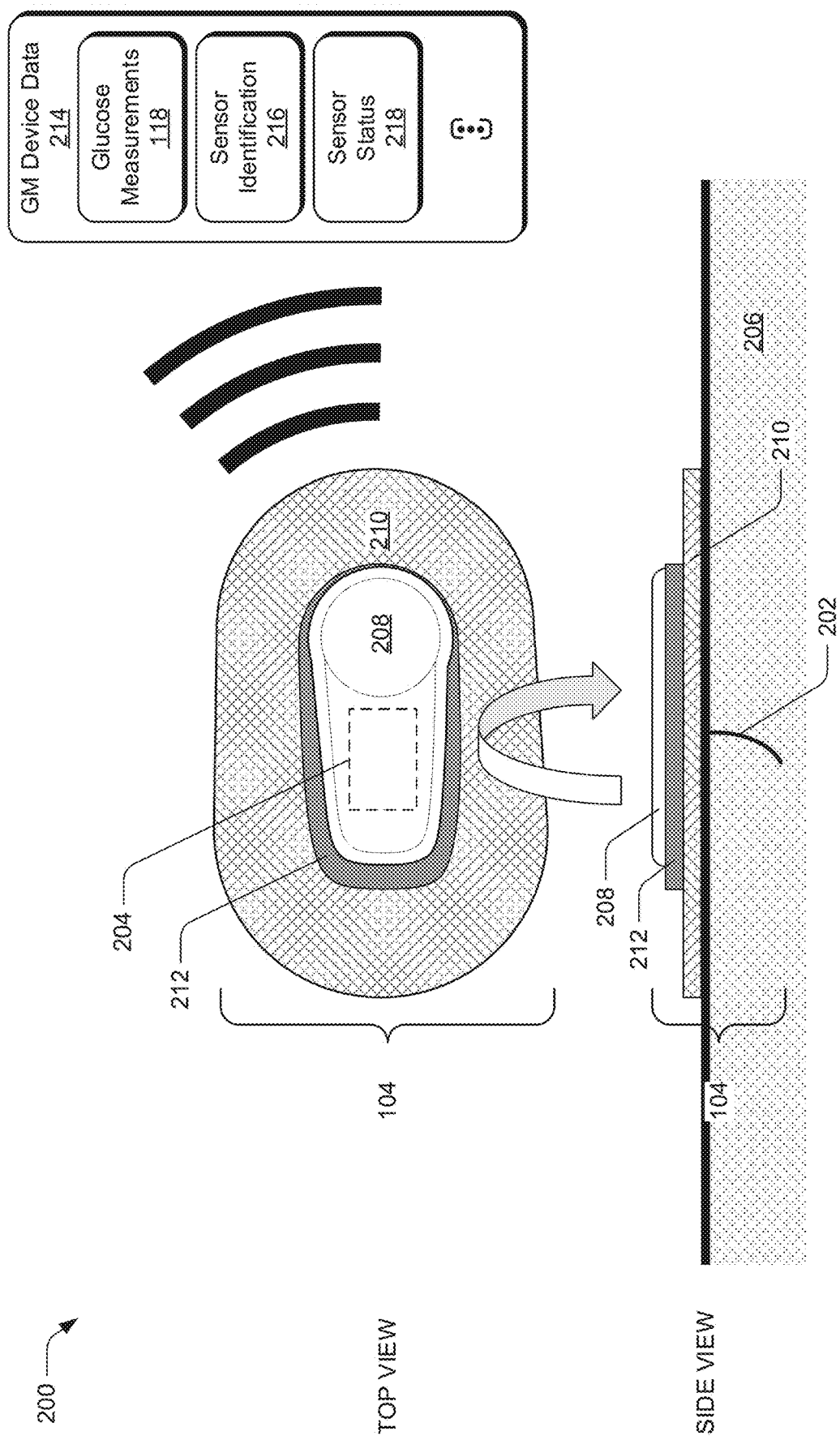
FIG. 2 depicts an example of the wearable glucose monitoring device of FIG. 1 in greater detail.

FIG. 2 depicts an example implementation 200 of the wearable glucose monitoring device 104 of FIG. 1 in greater detail. In particular, the illustrated example 200 includes a top view and a corresponding side view of the wearable glucose monitoring device 104.

The wearable glucose monitoring device 104 is illustrated to include a sensor 202 and a sensor module 204. In the illustrated example 200, the sensor 202 is depicted in the side view having been inserted subcutaneously into skin 206, e.g., of the person 102. The sensor module 204 is depicted in the top view as a dashed rectangle. The wearable glucose monitoring device 104 also includes a transmitter 208 in the illustrated example 200. Use of the dashed rectangle for the sensor module 204 indicates that it may be housed or otherwise implemented within a housing of the transmitter 208. In this example 200, the wearable glucose monitoring device 104 further includes adhesive pad 210 and attachment mechanism 212.

In operation, the sensor 202, the adhesive pad 210, and the attachment mechanism 212 may be assembled to form an application assembly, where the application assembly is configured to be applied to the skin 206 so that the sensor 202 is subcutaneously inserted as depicted. In such scenarios, the transmitter 208 may be attached to the assembly after application to the skin 206 via the attachment mechanism 212. Additionally or alternately, the transmitter 208 may be incorporated as part of the application assembly, such that the sensor 202, the adhesive pad 210, the attachment mechanism 212, and the transmitter 208 (with the sensor module 204) can all be applied at once to the skin 206. In one or more implementations, this application assembly is applied to the skin 206 using a separate applicator (not shown). This application assembly may also be removed by peeling the adhesive pad 210 off of the skin 206. It is to be appreciated that the wearable glucose monitoring device 104 and its various components as illustrated are simply one example form factor, and the wearable glucose monitoring device 104 and its components may have different form factors without departing from the spirit or scope of the described techniques.

In operation, the sensor 202 is communicatively coupled to the sensor module 204 via at least one communication channel which can be a "wireless" connection or a "wired" connection. Communications from the sensor 202 to the sensor module 204 or from the sensor module 204 to the sensor 202 can be implemented actively or passively and these communications can be continuous (e.g., analog) or discrete (e.g., digital).

The sensor 202 may be a device, a molecule, and/or a chemical which changes or causes a change in response to an event which is at least partially independent of the sensor 202. The sensor module 204 is implemented to receive indications of changes to the sensor 202 or caused by the sensor 202. For example, the sensor 202 can include glucose oxidase which reacts with glucose and oxygen to form hydrogen peroxide that is electrochemically detectable by the sensor module 204 which may include an electrode. In this example, the sensor 202 may be configured as or include a glucose sensor configured to detect analytes in blood or interstitial fluid that are indicative of glucose level using one or more measurement techniques.

In another example, the sensor 202 (or an additional sensor of the wearable glucose monitoring device 104—not shown) can include a first and second electrical conductor and the sensor module 204 can electrically detect changes in electric potential across the first and second electrical conductor of the sensor 202. In this example, the sensor module 204 and the sensor 202 are configured as a thermocouple such that the changes in electric potential correspond to temperature changes. In some examples the sensor module 204 and the sensor 202 are configured to detect a single analyte, e.g., glucose. In other examples, the sensor module 204 and the sensor 202 are configured to detect multiple analytes, e.g., sodium, potassium, carbon dioxide, and glucose. Alternately or additionally, the wearable glucose monitoring device 104 includes multiple sensors to detect not only one or more analytes (e.g., sodium, potassium, carbon dioxide, glucose, and insulin) but also one or more environmental conditions (e.g., temperature). Thus, the sensor module 204 and the sensor 202 (as well as any additional sensors) may detect the presence of one or more analytes, the absence of one or more analytes, and/or changes in one or more environmental conditions.

In one or more implementations, the sensor module 204 may include a processor and memory (not shown). The sensor module 204, by leveraging the processor, may generate the glucose measurements 118 based on the communications with the sensor 202 that are indicative of the above-discussed changes. Based on these communications from the sensor 202, the sensor module 204 is further configured to generate glucose monitoring device data 214. The glucose monitoring device data 214 is a communicable package of data that includes at least one glucose measurement 118. Alternately or additionally, the glucose monitoring device data 214 includes other data, such as multiple glucose measurements 118, sensor identification 216, sensor status 218, and so forth. In one or more implementations, the glucose monitoring device data 214 may include other information such as one or more of temperatures that correspond to the glucose measurements 118 and measurements of other analytes. It is to be appreciated that the glucose monitoring device data 214 may include a variety of data in addition to at least one glucose measurement 118 without departing from the spirit or scope of the described techniques.

In operation, the transmitter 208 may transmit the glucose monitoring device data 214 wirelessly as a stream of data to the computing device 108. Alternately or additionally, the senor module 204 may buffer the glucose monitoring device data 214 (e.g., in memory of the sensor module 204) and cause the transmitter 208 to transmit the buffered glucose monitoring device data 214 at various intervals, e.g., time intervals (every second, every thirty seconds, every minute, every five minutes, every hour, and so on), storage intervals (when the buffered glucose monitoring device data 214 reaches a threshold amount of data or a number of instances of glucose monitoring device data 214), and so forth.

In addition to generating the glucose monitoring device data 214 and causing it to be communicated to the computing device 108, the sensor module 204 may include additional functionality in accordance with the described techniques. This additional functionality may include generating predictions of glucose levels of the person 102 in the future and communicating notifications based on the predictions, such as by communicating warnings when the predictions indicate that the person 102's level of glucose is likely to be dangerously low in the near future. This computational ability of the sensor module 204 may be advantageous especially where connectivity to services via the network 116 is limited or non-existent. In this way, a person may be alerted to a dangerous condition without having to rely on connectivity, e.g., to the Internet. This additional functionality of the sensor module 204 may also include calibrating the sensor 202 initially or on an ongoing basis as well as calibrating any other sensors of the wearable glucose monitoring device 104.

With respect to the glucose monitoring device data 214, the sensor identification 216 represents information that uniquely identifies the sensor 202 from other sensors, such as other sensors of other wearable glucose monitoring device 104, other sensors implanted previously or subsequently in the skin 206, and so on. By uniquely identifying the sensor 202, the sensor identification 216 may also be used to identify other aspects about the sensor, 202 such as a manufacturing lot of the sensor 202, packaging details of the sensor 202, shipping details of the sensor 202, and so on. In this way, various issues detected for sensors manufactured, packaged, and/or shipped in a similar manner as the sensor 202 may be identified and used in different ways, e.g., to calibrate the glucose measurements 118, to notify users to change defective sensors or dispose of them, to notify manufacturing facilities of machining issues, and so forth.

The sensor status 218 represents a state of the sensor 202 at a given time, e.g., a state of the sensor at a same time one of the glucose measurements 118 is produced. To this end, the sensor status 218 may include an entry for each of the glucose measurements 118, such that there is a one-to-one relationship between the glucose measurements 118 and statuses captured in the sensor status 218 information. Generally speaking, the sensor status 218 describes an operational state of the sensor 202. In one or more implementations, the sensor module 204 may identify one of a number of predetermined operational states for a given glucose measurement 118. The identified operational state may be based on the communications from the sensor 202 and/or characteristics of those communications.

By way of example, the sensor module 204 may include (e.g., in memory or other storage) a lookup table having the predetermined number of operational states and bases for selecting one state from another. For instance, the predetermined states may include a "normal" operation state where the basis for selecting this state may be that the communications from the sensor 202 fall within thresholds indicative of normal operation, e.g., within a threshold of an expected time, within a threshold of expected signal strength, an environmental temperature is within a threshold of suitable temperatures to continue operation as expected, and so forth. The predetermined states may also include operational states that indicate one or more characteristics of the sensor 202's communications are outside of normal activity and may result in potential errors in the glucose measurements 118.

For example, bases for these non-normal operational states may include receiving the communications from the sensor 202 outside of a threshold expected time, detecting a signal strength of the sensor 202 outside a threshold of expected signal strength, detecting an environmental temperature outside of suitable temperatures to continue operation as expected, detecting that the person 102 has rolled (e.g., in bed) onto the wearable glucose monitoring device 104, and so forth. The sensor status 218 may indicate a variety of aspects about the sensor 202 and the wearable glucose monitoring device 104 without departing from the spirit or scope of the described techniques.

Figure 3:
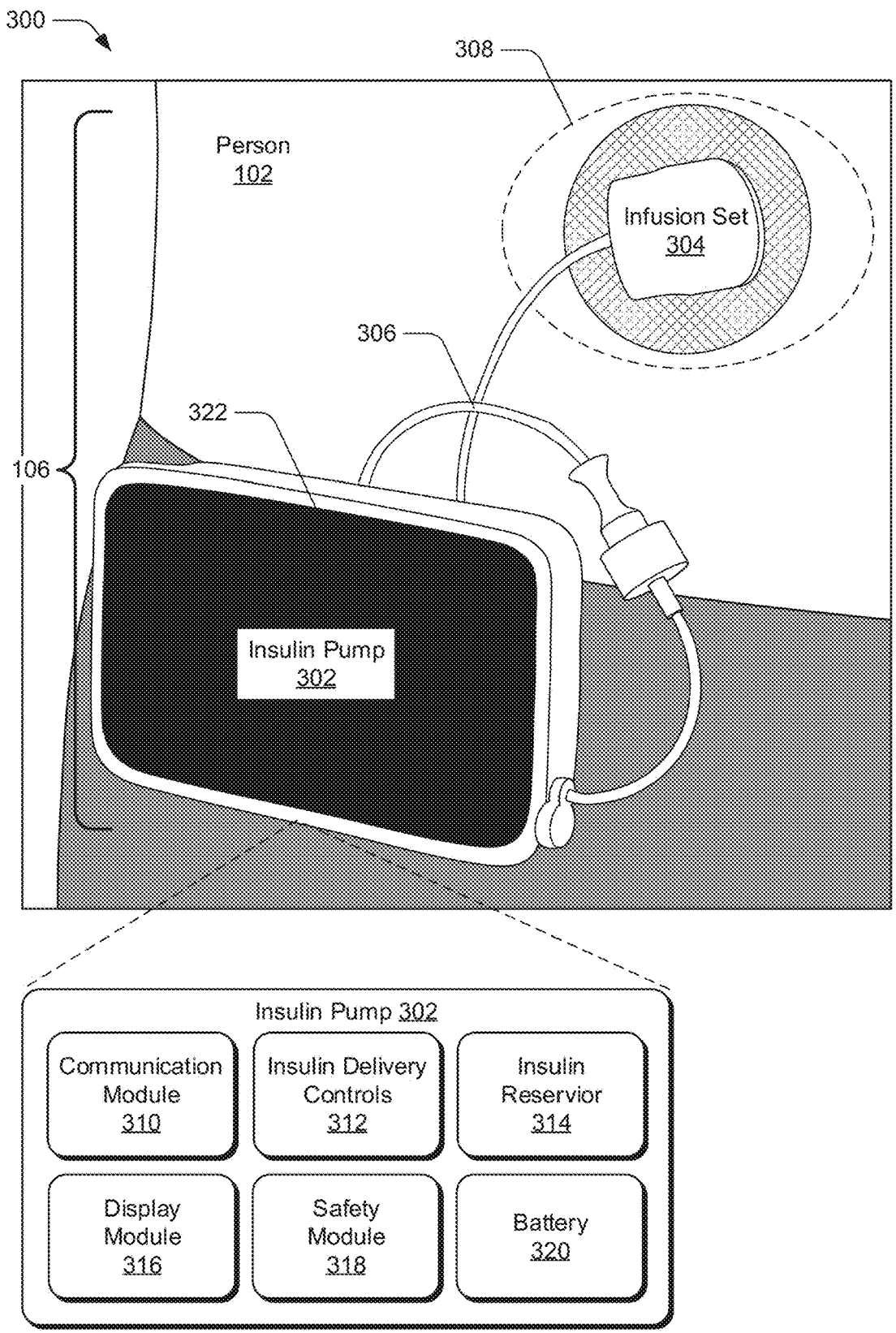
FIG. 3 depicts an example of the insulin delivery system of FIG. 1 in greater detail.

FIG. 3 depicts an example implementation 300 of the insulin delivery system 106 of FIG. 1 in greater detail.

In the illustrated example 300, the insulin delivery system 106 includes an insulin pump 302 and infusion set 304. Although the infusion set 304 is depicted with tubing 306 connected to the insulin pump 302, in one or more implementations the infusion set 304 may be tubeless. Broadly speaking, the infusion set 304 is an apparatus configured to subcutaneously deliver insulin—pumped to the infusion set 304 by the insulin pump 302—into the person 102 for absorption by the person 102's bloodstream. In this way, the delivered insulin may be used by the person 102's body to maintain balanced glucose levels, e.g., within a target range of glucose measurements. In one or more implementations, the infusion set 304 includes a cannula that is inserted subcutaneously into skin, such as at infusion site 308 of the person 102 in the illustrated example 300. Accordingly, the infusion set 304 may administer doses of insulin through the skin of the person 102, e.g., in a continuous manner and at programmable rates. As discussed herein, for instance, basal and/or bolus doses of insulin may be administered through the skin of the person 102 via the infusion set 304.

As illustrated, the infusion set 304 includes an adhesive pad which affixes the apparatus to the person 102 for a period of time. In one or more implementations, the infusion set 304 is applied to the infusion site 308 using a separate applicator (not shown). In operation, this applicator may inject the infusion set 304's cannula into the person 102's skin at the infusion site 308 and also affix the adhesive pad to the infusion site 308 to secure the infusion set 304 to the person 102 for a period of use. In at least some implementations, for instance, infusion sets may be disposable such that they are designed for removal after a prescribed and/or recommended period of time and for replacement with a new set that is applied to the person 102 and attached to the insulin pump 302. In any case, the insulin pump 302 is configured to deliver insulin doses to the person 102 via infusion sets, such as the illustrated infusion set 304.

In the illustrated example 300, the insulin pump 302 includes communication module 310, insulin delivery controls 312, insulin reservoir 314, display module 316, safety module 318, and battery 320. In implementation, the insulin pump 302 may be configured in various ways, such as with some of these components while others are housed or otherwise implemented in separate devices. Alternately or additionally, the insulin pump 302 may include additional or alternate components without departing from the spirit or scope of the techniques described herein.

The communication module 310 is configured to transmit data to and receive data from other devices, such as the computing device 108. In one or more implementations, the communication module 310 establishes communicative couplings with such other devices to enable transmission and receipt of data. By way of example, the communication module 310 may establish, or otherwise facilitate establishing, links or channels of communication with those other devices. The links or channels may be configured in various ways, including but not limited to Bluetooth (e.g., Bluetooth Low Energy links), Near Field Communication (NFC), 5G or other cellular, and WiFi, to name just a few. Such communicative couplings enable the insulin pump 302 to communicate over different networks, such as the network 116 and/or securely within an artificial pancreas system as discussed in relation to FIG. 4.

Once a communicative coupling is established, the communication module 310 can cause data to be transmitted over the established coupling and/or can receive data from other devices over the established coupling. Additionally or alternately, the communication module 310 may be configured to establish connections over wired communication channels—such as via a USB cord connected to the insulin pump 302 and another device—and also configured to transmit and/or receive data over such a wired coupling. The communication module 310 may be configured in various ways to enable the insulin pump 302 to communicate with other devices.

As one example, the communication module 310 enables the insulin pump 302 to receive instructions from the computing device 108 for controlling delivery of insulin to the person 102. For instance, the communication module 310 enables the insulin pump 302 to receive instructions that instruct the insulin pump 302 regarding delivery of a basal rate of insulin to the person 102, updates to the basal rate of insulin, delivery of bolus doses of insulin to the person 102 (e.g., an amount to bolus within a limited time), and so forth. The computing device 108 may send a variety of communications to the insulin delivery system 106 for controlling insulin delivery without departing from the spirit or scope of the techniques described herein.

The insulin delivery controls 312 represent any hardware, software, and/or mechanical components of the insulin pump 302 that cause insulin to be pumped (or otherwise extracted) from the insulin reservoir 314 so that it flows through the infusion set 304 and into the person 102. Moreover, the insulin delivery controls 312 are further configured to cause the insulin to be pumped or otherwise extracted from the insulin reservoir 314 in accordance with insulin dose instructions, e.g., from the computing device 108 which specify one or more deliveries of the insulin. The insulin reservoir 314 is configured to house an amount of insulin, which by leveraging the functionality of the insulin pump 302 may be subcutaneously delivered via the infusion set 304. The insulin reservoir 314 may be replaceable or otherwise configured so that the amount of insulin can be replenished in the insulin reservoir 314. The insulin reservoir 314 may be configured in various ways (e.g., different shapes, different materials, differently removable, and so on) without departing from the spirit or scope of the described techniques.

The display module 316 is configured to cause display of information via a display device 322 of the insulin pump 302. The display module 316 may generate one or more user interfaces for display via the display device 322. By way of example, the display module 316 may cause display via the display device of a user interface for setting up a wireless connection with the computing device 108. Additionally or alternately, the display module 316 may cause the display device 322 to display glucose measurements (e.g., in a similar manner as they are displayed via a glucose monitoring application of the computing device 108), trend arrows (e.g., regarding an identified trend in the glucose measurements), alerts (e.g., about the glucose measurements, other physiological conditions, operability of the insulin delivery system 106, operability of components of an artificial pancreas system, status of a wireless connection with the computing device 108, and so on), pump set up interfaces, indications of being out of communication range from different devices (e.g., the computing device 108 or the wearable glucose monitoring device 104), and so forth. The display module 316 may thus cause a variety of information to be displayed via the display device 322 of the insulin pump 302.

Safety module 318 is configured to provide one or more safeguards to control delivery of insulin so that the delivery is not harmful; in other words, so that the insulin delivered is safely. By way of example, the safety module 318 may contain or otherwise enforce delivery limits, such as maximum and minimum rates of delivery over different periods of time. These limits are effective to prevent erroneous delivery instructions from the computing device 108 from harming the person 102, such as when an error transmitting the instructions affects their contents or when an error in a prediction made by one or more machine learning models dangerously affects those instructions. For instance, the safety module 318 may limit an amount or rate of insulin that the insulin pump 302 delivers to a threshold amount or threshold rate, even if instructions received from the computing device 108 instruct the insulin pump 302 to deliver more than the threshold amount. Similarly, the safety module 318 may also prevent the insulin pump from delivering less than a threshold amount of insulin or delivering insulin at less than a threshold rate, even if instructions received from the computing device 108 instruct the insulin pump to deliver less than the threshold amount.

In addition, the safety module 318 is configured to continue operating the insulin pump 302 in the absence of instructions from the computing device 108, e.g., in the absence of instructions describing how much insulin to deliver and when. The safety module 318 may be configured to continue operating the insulin pump 302 to deliver insulin to the person 102 when the computing device 108 is out of communication range, for example. The safety module 318 may have access to logic, default settings, or settings entered as part of a set up process, to name just a few, that control how much insulin the insulin pump is to deliver when instructions are not being received from the computing device 108. The safety module 318 may perform various additional or different safeguards to ensure that an amount of insulin delivered is not harmful to the person 102.

The battery 320 is configured to provide power for operating the insulin pump 302, such as to power the communication module 310 to send and receive data, to power the insulin delivery controls 312 to cause delivery of insulin from the insulin reservoir to the person 102 via the infusion set, to power the display module 316 to display information via the display device 322, and so forth. The battery 320 may be rechargeable (e.g., via a USB charging port) or replaceable. It is to be appreciated that the battery 320 may be configured in various ways.

Although not depicted, the insulin delivery system 106 or another device (e.g., the wearable glucose monitoring device 104) may be configured with an insulin sensor. Such an insulin sensor may be applied to skin or inserted subcutaneously to measure a systemic level of insulin, e.g., in the person 102. Accordingly, the insulin sensor may be included as part of the infusion set 304, the wearable glucose monitoring device 104, or may be separately applied. In any case, such an insulin sensor may be used in connection with the safety module 318 and/or with dose prediction functionality of the computing device 108. In this way, insulin measurements produced using the insulin sensor can be used to prevent or detect an overdose in insulin, e.g., to prevent the person receiving insulin from experiencing an episode of hypoglycemia. By way of example, the safety module 318 may shut off insulin delivery by the insulin pump 302 based on the insulin measurements, e.g., if the safety module 318 detects the level of insulin surpasses a predetermined threshold. Based on the insulin measurements, the computing device 108 may also or alternately send instructions to the insulin delivery system 106, instructing it to cease insulin delivery. In one or more implementations, the safety module 318 and/or the computing device 108 may also trigger alerts if the level of insulin surpasses the predetermined threshold. Physiologically, different thresholds may be determined for different persons based on their insulin sensitivities, such that the above-discussed shut down, alerts, or cease to insulin delivery may be triggered at different insulin levels for the different persons. As described in more detail below, the artificial pancreas system may also use such an insulin sensor to determine various factors for controlling insulin doses for the person 102, such as the person 102's carbohydrate-to-glucose ratio and insulin sensitivity factor.

Having considered an example environment, example wearable glucose monitoring device, and example insulin delivery system, consider now a discussion of some example details of the techniques for machine learning in an artificial pancreas in a digital medium environment in accordance with one or more implementations.

Machine Learning in an Artificial Pancreas

Figure 4:
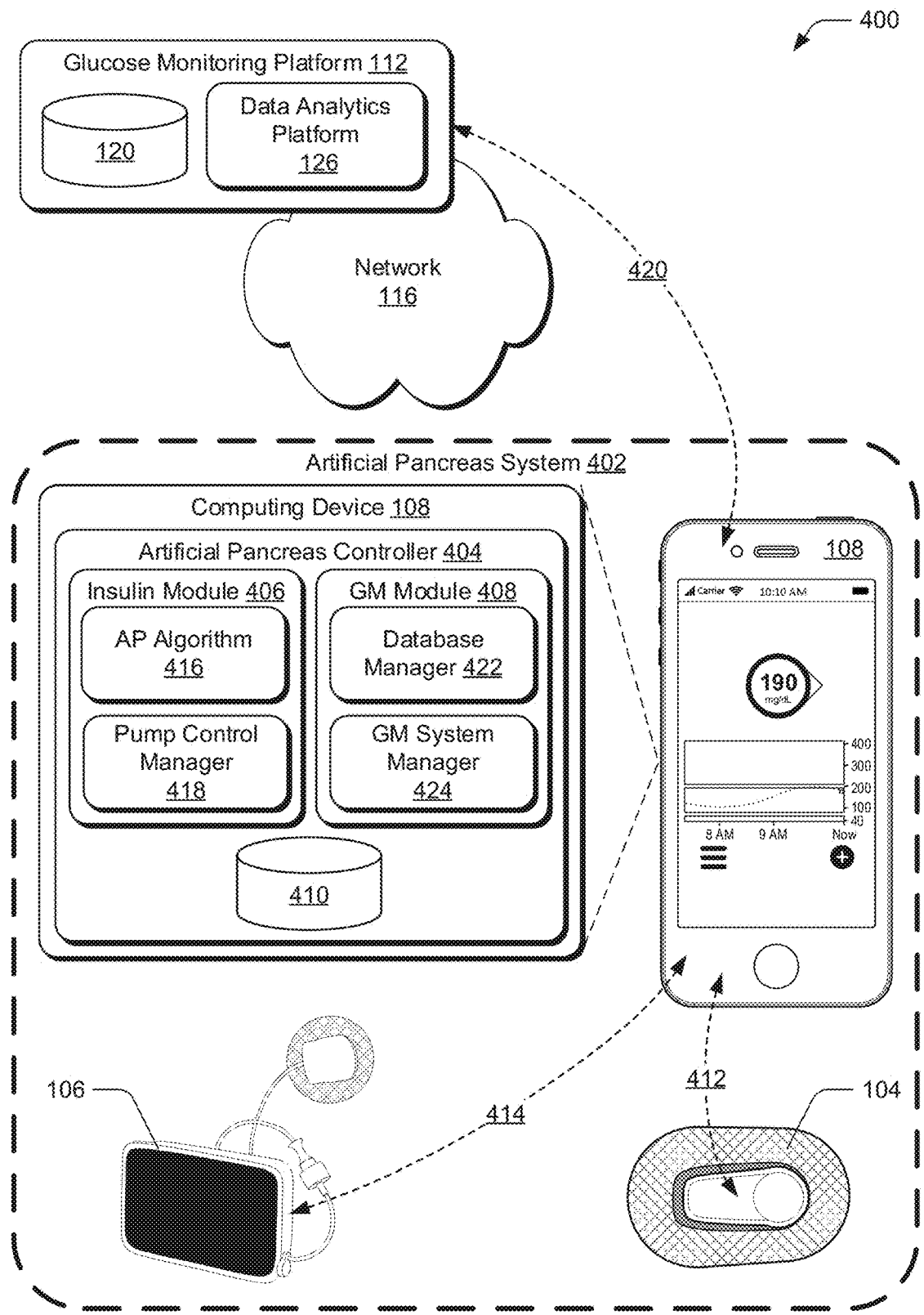
FIG. 4 depicts an example implementation in which the wearable glucose monitoring device, the insulin delivery system, and the computing device of FIG. 1 are configured as an artificial pancreas.

FIG. 4 depicts an example implementation 400 in which the wearable glucose monitoring device 104, the insulin delivery system 106, and the computing device 108 of FIG. 1 are configured as an artificial pancreas.

In the illustrated example 400, artificial pancreas system 402 includes the wearable glucose monitoring device 104, the insulin delivery system 106, and the computing device 108, which is illustrated as a mobile phone in this example. The computing device 108 is further illustrated having artificial pancreas controller 404, which includes insulin module 406, glucose monitoring module 408, and shared storage 410 (e.g., a database). It is to be appreciated that although the artificial pancreas controller 404 and its components are illustrated as part of the computing device 108, in one or more implementations, portions of the artificial pancreas controller 404, those modules, and the shared storage 410 may be implemented at other devices, such as other computing devices (e.g., a smart watch or servers of the glucose monitoring platform 112), the wearable glucose monitoring device 104, and/or the insulin delivery system 106. Regardless, the artificial pancreas controller 404 includes or otherwise has access to the functionality described in relation to the insulin module 406, the glucose monitoring module 408, and the shared storage 410.

In accordance with the techniques described herein, the wearable glucose monitoring device 104, the insulin delivery system 106, and the computing device 108 may form the artificial pancreas system 402 as a fully-closed loop system, such that user interaction to monitor glucose (e.g., finger pricks), determine insulin doses (e.g., based on past experience, journaling previous doses and bodily response, referencing dose tables), and actually select an amount of insulin to deliver and when, is eliminated and handled instead by the system. Such a closed loop system may be useful not only daily for persons with Type I and Type II diabetes, but also at hospitals or other health-care locations temporarily providing insulin therapy.

The wearable glucose monitoring device 104 and the insulin delivery system 106 are communicatively coupled to the computing device 108 via wireless connections 412, 414, respectively. In one or more implementations, there is no communicative coupling between the wearable glucose monitoring device 104 and the insulin delivery system 106—no wireless connections are established. Instead, the artificial pancreas controller 404 handles communications on behalf of these devices to implement the artificial pancreas system 402, such as by receiving data from the wearable glucose monitoring device 104 over the wireless connection 412, processing the received data as discussed above and below, and transmitting various instructions and/or portions of the processed data to the insulin delivery system 106 over the wireless connection 414. Similarly, the artificial pancreas controller 404 can receive data from the insulin delivery system 106 over the wireless connection 414, process the data received from the insulin delivery system 106, and transmit instructions (e.g., status or data requests, requests to perform various operations such as provide a current glucose measurement, and so on) or other data (e.g., algorithm or firmware updates) to the wearable glucose monitoring device 104 over the wireless connection 412.

In this way, handling communications between the glucose monitoring platform 112's wearable glucose monitoring device 104 and different insulin delivery systems, which may be available from a plurality of third parties to the glucose monitoring platform 112, is offloaded from the wearable glucose monitoring device 104 and the insulin delivery systems. Accordingly, interfacing between these devices, for the purpose of implementing the artificial pancreas system 402, may be handled at the software level rather than being handled by hardware and firmware of the wearable glucose monitoring device 104 and/or the insulin delivery system 106. By implementing the artificial pancreas system 402 in this way, the glucose monitoring platform 112 need not divulge specifics regarding how the wearable glucose monitoring device 104 and the computing device 108 communicate, e.g., types of communication channels used, communication protocols, and/or structures of data communicated. Rather, the artificial pancreas controller 404 may include or otherwise have access to a plurality of interfaces, where each interface converts data for transmission to the insulin delivery system 106 (e.g., instructions for controlling delivery of insulin doses or instructions to display various information) to a specified format accepted by the insulin delivery system 106 and also converts data received from the insulin delivery system 106 into a specified format for processing by the artificial pancreas controller 404.

In one or more implementations, there may be an interface for each different insulin delivery system 106 authorized for use as part of the artificial pancreas system 402. In other words, there may be a different interface for each third-party that sells an insulin delivery system authorized for use as part of the artificial pancreas system 402 and/or a different interface for each different model of insulin delivery system authorized for use as part of the artificial pancreas system 402. Although the techniques herein are generally described without establishment and use of a wireless connection between the wearable glucose monitoring device 104 and the insulin delivery system 106—for the purpose of implementing the artificial pancreas system 402—it is to be appreciated that in some implementations there may be a wireless connection between the wearable glucose monitoring device 104 and the insulin delivery system 106, such as to communicate alerts (e.g., detection of soon-occurring hyper- or hypo-glycemia, device malfunctions, etc.).

Turning now to a more detailed discussion of the artificial pancreas controller 404, the insulin module 406 generally represents functionality to enable communications with the insulin delivery system 106, determine doses of insulin to deliver, and control the insulin delivery system 106 to deliver the determined doses. By way of contrast, the glucose monitoring module 408 represents functionality to enable communications with the wearable glucose monitoring device 104, such as to receive the glucose measurements 118, and also to process the data received from the wearable glucose monitoring device 104 so that the received data can be used to determine insulin doses. This may include extracting portions of the glucose monitoring device data 214 received from the wearable glucose monitoring device 104 (e.g., the glucose measurements 118) and/or packaging at least some portions of this data with supplemental data from the computing device 108 (e.g., data describing application usage or health-related aspects at a time correlated to the glucose measurements 118).

In one or more implementations, the artificial pancreas controller 404 may be configured to handle pairing between the wearable glucose monitoring device 104 and the computing device 108 and also between the insulin delivery system 106 and the computing device 108. It is further to be appreciated that either one or both of the insulin module 406 and glucose monitoring module 408 may specifically include this functionality. In some implementations, only one of those modules may include the functionality to pair the wearable glucose monitoring device 104 and the insulin delivery system 106 with the computing device 108. Regardless, the artificial pancreas controller 404 may pair the devices, in part, by causing display of a user interface via a display device of the computing device 108 and by receiving user input via the user interface, such as user input to select a manufacturer of the insulin delivery system 106 and/or provide a serial number of the insulin delivery system 106. It is to be appreciated that the user interface may also enable the user to use the computing device 108 to capture an image of the manufacturer and/or serial number, such as by capturing a digital image of that information as affixed to a housing of the insulin delivery system 106 and/or as included on a box of the insulin delivery system 106. The artificial pancreas controller 404 may receive similar user inputs about the wearable glucose monitoring device 104 to pair it with the computing device 108.

In one or more implementations, the artificial pancreas controller 404 may also cause display of educational information about the artificial pancreas system 402 during the pairing or while the system is otherwise being setup, e.g., during a "warm up" time of the wearable glucose monitoring device 104's sensor. The artificial pancreas controller 404 can also be configured to generate and cause output of alerts via one or more of the wearable glucose monitoring device 104, the insulin delivery system 106, the computing device 108, and remote computing devices, e.g., of a health care professional associated with the person 102. By way of example, these alerts may be output responsive to receiving one or more glucose measurements 118 from the wearable glucose monitoring device 104 which indicate the person 102's glucose is outside the target range or is predicted to be outside the target range in the future. Additionally or alternately, these alerts may be output responsive to device or functionality failure, e.g., blockage in the insulin delivery system 106.

In one or more scenarios, the artificial pancreas controller 404 may also cause these alerts to escalate. For instance, the artificial pancreas controller 404 may comply with device settings on a first alert, e.g., by simply causing the insulin delivery system 106 to vibrate. If the first alert is not acknowledged by the person 102 (e.g., by providing some user input indicative of acknowledgment), the artificial pancreas controller 404 may cause an escalating output for a second alert, e.g., the computing device 108 audibly outputs an alert five minutes later. If the second alert also is not acknowledged by the person 102, the artificial pancreas controller 404 may cause a further escalating output for a third alert, e.g., causing the insulin delivery system 106 to output an audible alert with medium volume. If the third alert also is not acknowledged by the person 102, the artificial pancreas controller 404 may cause an even further escalating output for a fourth alert, e.g., the computing device 108 again audibly outputs an alert five minutes later. This escalation may continue until the person 102 or some other person (e.g., a health care professional) acknowledges an alert. Indeed, the artificial pancreas controller 404 may escalate alerts among the different devices of the artificial pancreas system 402 in a variety of ways without departing from the spirit or scope of the described techniques.

Regarding the modules of the artificial pancreas controller 404, the insulin module 406 includes artificial pancreas algorithm 416 and pump control manager 418. The artificial pancreas algorithm 416 is configured to generate predictions of insulin doses that will prevent the person 102's glucose measurements 118 from departing a target range or, said another way, to keep the person 102's glucose measurements 118 generally within the target range. Generally, extreme or sustained departures from such a target range can result in dangerous health conditions and/or damage to a person's body, e.g., heart, blood vessels, eyes, kidneys, and nerves. Maintaining glucose levels within the target range, through timely insulin delivery, can thus help avoid those dangerous health conditions and bodily damage.

As discussed in more detail below, the insulin doses determined using the artificial pancreas algorithm 416 can include both basal rate changes and bolus doses. It is to be appreciated that the artificial pancreas algorithm 416 may be configured in a variety of ways to handle determination of both basal rate changes and bolus insulin doses. To the extent that basal rate changes and bolus doses generally apply to different types of scenarios—basal rate doses correspond to longer acting forms of insulin to keep glucose levels stable through periods of fasting and bolus doses correspond to shorter acting insulin to prevent rises of glucose levels resulting from meals or to immediately correct glucose levels—determination of these different types of doses may involve consideration of different aspects of the person 102's context and thus different inputs. Accordingly, the artificial pancreas algorithm 416 may comprise a machine learning model or an ensemble of them. Such machine learning models may be configured according to various paradigms, such as supervised learning, unsupervised learning, reinforcement learning, transfer learning, and so on.

In one or more implementations, the artificial pancreas algorithm 416 and/or the models it comprises may be trained or otherwise learned initially using the glucose measurements 118 and other user data describing characteristics of the user population 110 and maintained in the storage device 120, including delivered insulin doses, insulin measurements, target glucose ranges, insulin sensitivities, carb ratios, food consumption data, and activity data, to name just a few. Further, this other user data may be correlated with the glucose measurements 118, for instance, based on timestamps of the glucose measurements 118 and the other data. The initially trained artificial pancreas algorithm 416 may then be communicated over connection 420 (which may be wired, wireless, or a combination) for incorporation with the artificial pancreas controller 404. Once incorporated, the artificial pancreas algorithm 416 may be further trained so that it is customized for the person 102, i.e., the person associated with the computing device 108 and wearing the particular wearable glucose monitoring device 104 and the particular insulin delivery system 106.

In one or more implementations, the further training so that the artificial pancreas algorithm 416 is customized for the person 102 may include transfer learning to personalize the artificial pancreas algorithm 416—to personalize it from a state as trained with training data of the user population 110 to an updated state trained with additional training data or (update data) describing one or more aspects of the person 102 and/or describing one or more aspects of a subset of the user population 110 determined similar to the person 102. Similarity may be based on a variety of aspects, such as age, gender, diagnosed medical conditions, glucose measurements, and other physiological measures, to name just a few. By way of example, such transfer learning may be used in connection with calculating the person 102's insulin-carbohydrate ratio and/or insulin sensitivity factor. Such transfer learning can be advantageous during initialization of the person 102's system because while there is still relatively little data about the person 102 available for personalizing the artificial pancreas algorithm 416, the algorithm is nevertheless capable of generating predictions due to the wealth of information from the user population 110 with which it is initially trained.

For example, the artificial pancreas algorithm 416 may be further trained so that it is personalized for the person 102, in part, by obtaining target measurements, target measurement ranges, and/or starting doses from a health care provider of the person 102. Starting doses of insulin may be obtained for a basal titration process, for instance, and through the process adjusted as described in more detail below. Data for the basal titration process may be obtained from the health care provider (e.g., via a health care provider portal of the glucose monitoring platform 112) and/or via one or more user interfaces displayed via the computing device 108. Such user interfaces may be displayed in connection with setting up the artificial pancreas system 402 for use, for example. In this latter scenario, the computing device 108 may receive input from a user (e.g., the person 102) via a series or sequence of these setup interfaces. The artificial pancreas algorithm 416 may also be further trained using data similar to the data initially used from the user population 110, but that is obtained about the person 102, such as the person 102's historical glucose measurements 118, delivered insulin doses, insulin measurements, target glucose ranges, insulin sensitivities, carb ratios, food consumption data, activity data, and so on. Like the user population 110 data, the glucose measurements 118 of the person 102 may be correlated with the other data, such as based on timestamps of the glucose measurements 118 and the other data.

It is to be further appreciated that the artificial pancreas algorithm 416 may use the above-noted example initialization information—target measurements, target measurement ranges, and/or starting doses obtained from a health care provider—for determining insulin doses for a predetermined amount of time before beginning to deviate from the initialization information. By way of example, the artificial pancreas algorithm 416 may initially output (e.g., for a first day, first week, first month, etc.) insulin doses for delivery that correspond to those specified by the person 102's health care provider. After the predetermined amount of time has lapsed, however, the artificial pancreas algorithm 416 may deviate from the health care provider specified doses, e.g., by adjusting those doses based on real-time data received about the person 102. Rather than wait until a predetermined amount of time has lapsed, the artificial pancreas algorithm 416 may alternately wait to deviate from the health care provider specified doses until a threshold amount of data is collected about the person 102, so that accurate predictions of the person 102's behavior can be generated. In scenarios where the artificial pancreas algorithm 416 waits until a suitable amount of data is collected to be able to generate accurate predictions, a determination of "enough" data about the person 102 may be based on one or more learning rate parameters of the artificial pancreas algorithm 416. In general, the learning rate of the artificial pancreas algorithm 416 may prevent the algorithm from making too drastic of changes to the initially specified doses that could be harmful to the person 102.

With respect to inputs to the artificial pancreas algorithm 416, the insulin module 406 may provide data describing various characteristics of the person 102 that are relevant to determining insulin doses. In one or more implementations, these inputs may be configured as feature vectors, where each feature of the vector is configured to represent a predetermined characteristic relevant to determining insulin doses. In operation, each of these features can be set to a value indicative of the respective characteristic as it is detected and recorded in relation to the person 102 at the time of input. The inputs (e.g., corresponding to features of input feature vectors) may include, for instance, a target glucose range, an initial basal insulin dose rate, a previously delivered insulin dose or a sequence of them, one or more sequences of the glucose measurements 118 (e.g., from the wearable glucose monitoring device 104), one or more sequences of insulin measurements, one or more sequences of other physiological measurements (e.g., temperature, heart rate, and so on), data indicative of meals consumed and/or to be consumed (e.g., images, data input via various editable data fields of a user interface, selections made via a user interface), data indicative of exercise (e.g., steps or heart data obtained from a smart watch, workout data obtained from an exercise bike or other exercise machine, and so on), subtypes of diabetes, insulin sensitivity, carb ratio, and so forth.

In one or more implementations, the inputs to the artificial pancreas algorithm 416 may describe physiologic insulin sensitivity of the person 102 and also relative effectiveness of insulin infusion sites of the person 102 where infusion sets 304 are applied to the person 102. In this context, "effectiveness" refers to an ability of the person 102's body to use insulin delivered via an infusion site to control the person 102's glucose. The more "effective" a site, the better insulin delivered via the site controls the person 102's glucose, such that when insulin is delivered via more effective sites of the person 102, the effectiveness approaches and/or substantially matches the person 102's physiologic insulin sensitivity. In contrast, insulin delivered via less effective sites is less effective than an effectiveness indicated by the person 102's physiologic insulin sensitivity. Given this, the artificial pancreas system 402 may measure the physiologic insulin sensitivity of the person 102 and the effectiveness of an insulin infusion site (e.g., infusion site 308). The artificial pancreas algorithm 416 may then determine insulin doses to be delivered via at the insulin infusion site based, in part, on the person 102's insulin sensitivity and on the effectiveness of the site. By way of example, the artificial pancreas 416 may determine higher doses of insulin to deliver via sites that are less effective. Alternately or additionally, the artificial pancreas system 402 may cause output of messages when an infusion site is less effective than a threshold effectiveness, such as messages recommending that the infusion site be changed to a different infusion site, that the person limit a period of time that the infusion site is used, and so forth.

In order to measure a person's physiologic insulin sensitivity and effectiveness of different infusion sites, the artificial pancreas system 402 is configured to learn and build a model of the physiologic insulin sensitivity (which may generally be stable) and the potentially variable infusion site specific insulin sensitivity. As part of building this model, the artificial pancreas system 402 samples the person 102's glucose during use of different infusion sites. For each different infusion site, the artificial pancreas system 402 also records amounts of insulin delivered via the site, times insulin is delivered via the site (e.g., start time of a delivery, end time, and/or duration), type of insulin delivered via the site, and so forth. The artificial pancreas system 402 may also record other information about an infusion site, including, for example, one or more of a location on the person 102's body, a time an infusion set is affixed or otherwise applied to the site, a time the infusion set is removed, a type of port, and so forth. The artificial pancreas algorithm 416 may use one or more of these different aspects of infusion-site effectiveness as input when determining insulin doses to deliver.

The inputs to the artificial pancreas algorithm 416 may describe a variety of characteristics relevant to determining insulin doses without departing from the spirit and scope of the techniques described herein. Some additional and/or different inputs to the algorithm are also discussed further below.

As mentioned, the artificial pancreas algorithm 416 is configured to output insulin doses. The output of the artificial pancreas algorithm 416 may also be in the form of a feature vector, such that at least one of the features is indicative of an amount of insulin to deliver to the person 102 over some period of time. As mentioned above, the insulin doses output by the artificial pancreas algorithm 416 may correspond to basal dose rates and bolus doses. To this end, the output of the artificial pancreas algorithm 416 may indicate a basal rate dose, e.g., an amount of longer-acting insulin to be delivered throughout the course of the day and that may be adjusted infrequently. The output of the artificial pancreas algorithm 416 may also or alternately indicate a bolus dose, e.g., an amount of shorter-acting insulin to be delivered before and/or during a meal. The artificial pancreas algorithm 416 may generate predictions of bolus doses, for instance, responsive to user input indicating the user is about to eat a meal and/or responsive to the algorithm predicting that the user is about to eat a meal, e.g., based on a current location of the user (restaurant), recorded previous eating habits, a time of day, and so forth.

In scenarios where the artificial pancreas algorithm 416 predicts a bolus dose of insulin in anticipation of a meal, the algorithm may do so not only based on the location of the user, but also based on the glucose measurements 118 being received in real-time, such as based on rising glucose measurements 118 that indicate the person 102 has already begun eating a meal. As noted above, the artificial pancreas algorithm 416 may be configured to detect the occurrence of events that may affect the person 102's glucose as they happen. Thus, detecting that the person 102 has already begun eating a meal based on real-time data, is an example of detection of an event as it happens that may affect the person 102's glucose. Additionally, based on the location of the user and/or the person 102's glucose measurements 118, the artificial pancreas algorithm 416 may also predict the meal the person 102 is eating and predict a corresponding dose of insulin, e.g., if the person 102 is located at a pizza restaurant, then the artificial pancreas algorithm 416 may determine an insulin dose that corresponds to pizza. The ability to predict that the person 102 is eating a meal or is likely to do so soon in the future and determine a corresponding bolus dose, may be particularly useful for users that do not stringently adhere to their insulin therapy, e.g., by entering data (e.g., amount of carbohydrates) into their insulin delivery systems in anticipation of upcoming meals (e.g., 30 minutes before) or computing doses in anticipation of such meals themselves. Instead, these "non-compliant" users may often not enter such data, may not do so in a timely manner, and/or simply may not administer insulin. There may be a variety of sources of meal data, which can describe meals eaten or characteristics of meals eaten (e.g., timing, amount of food, etc.) and which can serve as input to the artificial pancreas algorithm 416 in addition to or alternately from location data.

By way of example, a "smart" refrigerator may be configured to generate and provide meal data for use by the artificial pancreas algorithm 416. Such a refrigerator may be configured to track inventory, which may include tracking food added to the refrigerator and food removed from the refrigerator. To this end, the refrigerator may generate meal data that describes food removed by the person 102 and not returned back to the refrigerator. This may be based further on receipt by the system of information describing that the user is eating the food removed from the refrigerator. Alternately or additionally, the refrigerator may be configured to suggest foods stored within the refrigerator or recipes involving foods stored within the refrigerator based on the person 102's glucose measurements, such as at a time the person interacts with the refrigerator.

By way of example, the refrigerator may detect that the person 102 has the wearable glucose monitoring device 104 and also interacts with the refrigerator, e.g., the person 102 interacts with the refrigerator controls or opens the refrigerator. Responsive to this, the refrigerator may obtain the person 102's glucose measurements 118, e.g., by downloading them from one or more of the wearable glucose monitoring device 104, the computing device 108, or the glucose monitoring platform 112. Based on the obtained glucose measurements, the refrigerator may then determine which of the foods it is maintaining (or recipes involving those foods) that, if consumed by the person 102, are predicted to achieve a desired glucose goal, such as to lower glucose if it is determined to be above a threshold or rising, to maintain glucose if it is determined to be within a desired glucose range, or to raise glucose if it is determined to be below a threshold or falling. The determined foods or recipes may then be suggested by the refrigerator, e.g., displayed on the refrigerator, communicated to the computing device 108 for display, and so forth.

As noted above, images may also be leveraged to obtain information about meals consumed by the person 102. In one or more implementations, the glucose monitoring module 408 may use image analysis to determine what the person 102 consumed during a meal by comparing a first and a second image, where the first image is taken of the meal before it is consumed by the person 102 (e.g., of a plate with the meal) and the second image is taken of the meal after it is consumed by the person 102 (e.g., of the plate without the meal and/or with any portions of the meal that were not consumed). Although this functionality is discussed in connection with the glucose monitoring module, it is to be appreciated that the image analysis, image comparisons, and determinations of amounts consumed may be performed by some other module than the glucose monitoring module 408, and the information may simply be accessible by the glucose monitoring module 408.

Regardless, a delta between the before- and after-images allows the system to calculate an actual amount that was eaten, rather than simply using the before-image which may not accurately represent an actual amount of food consumed if everything depicted in the before-image is not consumed. By more accurately determining an amount eaten due to the comparison of before- and after-images, the glucose monitoring module 408 can also more accurately determine carbohydrate and/or nutritional content of meals eaten. Further, such accurate determination of a meal allows the artificial pancreas algorithm 416 to predict a correct dose of insulin that corresponds to the food actually eaten, rather than predict a dose of insulin that is simply based on an amount of food depicted in a before-image (e.g., sitting on a plate), which again may vary from the actual amount eaten.

The glucose monitoring module 408 may process the before- and after-images to estimate an amount of carbohydrates and/or fats and determine a difference between the meal before it is eaten through completion of the meal. The artificial pancreas algorithm 416 may then predict one or more doses of insulin in relation to these determinations to cover the impact of the meal consumed (not merely pictured before eating) on the person 102's glucose. With the before- and after-images and detecting patterns of the person 102's glucose, the artificial pancreas algorithm 416 can rapidly generate a retrospective response and use the retrospective response to predict future meal glucose responses.

In addition to detecting an amount being eaten and/or the foods being eaten, in one or more implementations, the artificial pancreas system 402 may leverage one or more sensors to detect when a person 102 is eating—which can be advantageous for determining times to deliver insulin and/or rates of insulin delivery. In one example, for instance, a person may wear a wearable strain sensor that can be used to detect food consumption, i.e., whether a person is eating. A wearable strain sensor may be configured in a variety of ways without departing from the spirit or scope of the described techniques. By way of example, a wearable strain sensor may be configured as a flexible substrate (e.g., elastomer, paper, or reduced graphene oxide, to name just a few) that senses a change in shape and, responsive to sensing the change, produces a measurable electrical signal. This measurable electrical signal may be leveraged to provide the signal or a communication based on the signal to the artificial pancreas controller 406 (e.g., the insulin module 406 and/or the glucose monitoring module 408) to indicate that the user is currently eating. In other words, the wearable strain sensor can be used to generate meal data that describes times when users actually eat. The artificial pancreas algorithm 416 may then determine doses of insulin based on an actual times users are eating rather than other times, such as when users provide user input indicating they are eating (which may not match times they actually eat).

In one or more implementations, such a wearable strain sensor may be worn by the person 102 on the front of the neck to sense swallowing, on the jaw to sense chewing, or in the mouth, to name just a few. The artificial pancreas controller 404 or some component of the system 402 may include one or more machine learning models that learn to differentiate between eating and other actions that generate signals, such as talking or swallowing without eating anything. Using such machine learning models, the signals provided to the artificial pancreas algorithm 416 may be filtered such that only the signals from the wearable strain sensor that correspond to eating are received by the artificial pancreas algorithm 416.

To generate predictions of meals, the artificial pancreas algorithm 416 may also leverage historical data of the person 102 and/or the user population 110. Alternately or additionally, the artificial pancreas algorithm 416 may predict these upcoming meals and corresponding bolus doses using a current time and confidence intervals, where those intervals are built around when the person 102 has eaten historically. The artificial pancreas algorithm 416 may also predict the person 102's common meal based on the historical data, e.g., to determine a dose that corresponds to the predicted meal. In one or more implementations, for instance, the artificial pancreas algorithm 416 may predict that a meal is upcoming based on a current time and determine an average bolus dose, such as an average bolus dose for breakfast, lunch, dinner, or a snack. In addition or alternatively, the artificial pancreas algorithm 416 may predict that a meal is upcoming based on a current time and historical meal times, but the artificial pancreas algorithm 416 may wait to cause insulin delivery until early signs of a meal being eaten by the person 102 are detected. In this way, the artificial pancreas algorithm 416 may deliver insulin earlier than an algorithm that relies solely on current event detection. In particular, the artificial pancreas algorithm 416 may use these signals—historical meal times along with an early sign of a meal being eaten such as a slight increase in glucose—to provide an earlier indication that a meal is being eaten than a slight increase in glucose alone.

In addition to predicting upcoming meals which may result in insulin spikes and determining bolus insulin deliveries, the artificial pancreas algorithm 416 may also predict other events, such as exercise. The following scenario may correspond to another example in which the artificial pancreas algorithm 416 detects the occurrence of an event that affects the person 102's glucose as the event happens. For example, the artificial pancreas algorithm 416 may use one or more of a current location of the person 102, the glucose measurements 118 of the person 102, activity data of the person 102, and so on to predict that the person 102 is exercising or is about to exercise. To do so, the artificial pancreas algorithm 416 may have been trained, or an underlying model otherwise learned, based on data describing historical locations and activity of the person 102 along with his or her glucose measurements 118 as correlated to that other data and by using one or more machine learning techniques. The trained artificial pancreas algorithm 416 may thus be able to predict the person 102's activities (e.g., exercise) with data describing his or her current context based on learning from the historical data. Based on the predicted activity, the artificial pancreas algorithm 416 may also determine insulin doses accordingly or that consuming food (e.g., juice, candy, etc.) may be needed to raise the person 102's glucose. In scenarios where food consumption is needed, the artificial pancreas system 402 may output a recommendation to eat something, such as via a display of the computing device 108.

In accordance with the described techniques, the data input to the artificial pancreas algorithm 416 and output from it in connection with determining insulin doses is generally stored in the shared storage 410. As the artificial pancreas algorithm 416 determines insulin doses for the person 102 over time and effectiveness of these insulin doses to maintain the person 102's glucose level is monitored, e.g., based on the glucose measurements 118, the insulin module 406 may adjust the underlying model of the artificial pancreas algorithm 416 to better determine insulin doses for the person 102, such as by reinforcing (e.g., rewarding) determinations that resulted in stable glucose measurements within the target range and discouraging (e.g., penalizing) determinations that resulted in unstable measurements and/or determinations that resulted in measurements outside the target range. In this way, the artificial pancreas algorithm 416 may be configured to learn how to more often keep the person 102's glucose level within the target range and/or more stable than when the algorithm is first deployed. In one or more implementations, the underlying model may be adjusted by adjusting internal weights of the artificial pancreas algorithm 416 or by adjusting parameters of one or more functions used to implement the artificial pancreas algorithm 416. This adjusting over time, based on monitoring the results of the artificial pancreas algorithm 416's output, may be referred to as "learning" or "learning a model," where the underlying model is learned using machine learning techniques or, in short, is a machine learning model.

In any case, losing such learning may generally be undesirable. This is because it may take an amount of time (e.g., a number of doses and monitored responses) for the artificial pancreas algorithm 416 to learn how exactly the person 102's body responds to determined insulin doses. Moreover, it may be inconvenient for the artificial pancreas algorithm 416 to take that amount of time again to relearn such responses—relearning may also result in the reoccurrence of negative health events that occurred during previous learning. To this end, the artificial pancreas algorithm 416 is configured for communication to and storage by different devices, which may be used to back up the algorithm. By way of example, the computing device 108 may communicate the artificial pancreas algorithm 416 over the connection 420 to the glucose monitoring platform 112 so that it can be maintained in the storage device 120, such as in connection with a user profile of the person 102 at the glucose monitoring platform 112. Alternately or in addition, the artificial pancreas algorithm 416 may be communicated to the insulin delivery system 106 and/or a service associated with the computing device 108, such as a backup cloud-storage service. In this way, when a user begins using a new device (e.g., a new mobile phone or a new insulin delivery system) the artificial pancreas algorithm 416 can simply be transferred to the new device such that the learning is not lost. In other words, the artificial pancreas algorithm 416 may "pick up where it left off." In some use cases, one or more of the devices may be disposable, such as the insulin delivery system—some configurations are used for only three days then disposed. In these cases, relearning the underlying model or the parameters of the artificial pancreas algorithm 416 after every disposal (e.g., every three days) is simply unsuitable.

The data stored in the shared storage 410, which, among other information, includes data input to and output from the algorithm, may be communicated to other devices in a similar manner. For instance, the data of the shared storage 410 may be communicated to the glucose monitoring platform 112 for storage in the storage device 120, to the insulin delivery system 106, to remote storage associated with the computing device 108, and so forth. Accordingly, if a device fails or is replaced, the artificial pancreas algorithm 416 and/or the data stored in the shared storage 410 may simply be downloaded, e.g., from the glucose monitoring platform 112's storage device 120 or cloud storage of the computing device 108, to the new or replaced device.

Additionally, when the data of the shared storage 410 is communicated to the glucose monitoring platform 112, it may be aggregated by the data analytics platform 122 along with similar data from the user population 110 to form a massive, aggregated dataset. This dataset may be used to train a variety of machine learning models. Additionally or alternately, machine learning models may be applied to the massive dataset to identify patterns among the data. In this way, patterns in the data may be used to improve artificial pancreas systems 402, such as to improve the initial artificial pancreas algorithm 416 deployed on the person 102's computing device 108. By way of example, the glucose monitoring platform 112 may, as part of setup of the artificial pancreas system 402, communicate to the computing device 108 an artificial pancreas algorithm 416 that is trained using data from users of the user population 110 that are similar to the person 102 (according to various characteristics of person and those users as described by data).

The pump control manager 418 represents functionality to control the insulin delivery system 106 to deliver the insulin doses output by the artificial pancreas algorithm 416. By way of example, the pump control manager 418 may generate instructions, based on the artificial pancreas algorithm 416's output, that instruct the insulin delivery system 106 to deliver an amount of insulin over a time period, e.g., three insulin units (IU) immediately, 0.15 IU every hour continuously, and so forth. The pump control manager 418 may also cause these instructions to be communicated over the wireless connection 414 to the insulin delivery system 106. In addition to generating instructions based on output of the artificial pancreas algorithm 416 to control delivery of insulin doses, the pump control manager 418 is also configured to connect insulin delivery systems from different providers (e.g., different manufacturers) so that different pumps can deliver insulin according to doses determined using the artificial pancreas algorithm 416. The pump control manager 418 may connect different insulin systems using dedicated interfaces (e.g., for each different insulin delivery system or provider of them) and communicate secure payload data over the wireless connection 414, as discussed in more detail below. The pump control manager 418 may include a variety of functionality for controlling the insulin delivery system 106 to deliver insulin doses determined using the artificial pancreas algorithm 416 without departing from the spirit or scope of the described techniques.

Although illustrated as being included as part of the artificial pancreas controller 404, in one or more implementations, the insulin module 406 and the glucose monitoring module 408 may be configured as separate computing applications, such that the insulin module 406 corresponds to a first, insulin application and the glucose monitoring module 408 corresponds to a second, glucose monitoring application. Additionally or alternately, the insulin module 406 may be configured as a plug-in to the glucose monitoring module 408 when it is configured as an application. Indeed, a variety of programmatic or logical arrangements are contemplated in accordance with the described techniques. In scenarios where the insulin module 406 and the glucose monitoring module 408 are separate applications, communication of data between these modules may also be controlled by a secure communication protocol, i.e., so that payload data is communicated securely between the insulin module 406 and the glucose monitoring module 408. As noted above, the process for securing this payload data is described in more detail below.

The shared storage 410 is usable by the insulin module 406 and the glucose monitoring module 408 to securely share data, which enables insulin doses to be provided based, in part, on the glucose measurements 118 produced by the wearable glucose monitoring device 104. In one or more implementations, the shared storage 410 is optimized for fast writes. Access to the shared storage 410 may also be controlled by an application programming interface (API) (not shown), enabling internal and external data consumers to access data from the shared storage 410. Additionally or alternately, access to the shared storage 410 may be limited to applications authorized to do so based on inclusion in an application group published by the glucose monitoring platform 112, e.g., with a signing certificate. The applications included in this application group may be authorized to access the shared storage 410 by using the API and based on encryption management.

Additionally or alternatively, the shared storage 410 may include multiple databases, such as a database of the insulin module 406 and a database of the glucose monitoring module 408. These multiple databases may be considered shared storage based on access permissions granted to the other module. For example, the insulin module 406 may be granted permissions that allow it to access a portion of the glucose monitoring module 408's database and the glucose monitoring module 408 may be granted permissions that allow it to access a portion of the insulin module 406's database. The portions of the databases accessible to both modules may comprise the shared storage 410. Database manager 422 is configured to manage secure access to the shared storage 410 by different applications, such as by maintaining a database key in a private keychain of the glucose monitoring module 408. Details regarding at least one example implementation are discussed in more detail below.

Glucose monitoring system manager 424 is generally configured to manage the wearable glucose monitoring device 104. This may include, for instance, configuring the wearable glucose monitoring device 104 for use with the glucose monitoring platform 112, configuring the wearable glucose monitoring device 104 for use as part of the artificial pancreas system 402, receiving the glucose monitoring device data 214 from the wearable glucose monitoring device 104, processing the received glucose monitoring device data 214 (e.g., to extract the glucose measurements 118 from the glucose monitoring device data 214 and store them in the shared storage 410), associating the glucose monitoring device data 214 (or portions thereof) with supplemental data (e.g., data describing application usage or health-related aspects at a time corresponding to the glucose measurements), causing at least some of this supplemental data to be stored at or otherwise accessible via the shared storage 410, packaging the glucose monitoring device data 214 with the supplemental data for communication over the network 116 via the connection 420 to the glucose monitoring platform 112 and storage in the storage device 120, and so forth. The glucose monitoring system manager 424 may be configured to manage interactions involving the wearable glucose monitoring device 104 and the glucose monitoring platform 112 in connection with implementing the artificial pancreas system 402 in a variety of ways without departing from the spirit or scope of the described techniques.

Having discussed the artificial pancreas system 402 as well as its different components that are used to determine insulin doses and also to deliver them to a person without the person having to monitor his or her glucose and manually inject insulin, consider the following implementation examples.

Shared Glucose Monitoring- and Insulin-Module Storage

One example implementation of the shared storage 410 is provided in the following discussion. As mentioned above, the shared storage 410 is configured to securely share data—used in connection with delivering doses of insulin predicted to keep the person 102's glucose level within a target range—between the insulin module 406 (e.g., an insulin application) and the glucose monitoring module 408 (e.g., a glucose monitoring application).

In one or more implementations, the insulin module 406 and the glucose monitoring module 408 encrypt the shared storage 410 using an encryption library. By way of example, the insulin module 406 and the glucose monitoring module 408 use a third party encryption library to encrypt the shared storage 410, such as by using SQLCipher. Certainly, other encryption libraries, third-party and/or proprietary, may be used to encrypt the shared storage 410 without departing from the spirit or scope of the described techniques. To the extent that a SQL-based encryption library may be used, the shared storage 410 further may be configured as a shared database in various implementations, e.g., a SQLite database. The shared storage 410 may also be configured in other ways to ensure secure data storage for the insulin module 406 and the glucose monitoring module 408 in accordance with the described techniques.

To ensure security and privacy of the data stored in the shared storage 410, for instance, the shared storage 410 may be encrypted with a private key securely held in a shared keychain. By encrypting the shared storage 410 in this way, the encryption protects the data stored in the shared storage 410 from unauthorized modification, intercept or eavesdropping when on the computing device 108 and/or when one or more service providers generate an unencrypted backup of the computing device 108 to a different computing device.

Generally speaking, the shared storage 410 is configured to limit access to its data to applications (e.g., that include the insulin module 406 and/or the glucose monitoring module 408 or components thereof) that are listed in an application group. The applications listed in this application group may be controlled by the glucose monitoring platform 112, such that the glucose monitoring platform 112 publishes the application group and such that this application group lists the applications allowed to access data of the shared storage 410. In other words, the applications listed by the glucose monitoring platform 112 as part of the application group are the only applications that are allowed to access the shared storage 410—other applications are prevented from accessing the shared storage 410. In one or more implementations, this application group may include further information to control access to the shared storage 410, such as whether a listed application is allowed read and/or write access to the shared storage 410. In some scenarios, for instance, a given application may be listed as having read access to the shared storage 410, but not write access. In other scenarios, a given application may have both read and write access to the shared storage 410.

By using an application group, the computing device 108 may provide a shared document area that is only accessible to applications of the application group. Additionally, the application group may be configured such that the only applications that can join the group are applications that are published with a signing certificate of the glucose monitoring platform 112 and/or that are authorized by a developer-user of the glucose monitoring platform 112. A developer-user of the glucose monitoring platform may authorize applications to be part of the application group via a portal for forming application groups and for enabling publication with such signing certificates. In addition, the glucose monitoring module 408, namely, the database manager 422 is configured to manage an encryption key to the shared storage 410. Specifically, the database manager 422 maintains this key to the shared storage 410 in a private keychain of the glucose monitoring module 408. Accordingly, the applications in the application group have access to the above-discussed shared document area and the shared keychain. However, only applications that have the private database key can read and write to the shared storage 410.

In operation, the insulin module 406 may generate a public/private key pair during a setup process with the glucose monitoring module 408. The insulin module 406's public key is available to the glucose monitoring module 408 in the shared keychain. In various scenarios, a user may download an insulin application to the computing device 108 for use with the artificial pancreas system 402. This application may be downloaded from an application store, for example, and include the insulin module 406. During setup of such an application, the user may select to link the application with the glucose monitoring module 408.

Based on a selection to link an insulin application to the glucose monitoring module 408 and based on inclusion of this insulin application in the above-mentioned application group, the database manager 422 makes a copy of the glucose monitoring module 408's encryption key by encrypting it with the insulin application's public key and storing this encrypted version of the insulin application's public key in the shared keychain. Notably, each application in the application group has access to the shared keychain. In order to decrypt an encrypted version of a given application's public key, though, the corresponding private key is needed, and only the given application includes such a private key. Accordingly, an application in the application group is not able to decrypt the encrypted version of another application's public key—despite being included in the application group.

In scenarios where a user selects to unlink an insulin application, e.g., when switching to a different insulin application, the database manager 422 removes the encrypted key of the application from the shared keychain and rekeys the shared storage 410 to a new encrypted key. The database manager 422 then updates the encrypted key saved in the private keychain of the glucose monitoring module 408. When the shared storage 410 is accessible to the insulin module 406 and/or the glucose monitoring module 408, though, these modules may leverage a variety of data persisted in the shared storage 410 (e.g., by reading the data from or writing the data to the storage), namely, to enable doses of insulin to be delivered to the person 102 to keep glucose levels within a target range. In this context consider the following discussion of FIGS. 5-9.

Figure 5:
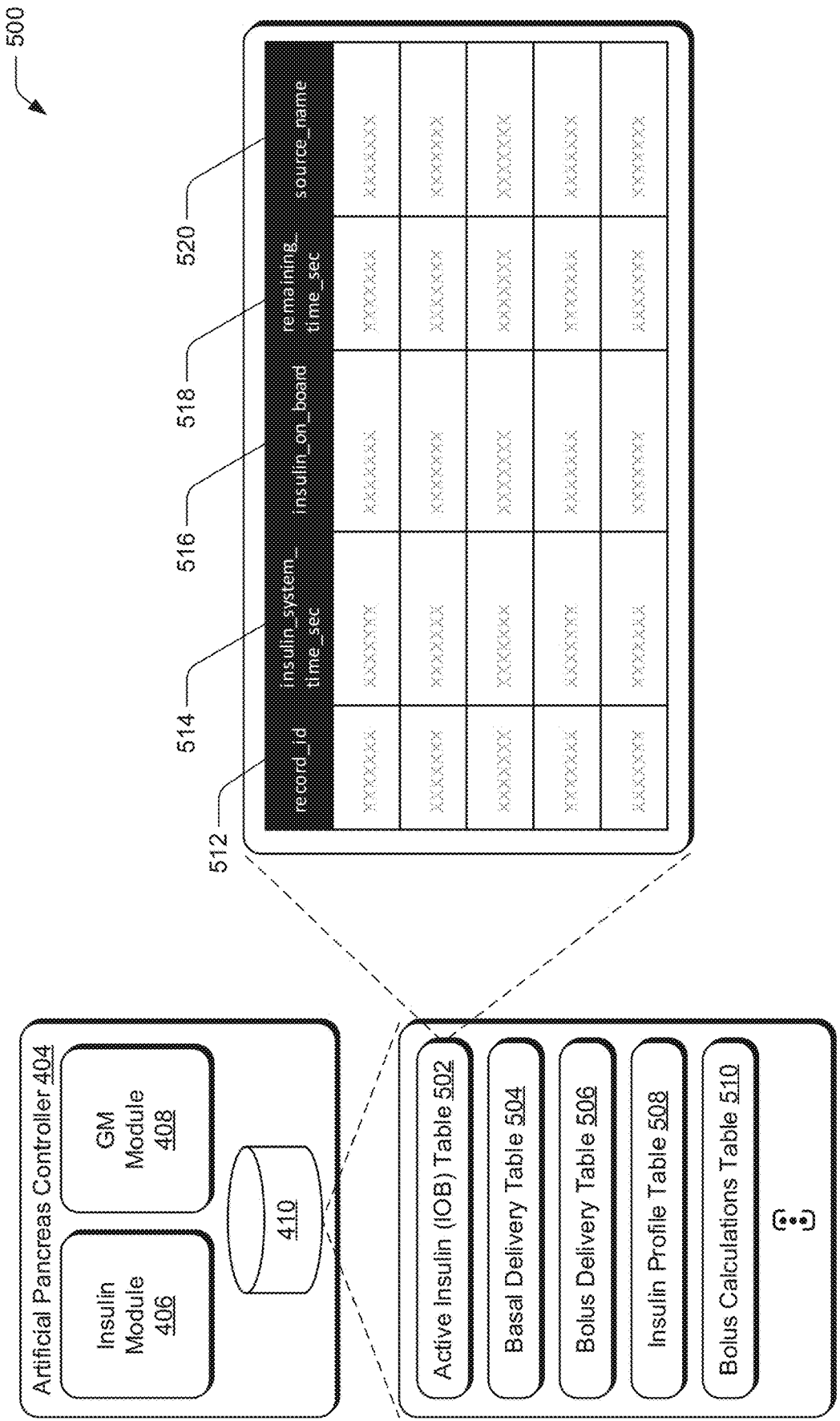
FIGS. 5-9 depict example implementations of tables stored in a shared storage in connection with implementing an artificial pancreas system.

FIGS. 5-9 depict examples of tables stored in shared storage in connection with implementing the artificial pancreas system 402. Each of these figures depicts the shared storage 410 in more detail and includes an example of a particular table. By way of example, FIG. 5 depicts an example implementation 500 of the shared storage and one example of an active insulin (insulin on board (IOB)) table. In addition to the active insulin (IOB) table 502, the illustrated example 500 also includes basal delivery table 504, bolus delivery table 506, insulin profile table 508, and bolus calculations table 510. The shared storage 410 is illustrated with ellipses to indicate that more and/or different tables may be included in the shared storage without departing from the spirit or scope of the described techniques. The basal delivery table 504, bolus delivery table 506, insulin profile table 508, and bolus calculations table 510 are discussed in detail in relation to FIGS. 6-9, respectively.

In the illustrated example 500, the active insulin (IOB) table 502 includes a plurality of columns 512-520, where each column corresponds to a different attribute of the data in the active insulin (IOB) table 502. The rows in the illustrated example—except for the topmost row—each represent a data record in the active insulin (IOB) table 502. It is to be appreciated that the active insulin (IOB) table 502 may be configured with different attributes without departing from the spirit or scope of the described techniques.

Broadly speaking, the active insulin (IOB) table 502 comprises a history of insulin on board. The table is generated while doses of insulin are being delivered, such that once the amount of insulin on board for a given bolus dose reaches zero, no more records are added to the active insulin (IOB) table 502 until delivery of a next insulin dose begins. In one or more implementations, the insulin module 406 may provide data for insulin on board measurements at an interval of time, causing the active insulin (IOB) table 502 to update with a new record according to the interval, e.g., every minute when the IOB changes. In at least some implementations, changes to insulin on board that are smaller than a threshold amount may not result in a new record being added to the active insulin (IOB) table 502, e.g., changes to insulin on board that are less than 0.1 units of insulin.

In the context of the illustrated example 500, attribute 512 represents a record identifier. For a given record in the active insulin (IOB) table 502, the record identifier uniquely identifies the record from the other records in the table. In the illustrated example 500, the attribute 512 is labeled with the name "record_id". In one or more implementations, a type of the attribute 512 may be an integer primary key. The attribute 512 thus may be configured as a primary key of a given record.

Attribute 514 represents a measurement time, e.g., a time at which a measurement is taken or otherwise determined. For a given record in the active insulin (IOB) table 502, the measurement time corresponds to a time a measurement of active insulin, i.e., the insulin on board, is determined. In the illustrated example 500, the attribute 514 is labeled with the name "insulin_system_time_sec". In one or more implementations, a type of the attribute 514 may be an integer. Further, the measurement time may correspond to Coordinated Universal Time (UTC), in seconds.

Attribute 516 represents an amount of insulin on board. For a given record in the active insulin (IOB) table 502, the amount of insulin on board corresponds to a measurement of insulin remaining on board for delivery and until there are zero units of insulin left to deliver, e.g., to the person 102. In the illustrated example 500, the attribute 516 is labeled with the name "insulin_on_board". In one or more implementations, a type of the attribute 516 may be an integer. Further, the amount of insulin on board may correspond to a number of insulin units and be measured to hundredths of an insulin unit.

Attribute 518 represents an amount of time until there will be no insulin remaining on board for a given insulin dose. This amount may be determined based upon the amount of insulin still on board (e.g., attribute 516) and also a rate of delivery of the dose. Alternately or additionally, the amount may be based on a fixed delivery end time, where the end time has been specified (e.g., according to output of the artificial pancreas algorithm 416) and the insulin delivery system 106 is instructed to deliver an entire dose of insulin by the end time. In the illustrated example 500, the attribute 518 is labeled with the name "remaining_time_sec". In one or more implementations, a type of the attribute 518 may be an integer. Further, the amount of time remaining may correspond to a number of seconds until there is no insulin remaining on board for the given insulin dose.

Attribute 520 represents a name of the source device or application corresponding to the insulin on board measurement, where "corresponding" may be the device or application that requests the measurement, performing the measurement, and/or having the insulin on board that is being delivered. This name may be determined by processing a data packet or uniform resource locator (URL) message from the device or application, e.g., extracting the name from a field, or successfully decrypting the data or message using a particular key, to name just a few. In the illustrated example 500, the attribute 520 is labeled with the name "source_name". In one or more implementations, a type of the attribute 520 may be text, e.g., a text string. Further, the name of the source device or application may identify the device or application corresponding to a given record in relation to other devices or applications, such as other devices or applications that are capable of requesting the measurement, performing the measurement, and/or having insulin on board that can be delivered.

Figure 6:
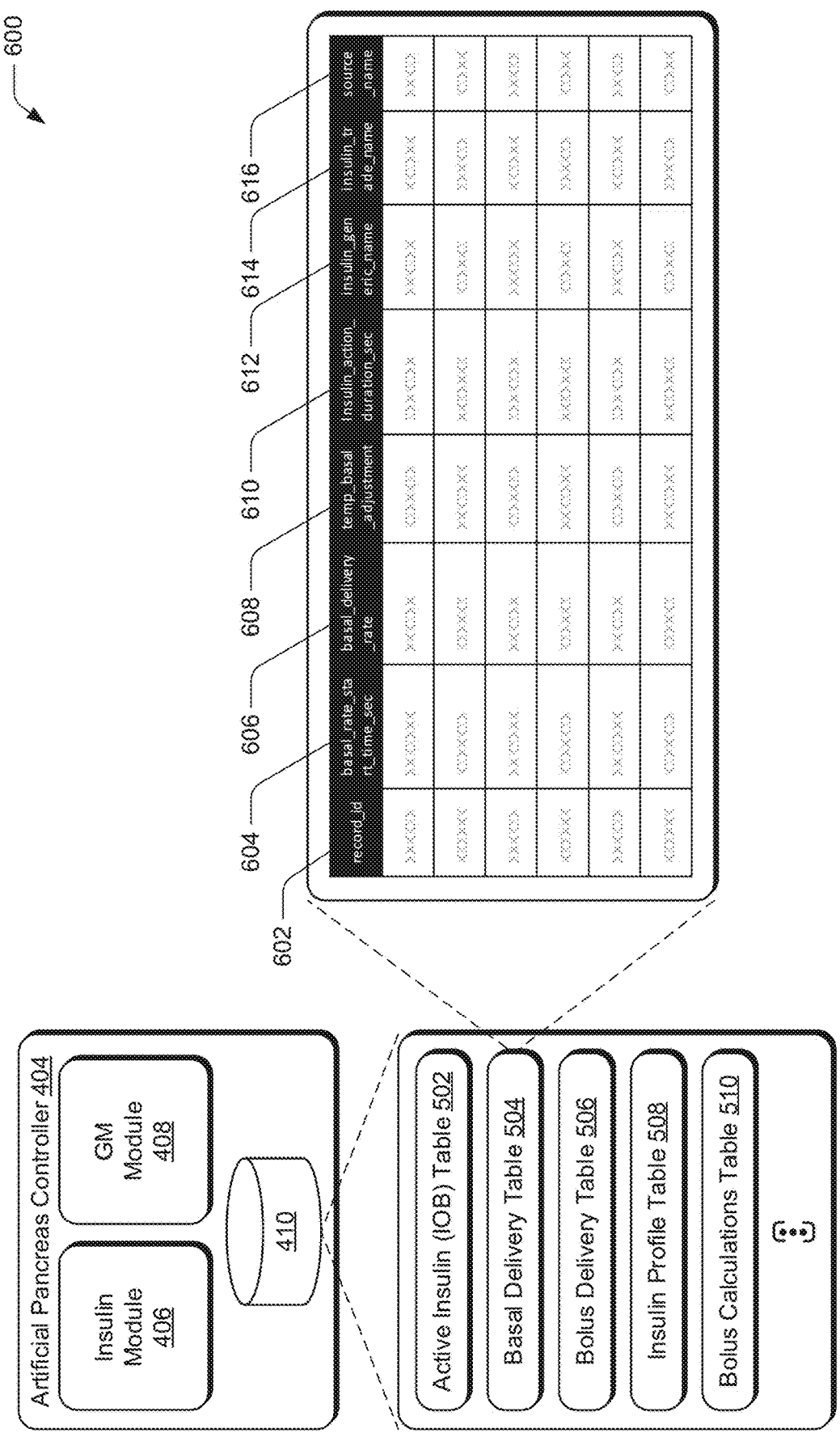

FIG. 6 depicts an example 600 of the basal delivery table 504, which includes a plurality of columns 602-616. Here, each of these columns corresponds to a different attribute of the data in the basal delivery table 504. The rows in the illustrated example 600—except for the topmost row—each represent a data record in the basal delivery table 504. It is to be appreciated that the basal delivery table 504 may be configured with different attributes without departing from the spirit or scope of the described techniques.

Broadly speaking, the basal delivery table 504 comprises a history of basal rate changes. Each time the artificial pancreas algorithm 416 determines a change to the person 102's basal rate, for instance, a new record is added to the basal delivery table 504. Examples of when a record may be added to the basal delivery table 504 include determination of and delivery according to a temporary basal rate (e.g., due to vacation, sickness, stress, time of day, exercise, etc.), suspension of insulin delivery, administration of prescription drugs, pregnancy, and changes in health metrics, to name just a few.

In the context of the illustrated example 600, attribute 602 represents a record identifier. For a given record in the basal delivery table 504, the record identifier uniquely identifies the record from other records in the table. In the illustrated example 600, the attribute 602 is labeled with the name "record_id". In one or more implementations, a type of the attribute 602 may be an integer primary key. The attribute 602 thus may be configured as a primary key of a given record.

Attribute 604 represents a time at which a basal rate of insulin delivery is changed to deliver basal insulin to the person 102 at a different rate, e.g., based on the events mentioned just above. For a given record in the basal delivery table 504, this particular time of change corresponds to a time when the basal rate, corresponding to the particular record, starts. In the illustrated example 600, the attribute 604 is labeled with the name "basal_rate_start_time_sec". In one or more implementations, a type of the attribute 604 may be an integer. Further, the delivery start time may correspond to UTC time, in seconds.

Attribute 606 describes a rate of delivery of insulin. For a given record in the basal delivery table 504, the rate of delivery corresponds to a rate to which basal insulin delivery has been changed, e.g., since the start time described by the attribute 604. Accordingly, the delivery rate described by the attribute 606 may be used until the basal rate is again changed, e.g., based on another one or more of the above-mentioned events. In the illustrated example 600, the attribute 606 is labeled with the name "basal_delivery_rate". In one or more implementations, a type of the attribute 606 may be an integer. Specifically, the integer-number indicated by the attribute 606 may describe a number of units of insulin to deliver over a predetermined amount of time, such as one hour. In this scenario, therefore, if the attribute 606 for a given record has a value of '1.00', then this may represent that the rate of delivery of basal insulin is 1.00 insulin units per hour. Moreover, the number of units of insulin to deliver per known interval of time may be specified to a known fidelity, such as to hundredths of an insulin unit. It is to be appreciated that in different implementations, the fidelity and the interval of time may be different without departing from the spirit or scope of the described techniques. For example, the attribute 606 may describe a number of units of insulin to deliver (specified to tenths of a unit) over a 24-hour period.

Attribute 608 represents how much the basal rate described by the record changes from a basal rate described by a basal profile of the person 102, such as a basal profile that is described by a record of the insulin profile table 508 and corresponds to a current time. The attribute 608 may correspond to a percentage that the rate, described by the attribute 606, is of a basal rate described by the person 102's basal profile. In this context, no change from a basal rate described by such a basal profile corresponds to one-hundred percent (100%). If the basal rate doubles from the rate indicated by the basal profile, however, then the attribute 608 may be set to a value corresponding to two-hundred percent (200%). For example, if a basal rate indicated by a basal profile is 1.00 IU/hour and a given record corresponds to a change to 2.00 IU/hour, then the attribute 608 may be set to a value corresponding to 200%. Accordingly, if the basal rate is halved from the rate indicated by the basal profile, then the attribute 608 may be set to a value corresponding to fifty percent (50%). For example, if a basal rate indicated by a basal profile is 1.00 IU/hour and a given record corresponds to a change to 0.50 IU/hour, then the attribute 608 may be set to a value corresponding to 50%.

In one or more implementations, this attribute 608 may be set to values other than one-hundred percent only when the change corresponding to the record is temporary. If, by way of contrast, the record corresponds to a rate change that also changes the basal rate described by the person 102's basal profile, then the value of this attribute 608 may be set to one-hundred percent (100%), even though the record's rate is different from a previous rate described by the person 102's basal profile. In the illustrated example 600, the attribute 608 is labeled with the name "temp_basal_adjustment". In one or more implementations, a type of the attribute 608 may be an integer. The difference between a respective record's rate and a rate described by a basal profile may be described in ways other than percentage without departing from the spirit or scope of the described techniques.

Attribute 610 represents a duration during which insulin is delivered according to the respective record's rate, e.g., the rate described by the attribute 606. For a temporary rate change, the value to which this attribute 610 is set may correspond to a time when the basal rate returns to a rate described by the person 102's basal profile. For a rate intended to be used indefinitely—a change where the rate described by the basal profile is changed—this attribute 610 may be set to a value indicative of or reserved for a rate to be used indefinitely. Alternately or additionally, this attribute 610 may be set to a value that triggers automatic computation of a new basal rate for the basal profile, given no interrupting changes. By way of example, this attribute 610 may be set to a value corresponding to one month, such that the artificial pancreas algorithm 416 automatically determines a basal rate of insulin delivery for the person every month if no other events cause the rate to be otherwise changed during that time. In the illustrated example 600, the attribute 610 is labeled with the name "insulin_action_duration_sec". In one or more implementations, a type of the attribute 610 may be an integer. Further, the duration may correspond to a number of seconds until delivery of basal insulin according to the record's rate, as described by the attribute 606, is set to change.

Attribute 612 describes a generic name of the insulin being delivered according to the record's rate. In this context, the term "generic" contrasts with a "trade" name; the term "generic" refers to an unbranded name of the type of insulin being delivered in connection with the respective record. One example of a generic name for a type of long-acting insulin is glargine, which may have trade names including Lantus®, Toujeo®, Abasaglar®, and Basaglar®. In the illustrated example 600, the attribute 612 is labeled with the name "insulin_generic_name". In one or more implementations, a type of the attribute 612 may be text, e.g., a text string of the generic name. Further, this attribute 612 and/or attribute 614 may optionally be included in the basal delivery table 504.

In contrast to the attribute 612, the attribute 614 describes a trade name (if any) of the insulin being delivered according to the record's rate. The term "trade name" refers to a branded name of a type of insulin—a branded name of a generic insulin. In the example mentioned above, for instance, Lantus®, Toujeo®, Abasaglar®, and Basaglar® are trade names of glargine—the generic name for a type of long-acting insulin which may be used for basal insulin delivery. In the illustrated example 600, the attribute 614 is labeled with the name "insulin_trade_name". In one or more implementations, a type of the attribute 614 may be text, e.g., a text string of the trade name. Like the attribute 612, this attribute 614 may be optionally included in the basal delivery table 504.

Attribute 616 represents a name of the insulin delivery system delivering the basal insulin according to the record's rate, e.g., a name of the insulin delivery system 106. This name may be determined by processing data from the insulin delivery system 106, based on setup of the artificial pancreas system 402, and so forth. In the illustrated example 600, the attribute 616 is labeled with the name "source_name". In one or more implementations, a type of the attribute 616 may be text, e.g., a text string. Further, the name of the insulin delivery system may identify the system in relation to other systems capable of delivering insulin, such as when a user changes to a different insulin system, e.g., due to insurance reasons, upgrading, use of multiple systems, and so forth.

Figure 7:
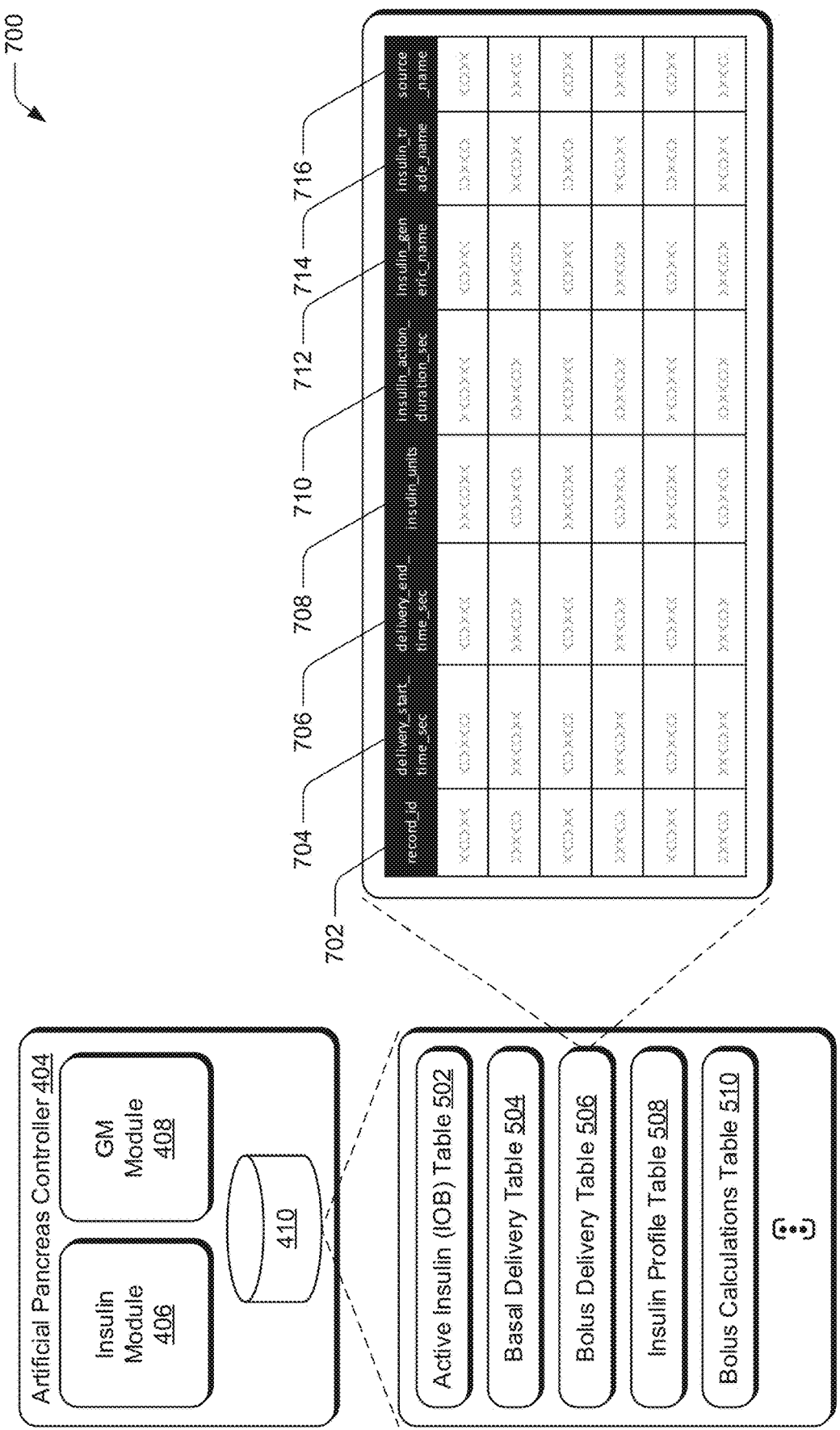

FIG. 7 depicts an example 700 of the bolus delivery table 506, which includes a plurality of columns 702-716. Here, each of these columns corresponds to a different attribute of the data in the bolus delivery table 506. The rows in the illustrated example 700—except for the topmost row—each represent a data record in the bolus delivery table 506. It is to be appreciated that the bolus delivery table 506 may be configured with different attributes without departing from the spirit or scope of the described techniques.

Broadly speaking, the bolus delivery table 506 comprises a history of insulin boluses delivered by insulin delivery systems as part of the artificial pancreas system 402. By way of example, when a bolus insulin delivery is determined by the artificial pancreas algorithm 416 and delivered in anticipation of a meal, at least one record is added to the bolus delivery table 506 describing the delivery. In one or more scenarios, multiple records may be added for split and/or combo bolus insulin doses. For instance, a number of records may be added corresponding to a number of stages of the bolus insulin delivery, e.g., two records may be added for a two-stage insulin delivery.

In the context of the illustrated example 700, attribute 702 represents a record identifier. For a given record in the bolus delivery table 506, the record identifier uniquely identifies the record from other records in the table. In the illustrated example 700, the attribute 702 is labeled with the name "record_id". In one or more implementations, a type of the attribute 702 may be an integer primary key. The attribute 702 thus may be configured as a primary key of a given record.

Attribute 704 represents a time at which delivery of a bolus dose of insulin or stage of a bolus dose corresponding to the respective record starts, e.g., responsive to entry of data describing an upcoming meal or based on the artificial pancreas algorithm 416 predicting that the person 102 is likely to eat a meal in the near future. For a given record in the bolus delivery table 506, this particular time of delivery corresponds to a time when the bolus dose or stage corresponding to the particular record starts being delivered to the person 102. This time may correspond to a determination of the respective bolus dose by the artificial pancreas algorithm 416, such that after the artificial pancreas algorithm 416 determines that a bolus dose of insulin is to be delivered based on an upcoming meal (specified by a user or predicted by the algorithm), a record is added to the bolus delivery table 506. Here, the start time described by the attribute 704 corresponds to a time the artificial pancreas algorithm 416 outputs the determination and/or a time specified in the algorithm's output. The pump control manager 418 then causes the determined dose to be delivered via the insulin delivery system 106 in accordance with the added record. In the illustrated example 700, the attribute 704 is labeled with the name "delivery_start_time_sec". In one or more implementations, a type of the attribute 704 may be an integer. Further, the delivery start time may correspond to UTC time, in seconds.

Attribute 706 represents a time at which delivery of the bolus dose of insulin or stage of the bolus dose corresponding to the respective record ends. A duration of the dose or the stage may thus be determined based on a difference between the values of the attribute 704 and the attribute 706. This time may correspond to a determination of the respective bolus dose by the artificial pancreas algorithm 416, such as described by output of the artificial pancreas algorithm 416. The artificial pancreas algorithm 416 may be configured to output a duration of the dose and/or the actual times the dose is to start and end. In the illustrated example 700, the attribute 706 is labeled with the name "delivery_end_time_sec". In one or more implementations, a type of the attribute may be an integer. Further the delivery end time may correspond to UTC time, in seconds.

Attribute 708 represents an amount of insulin to deliver for the bolus dose or stage of the bolus dose corresponding to the respective record. For a given record in the bolus delivery table 506, this amount corresponds to a determination made by the artificial pancreas algorithm 416, e.g., regarding how much insulin to deliver to the person 102 based on a user-specified meal or a predicted upcoming meal, how much to deliver for a particular stage of the dose, and so forth. In the illustrated example 700, the attribute 708 is labeled with the name "insulin_units". In one or more implementations, a type of the attribute 708 may be an integer. Further, the amount of insulin to deliver for the bolus dose may correspond to a number of insulin units to deliver between the start time specified by the attribute 704 and the end time specified by the attribute 706, and the amount may be specified in terms of insulin units and to hundredths of an insulin unit.

Attribute 710 represents a duration during which the amount of insulin described by the attribute 708 is delivered for the bolus dose or stage that corresponds to the record. This attribute 710 may be determined based on a difference between the times described by the attributes 704, 706. Alternately or additionally, the end time described by attribute 706 may be determined by adding the duration described by the attribute 710 to the start time described by the attribute 704. To this end, the artificial pancreas algorithm 416 in one or more implementations may output a prediction of a bolus dose of insulin to deliver to the person to match an upcoming or predicted upcoming meal. This prediction may include not only the amount of insulin to deliver, as described above, but also start and end times of the bolus or, alternately, a start time and a duration of delivery or simply a duration with the start time corresponding to output of the prediction. Indeed, the output of the artificial pancreas algorithm 416 may specify (e.g., in a feature vector) a variety of characteristics of a bolus dose of insulin without departing from the spirit or scope of the described techniques. In the illustrated example 700, the attribute 710 is labeled with the name "insulin_action_duration_sec". In one or more implementations, a type of the attribute 710 may be an integer. Further, the duration may correspond to a number of seconds over which an amount of bolus insulin as described by the attribute 708 is delivered to the person 102, e.g., via the insulin delivery system 106.

Attribute 712 describes a generic name of the insulin being delivered according to the previously discussed attributes of a respective record in the bolus delivery table 506. As noted above, the term "generic" contrasts with a "trade" name of insulin. One example of a generic name for a type of short-acting insulin is lispro, which may have trade names including Humalog® and Admelog®. In the illustrated example 700, the attribute 712 is labeled with the name "insulin_generic_name" In one or more implementations, a type of the attribute 712 may be text, e.g., a text string indicative of the generic name for the insulin delivered according to the record's attributes. Further, this attribute 712 and/or attribute 714 may optionally be included in the bolus delivery table 506.

In contrast to the attribute 712, the attribute 714 describes a trade name (if any) of the insulin being delivered according to the record's attributes. As noted above, the term "trade name" refers to a branded name of a type of insulin—a branded name of a generic insulin. In the example mentioned just above, for instance, Humalog® and Admelog® are trade names of lispro—the generic name for a type of short-acting insulin which may be used for bolus doses of insulin. In the illustrated example 700, the attribute 714 is labeled with the name "insulin_trade_name". In one or more implementations, a type of the attribute 714 may be text, e.g., a text string indicative of the trade name. Like the attribute 712, this attribute 714 may be optionally included in the bolus delivery table 506.

Attribute 716 represents a name of the insulin delivery system delivering the bolus dose of insulin or stage of the bolus dose according to the record's attributes, e.g., a name of the insulin delivery system 106. This name may be determined by processing data from the insulin delivery system 106, based on setup of the artificial pancreas system 402, and so forth. In the illustrated example 700, the attribute 716 is labeled with the name "source_name". In one or more implementations, a type of the attribute 716 may be text, e.g., a text string. Further, the name of the insulin delivery system may identify the system in relation to other systems capable of delivering insulin, such as when a user changes to a different insulin system, e.g., due to insurance reasons, upgrading, and so forth.

Figure 8:
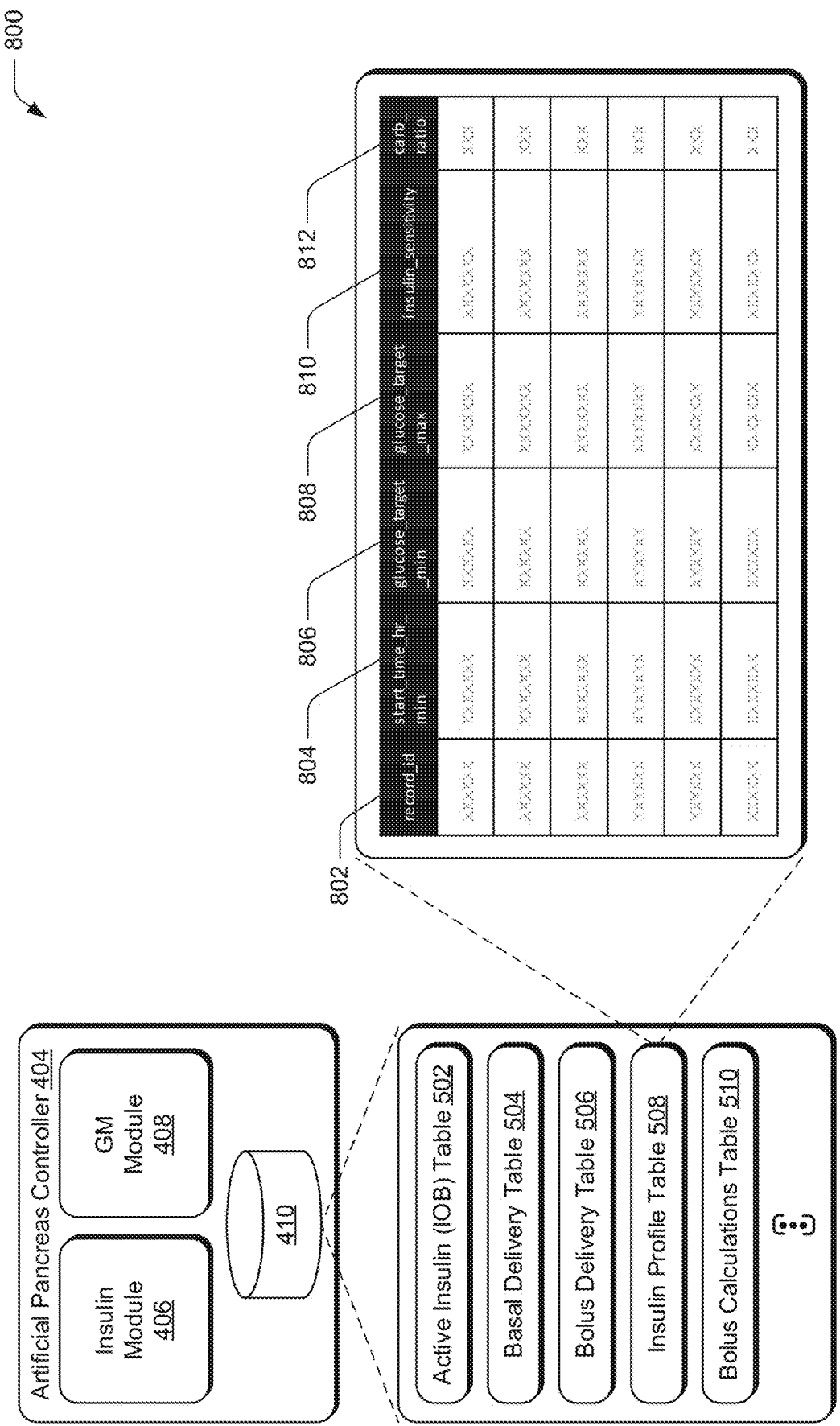

FIG. 8 depicts an example 800 of the insulin profile table 508, which includes a plurality of columns 802-812. Here, each of these columns corresponds to a different attribute of the data in the insulin profile table 508. The rows in the illustrated example 800—except for the topmost row—each represent a data record in the insulin profile table 508. It is to be appreciated that the insulin profile table 508 may be configured with different attributes without departing from the spirit or scope of the described techniques.

Broadly speaking, the insulin profile table 508 comprises a current profile of the person 102 for which the artificial pancreas system 402 is monitoring various aspects pertinent to dosing insulin, determining insulin doses, and delivering the doses according to the determinations. In one or more implementations, this profile may correspond to a selected profile of a plurality of different profiles associated with the insulin delivery system 106. The insulin profile table 508 may also comprise a history of profile changes. By way of example, when a user changes his or her insulin profile or the artificial pancreas algorithm 416 does, a record may be added to the insulin profile table 508 describing the profile according to the attributes. In the context of a user change to a profile, this may correspond to selecting a different preset profile (e.g., to "go back" to a default profile or to select a "pizza-eating" profile) or modifying a specific attribute of the profile, i.e., by changing or updating settings. Such profile changes may be based on a variety of events, such as advice from a health care provider, lifestyle changes, pregnancy, illness, improved or worsened health indicators, to name just a few. As an example of a user-specified change, the user may enter new values for a target range of glucose based on information from a health care provider, e.g., new minimum and maximum glucose levels.

The insulin profile table 508 may also be configured to account for how a user's body reacts throughout a day to eating, exercising, sleeping, insulin, and so forth. In this way, the insulin profile table 508 can account for differences in how the body reacts throughout the night (e.g., when sleeping), during mornings, afternoons, and evenings. To this end, a first record in the insulin profile table 508 may have a start time at zero (midnight) so that the insulin profile table 508 accounts for an entirety of a day. In an example where a user has a different profile for every hour of the day, e.g., 24 hours, there may be 24 records in this table. In any case, the insulin profile table 508 includes at least one record so that insulin can be delivered to the person 102 using attributes pertinent to dosing insulin.

In the context of the illustrated example 800, attribute 802 represents a record identifier. For a given record in the insulin profile table 508, the record identifier uniquely identifies the record from other records in the table. In the illustrated example 800, the attribute 802 is labeled with the name "record_id". In one or more implementations, a type of the attribute 802 may be an integer primary key. The attribute 802 thus may be configured as a primary key of a given record.

Attribute 804 represents a start time of day for the profile described by the record. In one or more implementations, profile start times can range from midnight to 11:59 PM. For a given record in the insulin profile table 508, the values of the record's attributes are thus used for calculating insulin deliveries beginning at the respective start time and until another profile having a next chronological start time becomes "active" according its respective start time. In the illustrated example 800, the attribute 804 is labeled with the name "start_time_hr_min". In one or more implementations, a type of the attribute 804 may be an integer. Further, the profile start time may be configured as having four digits, such that the first two digits correspond to an hour (e.g., 0-23) and the second two digits correspond to a minute (e.g., 0-59). Given this particular implementation, the values may range from "0000" to "2359," where "0000" corresponds to midnight, "1200" corresponds to noon, "1800" corresponds to 6:00 PM, and so forth. It is to be appreciated that various time formats may be used without departing from the spirit or scope of the described techniques.

Attribute 806 represents a target minimum glucose level for the person 102 when the respective record corresponds to the active profile. This is a level below which the artificial pancreas system 402 attempts to prevent the person 102's glucose from dropping when the respective record corresponds to the active profile. In the illustrated example 800, the attribute 806 is labeled with the name "glucose_target_min". In one or more implementations, a type of the attribute 806 may be an integer. Further, the minimum glucose level may be described in terms of milligrams per deciliter (mg/dL), such that the artificial pancreas system 402 attempts to prevent the glucose measurements 118 of the person 102 from dropping below a number of mg/dL specified by the attribute 806.

Attribute 808 represents a target maximum glucose level for the person 102 when the respective record corresponds to the active profile. This is a level above which the artificial pancreas system 402 attempts to prevent the person 102's glucose from rising when the respective record corresponds to the active profile. In the illustrated example 800, the attribute 808 is labeled with the name "glucose_target_max". In one or more implementations, a type of the attribute 808 may be an integer. Like the minimum glucose level, the maximum glucose level may also be described in terms of mg/dL, such that the artificial pancreas system 402 attempts to prevent the glucose measurements 118 of the person 102 from rising above a number of mg/dL specified by the attribute 808. It is to be appreciated that measurements other than mg/DL may be used to describe the minimum and maximum glucose levels for a time period without departing from the spirit or scope of the described techniques.

Together, the target minimum glucose level described by the attribute 806 and the target maximum glucose level described by the attribute 808 define the "target range" as discussed herein. These minimum and maximum values may be obtained in a variety of way, for example, the person 102 may enter them via a user interface (e.g., of the computing device 108 or the insulin delivery system 106) when setting up the artificial pancreas system 402 to automatically deliver insulin. In some cases, these user-entered minimums and maximums may correspond to information provided by the person 102's health care provider. Alternately or additionally, these minimums and maximums may be obtained by capturing a digital image (e.g., of a prescription or other health-care provider provided information) or may be received directly from a health care provider of the person 102, such as where a portal is exposed to the health care provider (e.g. by the glucose monitoring platform 112) and the health care provider enters the minimums and maximums via a user interface of the portal.

Attribute 810 represents an insulin sensitivity of the person 102 when the respective record corresponds to the active profile. This attribute 810 describes how the person 102's glucose changes (as indicated by the glucose measurements 118) for each insulin unit (IU) delivered. Additionally, the insulin sensitivity described by the attribute 810 may be used by the artificial pancreas algorithm 416 to compute insulin doses when the respective record corresponds to the active profile. Insulin sensitivity may be determined in accordance with the described techniques, as discussed in more detail below. In the illustrated example 800, the attribute 810 is labeled with the name "insulin_sensitivity". In one or more implementations, a type of the attribute 810 may be an integer. Further, the attribute 810 may describe the insulin sensitivity in terms of glucose change per insulin unit (e.g., mg/DL per IU).

Attribute 812 represents a carb ratio of the person 102 during time periods when the respective record corresponds to the active profile. This attribute 812 describes how many carbohydrates (in terms of a predetermined unit of measurement e.g., grams) are covered for the person 102 by a single insulin unit (IU). Here, "covered" refers to maintaining the person 102's future glucose within a target range corresponding to the attributes 806, 808. The carb ratio described by the attribute 812 may also be used by the artificial pancreas algorithm 416 to compute insulin doses when the respective record corresponds to the active profile. Carb ratio may be determined in accordance with the described techniques, as discussed in more detail below. In the illustrated example 800, the attribute 812 is labeled with the name "carb_ratio". In one or more implementations, a type of the attribute 812 may be an integer. As mentioned above, the attribute may describe the carb ratio in terms of grams of carbohydrates per insulin unit (e.g., g/IU).

The insulin profile table 508 may include a variety of additional or different attributes for determining insulin doses in accordance with the described techniques. These additional or different attributes may also be used by the artificial pancreas algorithm 416 to generate predictions of insulin doses for keeping a person's glucose within the target range. Indeed, the different or additional attributes may cause the artificial pancreas algorithm 416 to better predict insulin doses to keep a person's glucose within the target range. By "better predict" it is meant that the artificial pancreas algorithm's output insulin doses, when using the additional and/or different factors, keep the person 102's glucose within the target range more often, even within the target range keep the person 102's glucose from spiking, avoid deviations from optimal physiological responses, and so forth. One example of such an additional or different attribute may be diabetes subtype.

While diabetes is often categorized in two types, i.e., Type I and Type II diabetes, there may be a variety of subtypes under those two types, and the insulin profile table 508 may include attributes to capture the subtypes so that they can be used for prediction of insulin doses by the artificial pancreas algorithm 416. By way of example, research indicates that genetic mutations in cellular surfaces can affect insulin effectiveness. Specifically, research indicates the presence of two genetic mutations, as discussed below. Both genetic mutations can be present across persons with Type I diabetes and persons with neither Type I nor Type II diabetes. Accordingly, a person may have Type I diabetes with a first of these genetic mutations while a different person may have Type I diabetes with a second of these genetic mutations while a third person may have Type I diabetes without either genetic mutation. Thus, there may be three "subtypes" for people with Type I diabetes. However, there may only be two "subtypes" for people with Type II diabetes, since the second genetic mutation generally precludes the onset of Type II diabetes while the first genetic mutation increases susceptibility of Type II diabetes. Thus, for Type II diabetes a person may have the first genetic defect or neither of the genetic defects. These subtypes may be captured in data of the insulin profile table 508 in a variety of ways, including, for example, similar to the way different delivery types are captured in the bolus calculations table 510.

In any case, the first genetic mutation involves a marker within a genetic sequence of a person that causes a surface topology aberration on the cells of the person. This aberration in surface topology causes a reduced ability for insulin to adhere to A- and B-receptors on the cell surface. This inhibition (i.e., reduced adherence to the A- and B-receptors) reduces insulin's ability to have its generally observed effects. With this inhibition, for instance, insulin takes more time than when the mutation is not present to adhere to cellular surfaces and therefore the effect of a known volume of insulin is reduced. This inhibition may also cause insulin to take more time than when the mutation is not present to adhere to an adequate number of cells to cause a measurable effect of the insulin on glucose levels—this may be referred to as "insulin resistance."

The second genetic mutation may be considered the "opposite" of the first genetic mutation. The second genetic mutation causes a surface topology deviation in a person that allows for easier adherence of insulin to the A- and B-receptors of the person's cells than for persons without either mutation. As a result, a person with the second genetic mutation generally has a quicker cellular response (i.e., opening the cell to glucose) and also a larger population of cells that respond to insulin than persons without either mutation or having the first mutation. Not only may the artificial pancreas algorithm 416 use attributes that capture these subtypes to more accurately determine insulin doses, but the artificial pancreas algorithm 416 may also use them to identify how carbohydrate intake and exercise along with the subtype affect how much insulin to dose. The techniques described herein may also involve identifying the presence of these subtypes, such as by identifying patterns in the user population 110 of users having the subtypes, identifying that the person 102 exhibits similarities to users with one of the subtypes, and verifying that the person 102 has the identified subtype based on improved accuracy of insulin doses that account for predictions assuming the person 102 has the subtype. The subtype may also be identified in other ways such as by a health care provider or genetic testing and may thus be received as input by the artificial pancreas system 402. There may also be other subtypes accounted for in the insulin profile table 508 in addition to the ones discussed just above.

Figure 9:
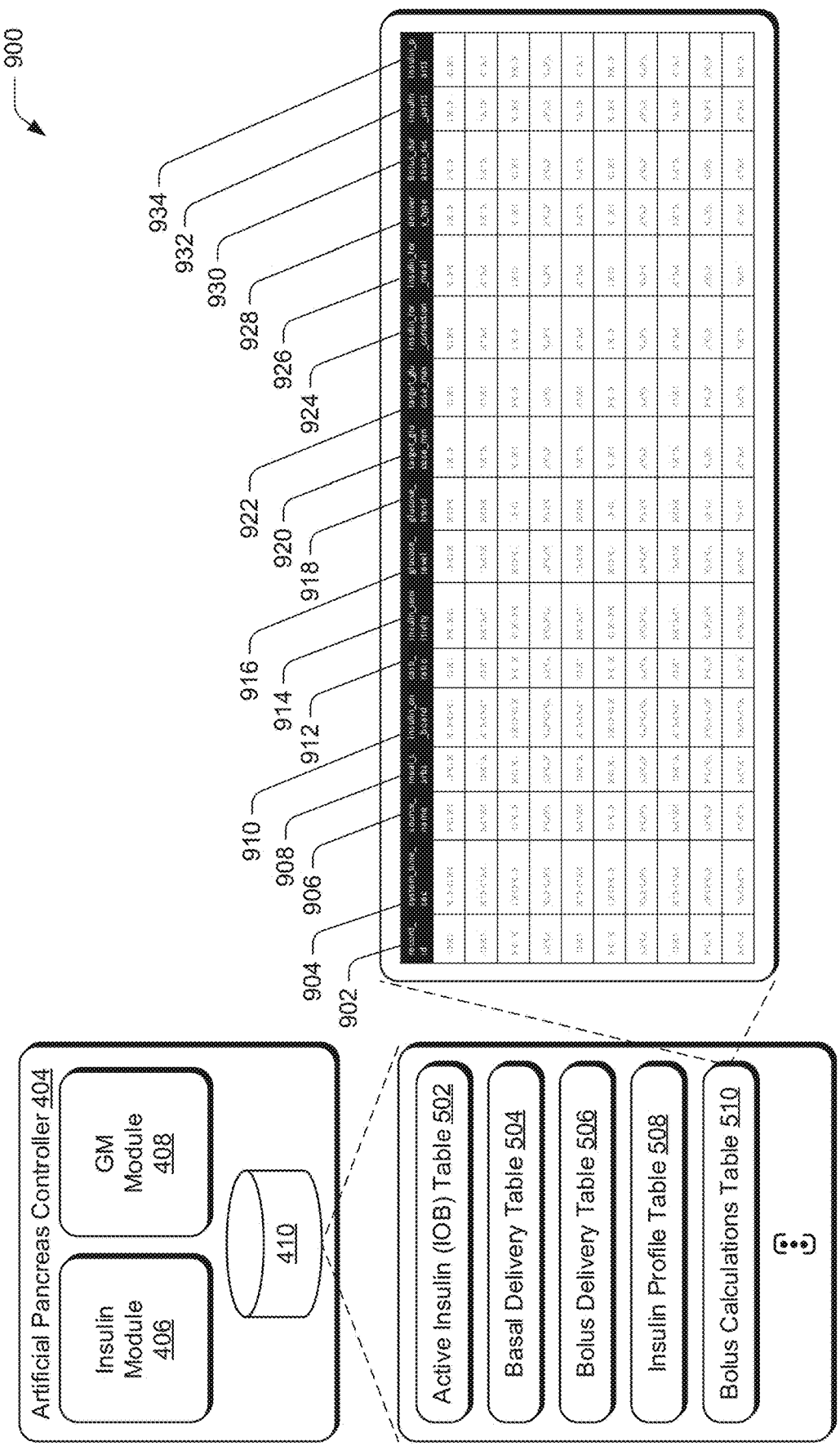

FIG. 9 depicts an example 900 of the bolus calculations table 510, which includes a plurality of columns 902-934. Here, each of these columns corresponds to a different attribute of the data in the bolus calculations table 510. The rows in the illustrated example 900—except for the topmost row—each represent a data record in the bolus calculations table 510. It is to be appreciated that the bolus calculations table 510 may be configured with different attributes without departing from the spirit or scope of the described techniques.

Broadly speaking, the bolus calculations table 510 comprises a history of bolus insulin doses computed, e.g., by the artificial pancreas algorithm 416, the glucose monitoring module 408, or the insulin delivery system 106. This contrasts with the bolus delivery table 506, which describes the bolus doses delivered, e.g., by the insulin delivery system 106. A given record in the bolus calculations table 510 describes the parameters input to calculate a bolus dose and the parameters received as output. In one or more implementations, these input parameters may be converted into a feature vector, e.g., for input to the artificial pancreas algorithm 416. Similarly, these output parameters may be converted from a feature vector to corresponding attribute values (e.g., via one or more conversion operations), where this feature vector is output by the artificial pancreas algorithm 416. Records may be added to the bolus calculations table 510 based on bolus doses being determined by any of the insulin delivery system 106, the insulin module 406 (e.g., the artificial pancreas algorithm 416), or the glucose monitoring module 408.

In the context of the illustrated example 900, attribute 902 represents a record identifier. For a given record in the bolus calculations table 510, the record identifier uniquely identifies the record from other records in the table. In the illustrated example 900, the attribute 902 is labeled with the name "record_id". In one or more implementations, a type of the attribute 902 may be an integer primary key. The attribute 902 thus may be configured as a primary key of a given record.

Attribute 904 represents a time at which a calculation is performed. For a given record in the bolus calculations table 510, the time of the calculation may correspond to a time at which a bolus dose of insulin is determined, e.g., by the artificial pancreas algorithm 416. In the illustrated example 900, the attribute 904 is labeled with the name "system_time_sec". In one or more implementations, a type of the attribute 904 may be an integer. Further, the time of the calculation may correspond to UTC, in seconds.

Attribute 906 represents a name of the source device or application corresponding to the bolus calculation, where "corresponding" refers to the device or application determining the bolus dose. In the illustrated example 900, the attribute 906 is labeled with the name "source_name". In one or more implementations, a type of the attribute 906 may be text, e.g., a text string. Further, the name of the source device or application may identify the device or application corresponding to a given record and so as to identify the device or application from other devices or applications, such as other devices or applications capable of performing the calculation.

Attribute 908 represents an amount of carbohydrates for which the bolus dose corresponding to a respective record is computed. For a given record in the bolus calculations table 510, this is the amount of carbs that the computed dose of insulin is predicted to cover for an upcoming meal—to maintain the person 102's future glucose level within the target range. As noted above and below, this amount of carbohydrates may be received via one or more user interfaces or predicted by the artificial pancreas algorithm 416. Further, this amount of carbohydrates is used by the artificial pancreas algorithm 416 to compute a corresponding dose of insulin. In other words, the amount of carbohydrates of an upcoming meal may be an input to the artificial pancreas algorithm 416 to compute an insulin dose. In the illustrated example 900, the attribute 908 is labeled with the name "meal_carbs". In one or more implementations, a type of the attribute 908 may be an integer. Further, the amount of carbs of the meal may be described in terms of grams of carbohydrates, such that the attribute describes a number of grams of carbohydrates in the upcoming meal. It is to be appreciated that this number of grams may be measured (e.g., on a scale) by a user and then provided as input, estimated based on a picture of the meal, and so forth.

Attribute 910 represents an amount of insulin on board. For a given record in the bolus calculations table 510, the amount of insulin on board corresponds to a measurement of insulin remaining on board for delivery until there are zero units of insulin left to deliver, e.g., to the person 102. In the illustrated example 900, the attribute 910 is labeled with the name "insulin_on_board". In one or more implementations, a type of the attribute 910 may be an integer. Further, the amount of insulin on board may correspond to a number of insulin units on board (e.g., the insulin delivery system 106) for delivery to the person 102 and also may be specified in terms of insulin units and measured to hundredths of an insulin unit. Additionally, a measurement of the insulin on board may be requested in connection with computation of a bolus dose by the artificial pancreas algorithm 416, such that a record is added to the active insulin (IOB) table 502 based on the computation of the bolus dose and such that the attribute 910 corresponds to the attribute 516 of the active insulin (IOB) table 502.

Attribute 912 represents a carb ratio of the person 102 at a time when the bolus dose is determined. The carb ratio may be determined by referencing the insulin profile table 508, such as by determining which record of the insulin profile table 508 corresponds to the "active" profile at a time the bolus dose is being determined and by extracting the carb ratio (e.g., the attribute 812) from the record that corresponds to the active profile. As mentioned above, this attribute describes how many carbohydrates (e.g., in terms of grams) are covered for the person 102 by a single insulin unit (IU). The carb ratio described by the attribute 912 may thus be used by the artificial pancreas algorithm 416 as an input to compute a bolus insulin dose. In the illustrated example 900, the attribute 912 is labeled with the name "carb_ratio". In one or more implementations, a type of the attribute 912 may be an integer. This attribute 912 may describe the carb ratio in terms of grams of carbohydrates per insulin unit (e.g., g/IU).

Attribute 914 represents an insulin sensitivity of the person 102 at a time when the bolus dose is determined. The insulin sensitivity may be determined by referencing the insulin profile table 508, such as by determining which record of the insulin profile table 508 corresponds to the "active" profile at a time the bolus dose is computed and by extracting the insulin sensitivity (e.g., the attribute 810) from the record that corresponds to the active profile. As mentioned above, this attribute 914 describes how the person 102's glucose changes (as indicated by the glucose measurements 118) for each insulin unit (IU) delivered. The insulin sensitivity described by the attribute 914 may thus be used by the artificial pancreas algorithm 416 as input to determine a bolus insulin dose. In the illustrated example

900, the attribute 914 is labeled with the name "insulin_sensitivity". In one or more implementations, a type of the attribute 914 may be an integer. Further, the attribute 914 may describe the insulin sensitivity in terms of glucose change per insulin unit (e.g., mg/DL per IU).

Attribute 916 represents a level of glucose at a time when the bolus dose is determined, such as a current level of glucose of the person 102. For a given record in the bolus calculations table 510, for instance, the attribute 916 may correspond to a glucose measurement 118 received from the wearable glucose monitoring device 104, e.g., a most-recently received measurement, a measurement requested in connection with computation of the bolus insulin dose, and so forth. Additionally or alternately, the level of glucose may correspond to one or more glucose measurements 118 received from the wearable glucose monitoring device 104, such as an average (e.g., mean or median) glucose measurement computed by the glucose monitoring module 408 and/or the insulin module 406. The level of glucose described by the attribute 916 may also be used by the artificial pancreas algorithm 416 as input to determine a bolus insulin dose. In the example 900, the attribute 916 is labeled with the name "glucose_level". In one or more implementations, a type of the attribute 916 may be an integer. Further, the level of glucose may be described in terms of milligrams per deciliter (mg/DL).

Attribute 918 represents a trend of glucose measurements at a time when the bolus dose is determined, such as a current trend in glucose measurements 118 of the person 102 over some amount of time before the bolus dose is determined, e.g., a trend in glucose measurements 118 of the person over a last half hour. For a given record in the bolus calculations table 510, for instance, the attribute 916 may be determined based on multiple glucose measurements 118 received from the wearable glucose monitoring device 104 over the amount of time. It is to be appreciated that the amount of time may vary without departing from the spirit or scope of the techniques, including, for instance, a predetermined amount of time (e.g., a last 5 hours, a last half hour, or a last minute), an amount of time since a last dose of insulin, a last glucose measurement, and so forth. The trend of glucose measurements described by the attribute 918 may also be used by the artificial pancreas algorithm 416 as input to compute a bolus insulin dose. In the illustrated example 900, the attribute 918 is labeled with the name "glucose_trend". In one or more implementations, a type of the attribute 918 may be an integer. Further, the trend of glucose measurements may be described in terms of milligrams per deciliter per minute (e.g., mg/dL/min).

Attribute 920 represents a target minimum glucose level for the person 102 at a time when the bolus dose is determined. The target minimum glucose level may be determined by referencing the insulin profile table 508, such as by determining which record of the insulin profile table 508 corresponds to the "active" profile at a time the bolus dose is determined and by extracting the target minimum glucose level (e.g., the attribute 806) from the record that corresponds to the active profile. As mentioned above, this attribute 920 describes a level below which the artificial pancreas system 402 attempts to prevent the person 102's glucose from dropping. The target minimum glucose level described by the attribute 920 may thus be used by the artificial pancreas algorithm 416 as input to determine a bolus insulin dose. In the illustrated example 900, the attribute 920 is labeled with the name "target_glucose_min". In one or more implementations, a type of the attribute 920 may be an integer. Further, the minimum glucose level may be described in terms of milligrams per deciliter (mg/dL), such that the artificial pancreas system 402 attempts to prevent the glucose measurements 118 of the person 102 from dropping below a number of mg/dL specified by the attribute 920.

Attribute 922 represents a target maximum glucose level for the person 102 at a time when the bolus dose is determined. The target maximum glucose level may be determined by referencing the insulin profile table 508, such as by determining which record of the insulin profile table 508 corresponds to the "active" profile at a time the bolus dose is determined and by extracting the target maximum glucose level (e.g., the attribute 808) from the record that corresponds to the active profile. As mentioned above, this attribute 922 describes a level above which the artificial pancreas system 402 attempts to prevent the person 102's glucose from rising. The target maximum glucose level described by the attribute 922 may thus be used by the artificial pancreas algorithm 416 as input to compute a bolus insulin dose. In the illustrated example 900, the attribute 922 is labeled with the name "target_glucose_max". In one or more implementations, a type of the attribute 922 may be an integer. Like the minimum glucose level, the maximum glucose level may also be described in terms of mg/dL, such that the artificial pancreas system 402 attempts to prevent the glucose measurements 118 of the person 102 from rising above a number of mg/dL specified by the attribute 922. It is to be appreciated that measurements other than mg/DL may be used to describe the minimum and maximum glucose levels without departing from the spirit or scope of the described techniques.

In one or more implementations, one or more of the attributes 908-922 may be used as inputs for determining a bolus dose of insulin. These attributes may thus be provided as input to the artificial pancreas algorithm 416 for determining a bolus insulin dose. By way of contrast, one or more of the attributes 924-934, described in detail below, may correspond to output of the artificial pancreas algorithm 416. Such outputs may be used to generate instructions for controlling insulin deliveries to the person 102 via the insulin delivery system 106. Specifically, the pump control manager 418 may control the insulin delivery system 106 to deliver insulin in accordance with the output described by the attributes 924-934, such as by using a request requesting bolus delivery as described in more detail below.

In one or more implementations, the attributes 908-922 may be processed and converted into a feature vector for input to the artificial pancreas algorithm 416. By way of example, this processing may include normalizing one or more of the attributes so that the attributes have numerical values ranging from zero to one, e.g., using min max feature scaling or other techniques. Similarly, the artificial pancreas algorithm 416 may output a feature vector, which may be processed to convert the values of the features to obtain respective values for the attributes 924-934, e.g., using one or more post-processing operations. It is also to be appreciated that the input and the output may correspond to different attributes without departing from the spirit or scope of the described techniques, such as to include an attribute indicative of predicted glucose absent correction with insulin, diabetes subtypes, and so forth. In the context of "output" attributes, consider the following discussion.

Attribute 924 represents an amount of insulin to deliver for the bolus dose or stage of the bolus dose corresponding to the respective record and, specifically, corresponds to an amount of insulin predicted to correct the person 102's glucose level so that it remains in or is adjusted back into the target glucose range as defined by the attributes 920, 922. The amount of insulin described by the attribute 924 may be obtained from output of the artificial pancreas algorithm 416, such that the value of this attribute 924 is set in the bolus calculations table 510, in part, by processing the algorithm's output. In the illustrated example 900, the attribute 924 is labeled with the name "insulin_for_correction". In one or more implementations, a type of the attribute 924 may be an integer. Further, the amount of insulin predicted to correct the person 102's insulin may be described in terms of insulin units and specified to hundredths of an insulin unit. The pump control manager 418 may thus control the insulin delivery system 106 to deliver a bolus dose of insulin including the amount of insulin for correction.

Attribute 926 represents an amount of insulin to deliver for the bolus dose or stage of the bolus dose corresponding to the respective record and, specifically, corresponds to an amount predicted to match a meal that is eaten by the person 102. The amount of insulin described by the attribute 926 may also be obtained from output of the artificial pancreas algorithm 416, such that the value of this attribute 926 is set in the bolus calculations table 510, in part, by processing the algorithm's output. In the illustrated example 900, the attribute 926 is labeled with the name "insulin_for_meal". In one or more implementations, a type of the attribute 926 may be an integer. Further, the amount of insulin predicted to match the meal eaten by the person 102 may be described in terms of insulin units and specified to hundredths of an insulin unit. The pump control manager 418 may thus control the insulin delivery system 106 to deliver a bolus dose of insulin including the amount of insulin for the meal. It is to be appreciated that output of the artificial pancreas algorithm 416 may indicate amounts of insulin to deliver for both correction and a meal. In such scenarios, the output may indicate an amount of zero if no insulin is to be delivered for the particular purpose, e.g., correction or a meal. By way of example, if bolus insulin is to be delivered for correction but not a meal, the output of the artificial pancreas algorithm 416 may indicate a particular amount for correction and zero for an amount to match a meal.

Attribute 928 indicates a type of insulin delivery, such as whether the bolus dose is to be delivered as a "normal", "extended", "combo", or "split" delivery. There may be more types of deliveries without departing from the spirit or scope of the described techniques. As used herein, a "normal" bolus delivery refers to a single, immediate dose of insulin with no extended portion. This type of bolus may be used to cover food intake or to correct high glucose levels. Broadly speaking, a "normal" bolus delivery is used for normal meals of carbohydrates, fat, and protein, e.g., meat with potatoes and vegetables. However, "normal" bolus deliveries generally do not work for meals with high fat content, since fat delays the absorption of carbohydrates into the blood stream. Examples of these non-normal, high-fat-content meals include pizza, lasagna, and tiramisu, to name just a few. To cover such meals and various eating formats (e.g., grazing or buffets), other types of bolus deliveries may be used. As used herein, an "extended" bolus delivery refers to delivery of small quantities of insulin over a period of time that is extended in relation to a normal bolus. An extended delivery may also be referred to as a "delayed" bolus. As used herein, a "combo" bolus refers to a combination of "normal" and "extended" boluses. In a combo bolus delivery of insulin, a normal bolus may be delivered and then followed with an extended bolus, e.g., when glucose measurements are high before a meal or when grazing at a buffet or cocktail party. As used herein a "split" bolus refers to delivering multiple, immediate doses of insulin with no extended portions. By way of example, a split bolus may involve delivering two normal bolus doses some amount of time apart, two single doses which include one of fast-acting insulin just before a meal and then a second dose three hours after the meal. Split doses may be split in various ways, such as 50/50 (e.g., 50% in the first delivery and 50% in the second delivery), 60/40, and so forth. The type of delivery described by the attribute 928 may be obtained from output of the artificial pancreas algorithm 416, such that the value of this attribute 924 is set in the bolus calculations table 510, in part, by processing the algorithm's output.

In one or more implementations, these different delivery types may be represented in the bolus calculations table 510 by unique values. By way of example, a "1" may represent a "normal" bolus delivery, a "2" may represent an "extended" delivery, a "3" may represent a "combo" delivery, and a "4" may represent a "split" delivery. In one or more implementations, a "0" may represent that no bolus delivery is in progress. In the illustrated example 900, the attribute 928 is labeled with the name "delivery_type". In one or more implementations, a type of the attribute 928 may be an integer, and may be limited to values that correspond to the different delivery types available, e.g., as determined by the artificial pancreas algorithm 416 and/or the types of deliveries the insulin delivery system 106 is capable of delivering.

Attribute 930 represents a duration during which the amount of insulin described by the attributes 924, 926 is delivered for the bolus dose or stage of the bolus dose that corresponds to the record. The duration of the delivery described by the attribute 930 may be obtained from output of the artificial pancreas algorithm 416, such that the value of this attribute 930 is set in the bolus calculations table 510, in part, by processing the algorithm's output. In the illustrated example 900, the attribute 930 is labeled with the name "bolus_duration_sec". In one or more implementations, a type of the attribute 930 may be an integer. Further, the duration may correspond to a number of seconds during which an amount of bolus insulin as described by the attributes 924, 926 is delivered to the person 102, e.g., via the insulin delivery system 106.

Attribute 932 represents an amount of insulin to deliver for a first stage of a bolus dose, e.g., when the type of delivery is a combo or split dose according to the attribute 928. The amount of insulin described by the attribute 932 may be obtained from output of the artificial pancreas algorithm 416, such that the value of this attribute 932 is set in the bolus calculations table 510, in part, by processing the algorithm's output. In the illustrated example 900, the attribute 932 is labeled with the name "insulin_part1". In one or more implementations, a type of the attribute 932 may be an integer. The amount of insulin designated for the first stage of the bolus dose may be described in terms of insulin units and specified to a hundredth of a unit. The pump control manager 418 may thus control the insulin delivery system 106 to deliver a first stage of a bolus dose according to the amount specified by the attribute 932.

Attribute 934 represents an amount of insulin to deliver for a second stage of a bolus dose, e.g., when the type of delivery is a combo or split dose according to the attribute 928. The amount of insulin described by the attribute 934 may also be obtained from output of the artificial pancreas algorithm 416, such that the value of this attribute 934 is set in the bolus calculations table 510, in part, by processing the algorithm's output. In the illustrated example 900, the attribute 934 is labeled with the name "insulin_part2". In one or more implementations, a type of the attribute 934 may be an integer. The amount of insulin designated for the second stage of the bolus dose may be described in terms of insulin units and specified to a hundredth of a unit. The pump control manager 418 may thus control the insulin delivery system 106 to deliver a second stage of a bolus dose according to the amount specified by the attribute 934. It is to be appreciated that insulin doses may include more stages, and, therefore, attributes for more dose "parts" may be added to the bolus calculations table 510 without departing from the spirit or scope of the described techniques.

Having discussed example tables that may be maintained in the shared storage 410 in connection with implementing the artificial pancreas system 402, consider now a discussion of how the insulin module 406 and the glucose monitoring module 408 may connect and interact to handle operations associated with the artificial pancreas system 402.

Glucose Monitoring- and Insulin-Module Linking

One example implementation of how the insulin module 406 and the glucose monitoring module 408 may connect and interact is provided in the following discussion. As noted above, the insulin module 406 and the glucose monitoring module 408 may be configured as applications, such as an insulin application and a glucose monitoring application, respectively. The insulin module 406 and the glucose monitoring module 408 may also be configured in other ways, such as part of a single application or such that portions of the insulin module (e.g., the artificial pancreas algorithm 416) are included in a same application as the glucose monitoring module 408 while other portions of the insulin module are included in a different application.

Regardless of the particular configuration, in one or more implementations, the insulin module 406 and the glucose monitoring module 408 may use uniform resource locator (URL) application linking to activate the other module in connection with sending secure payload data to that other module. Using URL application linking, the insulin module 406 and the glucose monitoring module 408 can activate the other module with a payload that includes a request and parameters, such as "show home screen," "show bolus calculator," "request bolus of 2.0 IU," and so forth. Broadly speaking, URL application linking may be used for inter-application communications, which may be communicated when either the insulin module 406 or the glucose monitoring module 408 switches to activate the other module, e.g., as a "topmost" application at the computing device 108. Such switching to activate the other module may include displaying a user interface of the switched-to module via a display of the computing device 108 and enabling user interaction via the displayed user interface.

In accordance with URL application linking as described herein, the insulin module 406 and the glucose monitoring module 408 may use public key cryptography to encrypt payload data sent to the other module via a URL. Use of public key cryptography to encrypt this payload data ensures privacy of the data exchanged between the insulin module 406 and the glucose monitoring module 408. Although public key cryptography is discussed in this example implementation, it is to be appreciated that the insulin module 406 and the glucose monitoring module 408 alternately or additionally may communicate data securely between one another using different techniques for secure communications, including blockchain technologies, for example. This secure communication along with use of the shared storage 410 may also prevent tampering by users with the insulin module 406 and the glucose monitoring module 408, including prevention of tampering with the artificial pancreas algorithm 416, e.g., tampering so that the algorithm is caused to consider user-specified data for learning or is implemented with user-supplied code. The secure communication along with use of the shared storage 410 also prevents use of unauthorized devices (e.g., unauthorized by the glucose monitoring platform 112) in the artificial pancreas system 402.

Regardless, by using public key cryptography for inter-application (or module) communication, the insulin module 406 and the glucose monitoring module 408 ensure that only the target module (e.g., the module to which a communication is communicated) is able to decrypt the payload. By ensuring that only the target module can decrypt the payload, sensitive information (e.g., personal data) is protected from intercept, including in cases where there is an unauthorized replacement of the target module, where unauthorized applications register for a same URL scheme as the modules that are permitted (e.g., by the glucose monitoring platform 112) to communicate data as part of the artificial pancreas system 402, and so forth.

To ensure the integrity and authenticity of the payload data, the module communicating payload data to the other module configures the payload to include a digital signature. In the following discussion, the module communicating the payload data may be referred to as a source module. The module intended by the source module to receive the payload data may be referred to as a target module. The digital signature included with conforming communications allows the target module to verify that the payload data is not modified or damaged during transit. Using the digital signature, the target module may also verify that the source of the payload data is a module that is allowed to send requests to the target module.

The insulin module 406 and the glucose monitoring module 408 may share public keys for such digital signatures using a shared keychain. In some scenarios, the insulin module 406 corresponds to one of a plurality of insulin applications permitted by the glucose monitoring platform 112 for use in connection with the artificial pancreas system 402. In such scenarios, each of the plurality of applications may be permitted for use in connection with the artificial pancreas system 402. This permission may be based on inclusion in a group of shared applications published by the glucose monitoring platform 112, e.g., published in a list of shared applications, in a group of them persisted in code (e.g., of the glucose monitoring module 408), in a group of them persisted in other data (e.g., a database or table included in the glucose monitoring module 408 or provided to the computing device 108 in connection with installing and/or updating the glucose monitoring module 408), or in a group of them persisted by settings, to name just a few. The published group of shared applications limits access to the shared keychain to the applications that are included in the group—only those applications published in the shared group have access to the shared keychain.

The target module may use the digital signature along with one or more additional identifiers of the source module to verify that the source module is authorized to send a data payload. By way of example, the one or more identifiers may include an identifier (e.g., a bundle_id) that can be provided to the target module by an operating system of the computing device 108, such as in connection with communication of a payload and identifying the source module. In relation to URL application linking, the target module may thus use a digital signature of a payload along with this identifier of the source module to confirm that the source module is authorized to send the communication, e.g., is authorized to send requests to the target module via URLs. By way of example, this identifier may enable the target module to retrieve the public key of the source module and the retrieved public key used to verify the digital signature provided with the payload data.

Once the target module determines that the source of a request is authorized to send such information, the operating system may switch the target module to a foreground of the operating system while suspending the source module. As noted above, these requests and their respective payloads may be sent via URL. Further, the URLs used for such switching may conform to a scheme, such as a scheme where the URL identifies the target module and optionally includes a path portion comprising a single encrypted payload. The encrypted payload included at the URL may be decrypted using the digital signature and an identifier as mentioned above and below.

With respect to obtaining the keys to implement the above-discussed shared keychain, the insulin module 406 (any one of the plurality of applications permitted to carry out the functionality of the insulin module 406) and the glucose monitoring module 408 generate a public/private key pair during a first initialization, e.g., in connection with a setup to link the modules. These modules may then cause their generated public keys to be stored in a shared keychain of the group of shared applications and also cause their generated private keys to be stored in a respective private keychain of the modules. In one or more implementations, the public keys may be identified in the shared keychain by one or more of the identifiers (e.g., bundle_id) provided by the computing device 108's operating system.

With respect to the payloads provided via URL, in one or more implementations, these payloads may include a dictionary of key value pairs with a request and parameters for the request. In accordance with the described techniques, this dictionary may be encoded in binary data, digitally signed, encrypted (e.g., with the target module's public key), and encoded into a string used as a path portion of a provided URL. In accordance with public/private keychain techniques, data encrypted with the public key of the target module may be decrypted by the target module only, because the target module alone stores the private key needed for such decryption. Other modules cannot decrypt such data, even if they were to intercept the data or eavesdrop, because they do not have the private key needed for decryption of data encrypted with the target module's public key. The digital signature provided as part of the payload thus allows the target module to both verify the integrity of the payload and also to verify its authenticity.

To generate the above discussed payloads and their respective paths, a source module of a URL communication may encode the dictionary included with the payload in binary format, such as by using an NSSecureCoding protocol. Further, the source module may append a digital signature to the binary encoding of the dictionary by computing a hash value, such as by computing a hash value that is encrypted with the private key of the source module. It is to be appreciated that a variety of hashing techniques may be used to compute such as hash value, including, for instance, the secure hash algorithm (SHA) to compute a SHA-256 value. The source module may then encrypt the combined binary data and the digital signature, e.g., using the public key of the target module. The source module may then form the path portion of the URL by encoding the encrypted combination of binary data and digital signature. For example, the source module may encode this encrypted data to a base 64 string to form the path portion of the URL.

The target module may process a received URL message in accordance with the following discussion. The target module may decode the received base 64 string comprising the path section of the URL into binary data. The target module may then separate the payload portion of the binary data from the digital signature portion of the binary data. The target module may decrypt the digital signature using the public key of the source module, e.g., obtained from the public keychain of the group of shared applications. The target module may then compare the expected hash value with a value of the decrypted digital signature to verify that the payload received is intact and also to authenticate the source module.

The following discussion describes example implementation details of the payload, including details of key/value dictionaries. As noted above, the payload sent via URL to the target module contains a dictionary of key/value pairs that has been encoded. These key/value pairs may be specific to a particular type of request directed to the target module. These key/value pairs may specify the type of request and also optionally respective parameters specific to the type of request. The different types of requests may include an initial setup screen request, a show home screen request, a show bolus calculator request, and a bolus delivery request. It is to be appreciated that the insulin module 406 and the glucose monitoring module 408 may communicate additional types of requests with one another without departing from the spirit or scope of the described techniques.

Regardless, example dictionaries encoded in connection with the above-described types of requests may be configured in accordance with the following discussion. Requests for an initial setup screen may include a dictionary with a "request" key and a "date" key. In the following discussion, a value of the "request" key generally identifies the type of request, such that a specific value for the request key identifies an initial setup screen request from a show bolus calculator request and so forth. In the context of an initial setup screen request, for instance, a value type of the request key may be a string (e.g., an NSString) and the value may correspond to a string such as "init," such that "init" identifies the request as an initial setup screen request from other types of requests. Based on receiving an initial setup screen request, the target module initiates a setup and pairing process with an insulin delivery system (e.g., the insulin delivery system 106) or with the wearable glucose monitoring device 104. A value type of the date key may be a date (e.g., NSDate) corresponding to a date and time the request is sent to the target module. In one or more implementations, the target module is configured to reject requests that are out of sequence, old, or duplicates, in terms of this date.

Requests to show home screen may be configured differently than other types of requests. By way of example, the source module may request the target module to show its home screen by configuring the URL with an empty path portion—when the path portion is empty, there is no payload. Responsive to receiving a URL with a path (payload) that is empty, the target module is configured to display its home or main screen via a display device of the computing device 108.

Requests to show bolus calculator may include a dictionary solely with a "request" key. For a show bolus calculator request, a value type of the request key may be a string (e.g., NSString) and the value may correspond to a string such as "calc," such that "calc" identifies the request as a show bolus calculator request from other types of requests. Based on receiving a show bolus calculator request, the target module causes display of its bolus calculator, e.g., via a display device of the computing device 108. The displayed bolus calculator may include user interface elements via which a user can provide input for calculating a bolus dose of insulin, e.g., a number of carbohydrates in an upcoming meal, selection of a particular meal (e.g., pizza, buffet, snack, etc.), an amount of time until an upcoming meal, and so forth. The elements may also be selectable to initiate, pause, or stop delivery of a bolus insulin dose (e.g., one computed by the artificial pancreas algorithm 416 or manually input by a user). A bolus calculator may include user interface elements for use with a variety of user actions and may also be configured to display a variety of information (e.g., glucose measurements) and visualizations (e.g., indications of trends of the glucose measurements) without departing from the spirit or scope of the described techniques.

Requests that request a bolus delivery may include a dictionary with a "request" key, a "date" key, a "carbs" key, a "meal-bolus" key, a "correction" key, a "type" key, a "duration" key, a "bolus 1" key, and "bolus2" key. For a request that requests a bolus delivery a value type of the request key may be a string and the value may correspond to a string such as "bolus," such that "bolus" identifies the request as a bolus delivery request from other types of requests. Based on receipt of a request that requests a bolus delivery, the target module causes the insulin module 406 to initiate delivery of insulin via the insulin delivery system 106—this may include employing the functionality of the pump control manager 418 to instruct the insulin delivery system 106 to deliver an insulin dose. In connection with such a request, the target module may also cause the insulin module 406 to employ the artificial pancreas algorithm 416 to compute a bolus dose of insulin and/or a basal rate of insulin. A value type of the date key for a bolus delivery request may be a date (e.g., NSDate) corresponding to a date and time the request is sent to the target module. In one or more implementations, the target module is configured to reject requests that are out of sequence, old, or duplicates, in terms of this date.

A value type of the carbs key may be a number (e.g., NSNumber) describing an amount of carbohydrates covered with the requested bolus delivery. In one or more implementations, the number may correspond to a number of grams of carbohydrates accounted for with the requested bolus delivery. This data may be obtained by the source module from the shared storage 410 to populate the bolus delivery request and/or may otherwise correspond to a record in one or more tables, such as the bolus calculations table 510. A value of the meal-bolus key may be a number (e.g., NSNumber) describing an amount of insulin to deliver to cover carbohydrates of a meal for which the bolus insulin delivery is requested. In one or more implementations, the number may correspond to a number of insulin units measured to hundredths of an insulin unit (IU). A value of the correction key may be a number (e.g., NSNumber) describing an amount of insulin to deliver to correct the person 102's glucose level so that it remains within a target range of glucose measurements. In one or more implementations, this number may also correspond to a number of insulin units measured to hundredths of an insulin unit (IU).

A value type of the "type" key may be a number (e.g., NSNumber) that indicates a type of insulin delivery, such as whether the delivery is "normal", "extended", "combo", or "split". As discussed in more detail in relation to FIG. 9, a "1" may represent a "normal" bolus delivery, a "2" may represent an "extended" delivery, a "3" may represent a "combo" delivery, and a "4" may represent a "split" delivery. It should be appreciated that the value type of the "type" key may be different yet nevertheless capture the type of bolus delivery. A type of the bolus1 key may be a number (e.g., NSNumber) describing an amount of insulin to deliver in connection with a first part of a bolus insulin delivery. This number may correspond to a number of insulin units to deliver for the first part of the delivery and be specified to hundredths of an insulin unit (IU). A type of the bolus2 key may be a number (e.g., NSNumber) describing an amount of insulin to deliver in connection with a second part of a bolus insulin delivery. The bolus2 key may be used in connection with combo or split bolus deliveries—but not with normal or extended deliveries. This number may correspond to a number of insulin units to deliver for the second part of the delivery and be specified to hundredths of an insulin unit (IU).

It is to be appreciated that the insulin module 406 and the glucose monitoring module 408 may provide different types of requests to one another without departing from the spirit or scope of the described techniques. The requests may alternately or additionally be configured in ways that are different from the above-described dictionaries and/or by using different secure communication techniques to implement the artificial pancreas system 402.

Setting Up and Adjusting Insulin Delivery

As described throughout, the artificial pancreas controller 404 is configured to utilize the artificial pancreas algorithm 416 to accurately predict the user's glucose levels as well as the insulin doses required to maintain the user's glucose levels within the target range. This allows flexibility in the user's food choices because any number of carbohydrates consumed by the user can be covered by a matching dose of insulin delivered the user by the insulin delivery system 106. In a healthy person, the pancreas produces enough insulin to keep the user's blood glucose measurements within the target range, whether the user is active, resting, eating, sick, stressed, or sleeping. This means that a healthy person can eat food at any time of day without their blood glucose levels changing dramatically. However, people with diabetes cannot produce or use insulin effectively enough to control their blood glucose levels. To solve this problem, the artificial pancreas controller 404 constantly monitors the person 102's blood glucose level based on the glucose measurements 118 provided by the wearable glucose monitoring device 104 worn by the person 102, and then controls the insulin delivery system 106 to deliver the appropriate insulin doses to the person 102, at the appropriate time, in order to maintain the person 102's blood glucose levels within the target range.

Generally, the artificial pancreas controller 404 controls the insulin delivery system 106 to deliver two types of insulin doses to the person 102: basal insulin doses and bolus insulin doses. Basal insulin doses utilize a long-acting insulin that reach the person 102's bloodstream several hours after injection and remain effective for up to 24 hours at a time, but to a lower peak than a fast-acting, intermediate-acting, or regular-acting insulin. Thus, the basal insulin dose provides a constant supply of insulin to bring down the person 102's blood glucose levels. The artificial pancreas controller 404 can be configured to control the insulin delivery system 106 to deliver basal insulin doses to a user once or twice per day in order to lower the user's blood glucose levels throughout the day. One example of a generic name for a type of long-acting insulin is glargine, which may have trade names including Lantus®, Toujeo®, Abasaglar®, and Basaglar®.

In contrast, bolus insulin doses act quickly, and thus are known as "fast-acting" or "rapid" insulin. For example, a bolus insulin dose delivered by the insulin delivery system 106 may enter the person 102's bloodstream quickly with a noticeable affect occurring within 15 minutes and peaking in about an hour. After peaking, the insulin dose begins to decrease but may continue to work for two to four hours. One example of a generic type of short-acting insulin is lispro, which may have trade names including Humalog® and Admelog®. The artificial pancreas controller 404 is configured to control the insulin delivery system 106 to deliver bolus insulin doses to the person 102 in order to match the effect of various factors which may cause the person 102's blood glucose levels to move out of the target range, such as carbohydrate consumption, exercise, stress, or sickness, to name just a few.

It is to be appreciated that the artificial pancreas algorithm 416 may be configured in a variety of ways to handle determination of both basal and bolus insulin doses. To the extent that basal and bolus doses generally apply to different types of scenarios—basal doses correspond to a longer acting form of insulin to keep glucose levels stable through periods of fasting and bolus doses correspond to a shorter acting insulin to prevent rises of glucose levels resulting from meals—determination of these different types of doses may involve consideration of different aspects of the person 102's context and thus different inputs.

In various implementations, the artificial pancreas controller 404 provides a protocol to determine an optimal basal insulin dose for a new user. Attributes corresponding to the determined basal insulin dose may then be stored in the shared storage 410 discussed above with regards to FIGS. 5-9. The process of determining the proper basal insulin dose for a new user is often referred to as "basal titration". Conventionally, basal titration is performed with a generic titration chart which includes an initial basal insulin dose, and an amount to adjust the dose over time. The use of a generic titration schedule makes it difficult to determine the optimal basal insulin dose for a new user due to concerns that an aggressive basal insulin dose may cause the user's blood glucose level to drop out of the target range and into a hypoglycemic level. As such, conventional systems initially prescribe a conservative basal insulin dose that may be injected manually by the user (e.g., using an insulin pen), and then slowly increase the basal insulin dose over time as long as hypoglycemic events are avoided. This conservative process employed by conventional systems is time consuming for the user and may take several weeks, or even months, to determine an optimal basal insulin dose for a new user. The lack of immediate results causes many patients to give up before realizing an optimal basal insulin dose.

In contrast, the techniques described herein may employ a more aggressive titration schedule because the wearable glucose monitoring device 104 can alert the person 102 before their blood glucose level drops to a hypoglycemic level. The more aggressive titration schedule enables the optimal basal insulin doses to be determined in a reduced timeframe as compared to conventional processes. Moreover, the real-time display of blood glucose levels and alerts by the wearable glucose monitoring device 104 keeps the person engaged in the process until an optimal basal insulin dose is learned by the system.

Figure 10:
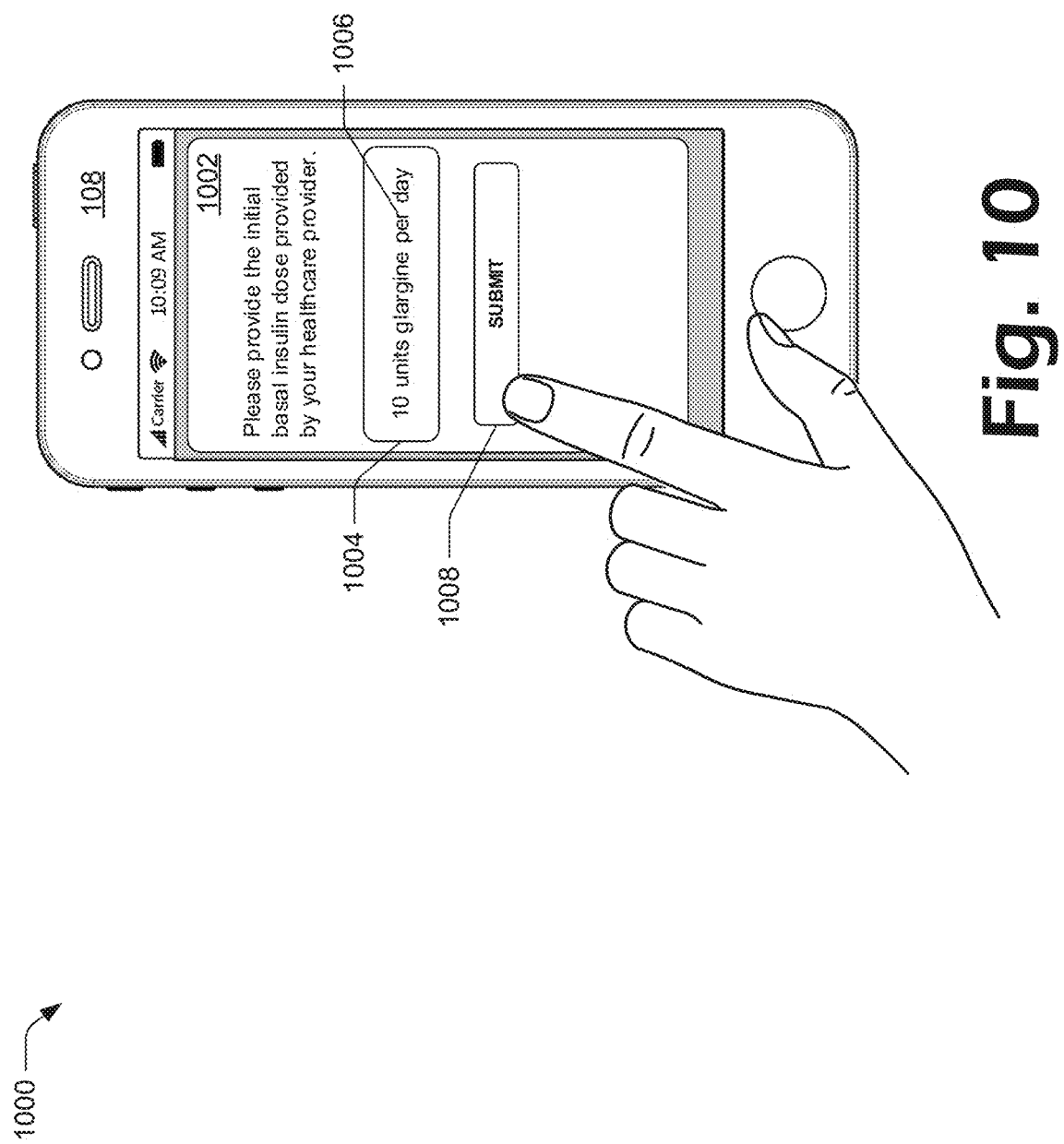
FIG. 10 depicts an example implementation of a user interface displayed for determining a basal insulin dose.

To determine the optimal basal insulin dose for a new user, the artificial pancreas controller 404 may control the computing device 108 to display a user interface configured to receive an initial basal insulin dose for the user. The initial basal insulin dose, for example, may be provided by the user's health care provider as part of an insulin prescription given to the user, and the user may then enter this dose into the user interface provided by the artificial pancreas controller 404. By way of example, consider FIG. 10 which depicts an example 1000 of a user interface displayed as part of the protocol to determine the basal insulin dose. In this example, a user interface 1002 is displayed by computing device 108. The user interface 1002 requests user input defining the initial basal insulin dose provided by the user's health care provider and includes a control 1004 to receive user input. In this example, the control 1004 is depicted as a text box control, but may be implemented as any type of control that can be used to define an initial basal insulin dose, such as a dropdown list. In example 1000, the user provides user input 1006, via the control 1004, which defines the initial basal insulin dose as 10 units of glargine per day. Responsive to user selection of a submit control 1008, the user entered basal insulin dose is stored in the shared storage 410 by the artificial pancreas controller 404.

Determining an optimal basal insulin dose may also include identifying time periods qualifying as suitable times for a basal test, e.g., one or more times at night. In one or more implementations, the insulin module 406 may monitor patterns in the person 102's glucose measurements 118 over a time period (e.g., one week) and during particular times of day (e.g., overnight). Based on this monitoring, the insulin module 406 may determine whether the person 102's basal dose is suitable, too high, or too low. Responsive to the determination, the artificial pancreas algorithm 416 may adjust the person 102's basal dose of insulin accordingly, e.g., leave the dose if suitable, lower the dose if too high, or raise the dose if too low. In one or more implementations, the monitoring may include the insulin module 406 identifying the time periods that qualify as suitable for basal tests, without providing any specific instructions to the person 102 (e.g., via display or audible output), without using information about what the person 102 eats, and/or without using information about bolus doses the person 102 has administered.

In some cases, and in order to decrease the risk of the user incorrectly entering the initial basal insulin dose prescribed by the user's healthcare provider via the user interface, the user interface 1002 may be provided to the user's health care provider instead of the user. Alternately, the artificial pancreas controller 404 may prompt the user to capture an image of the prescription written by the user's health care provider, and then leverage character recognition techniques to verify that the prescription is valid and determine the amount of the initial basal insulin dose. The artificial pancreas controller 404 may also provide prompts for the user or healthcare provider to input the time of day at which the basal insulin doses are to be delivered to the user. Notably, the initial basal insulin dose may be determined or collected in a variety of different ways without departing from the spirit or scope of the described techniques.

Regardless of how the initial basal insulin dose is obtained, the artificial pancreas controller 404 controls the insulin delivery system 106 to deliver the basal insulin dose to the user at the indicated times, such as by delivering the basal insulin dose to the user in the morning and/or at night. The artificial pancreas controller 404 can then automatically adjust the basal insulin dose delivered to the person 102 by the insulin delivery system 106 based on feedback from the wearable glucose monitoring device, e.g., the glucose measurements 118 provided by the wearable glucose monitoring device 104 worn by the person 102. For example, if after a first day the blood glucose levels of person 102 never dip close to the hypoglycemic range, but instead person 102 has various blood glucose measurements 118 near the hyperglycemic range, then the artificial pancreas controller 404 may dynamically increase the basal insulin dose the following day based on the feedback received from the wearable glucose monitoring device 104. In contrast, if after a first day the blood glucose levels of person 102 never rise close to the hyperglycemic range, but instead person 102 has various blood glucose measurements near the hypoglycemic range, then the artificial pancreas controller 404 may dynamically decrease the basal insulin dose the following day.

The artificial pancreas controller 404 may also adjust the basal insulin dose each day based on a variety of different factors, such as exercise, stress, sickness and so forth. In some cases, the basal insulin dose may also be adjusted based on the fasting glucose level of person 102 determined from the glucose measurements 118 provided by the wearable glucose monitoring device 104. For example, the artificial pancreas controller 404 may increase the basal insulin dose for person 102 when the fasting glucose level is above a "normal range," whereas the dose may be decreased on days when the fasting glucose level is below the "normal range." In any case, the process mentioned just above can be repeated each day such that the artificial pancreas controller 404 is able to quickly learn the optimal basal insulin dose for person 102, adjust this dose as needed, and deliver the optimized basal insulin doses to person 102 each day.

Moreover, once the basal insulin dose is determined for person 102, the artificial pancreas controller 404 can detect when the blood glucose level of person 102 is out of range (when no bolus insulin dose is in effect) based on the glucose measurements 118 provided by the wearable glucose monitoring device 104. In some cases, the artificial pancreas controller 404 can determine reasons for the out-of-range measurements, and indicate these reasons to person 102, such as lack of exercise, stress, or sickness. As part of this, the artificial pancreas controller 404 may also generate targeted recommendations to person 102 indicative of lifestyle changes that will help stabilize the blood glucose level within the target range, such as adjusting exercise frequency and/or intensity, reducing stress, and so forth. In cases where the blood glucose level of person 102 is out of range for an extended period of time, then the protocol to determine an optimal basal insulin dose may be repeated by the artificial pancreas controller 404.

In various implementations, the artificial pancreas controller 404 also provides protocols to determine optimal bolus insulin doses. Notably, carbohydrates and insulin affect people differently, and thus the artificial pancreas controller 404 is configured to determine the effect of carbohydrates and insulin on the blood glucose level of person 102 in order to accurately predict glucose levels and corresponding bolus doses of insulin to deliver to maintain the blood glucose level within the target range in response to various events, such as carbohydrate consumption, exercise, stress, or illness. As part of this, the artificial pancreas controller 404 employs a process to learn the carbohydrate-to-glucose ratio and insulin sensitivity factor for person 102. Attributes corresponding to the determined carbohydrate-to-glucose ratio and insulin sensitivity factor may then be stored in the shared storage 410 discussed above with regards to FIGS. 5-9.

The carbohydrate-to-glucose ratio is a measure of the effect of carbohydrates on blood glucose level. For example, using the processes described below, the artificial pancreas controller 404 can determine how much the blood glucose level of person 102 increases per one gram of carbohydrate. The insulin sensitivity factor is a measure of the effect of insulin on blood glucose level and corresponds to the drop in blood glucose levels (usually measured in mg/dL) caused by one unit of insulin. High insulin sensitivity allows the cells of the body to use blood glucose more effectively thereby reducing blood glucose levels. In contrast, low insulin sensitivity is known as insulin resistance and occurs when the user's cells do not absorb as much glucose, which might lead to excessively high blood glucose levels.

It is to be appreciated, therefore, that the carbohydrate-to-glucose ratio can be used by the artificial pancreas algorithm 416 of the artificial pancreas controller 404 to accurately predict a future glucose level a short time after carbohydrates are consumed by person 102 as long as the amount of carbohydrates consumed is identified. Then, based on the predicted future glucose level and the insulin sensitivity factor, the artificial pancreas algorithm 416 can determine the proper bolus insulin dose to deliver to in order to match the predicted rise in glucose level.

As part of the process to determine the carbohydrate-to-glucose ratio, the artificial pancreas controller 404 determines an initial glucose measurement based on the glucose measurements 118 provided by the wearable glucose monitoring device 104 worn by person 102, and obtains nutritional information describing an amount of carbohydrates to be consumed by person 102. In the context of determining the carbohydrate-to-glucose ratio, consider FIG. 11 which depicts an example 1100 of user interfaces displayed by the artificial pancreas controller as part of the process to determine the carbohydrate-to-glucose ratio for person 102. At 1102, the artificial pancreas controller 404 causes display of a user interface 1104 by the computing device 108. The user interface 1104 includes a welcome message that provides information describing the carbohydrate-to-glucose ratio. Notably, consuming additional macronutrients (e.g., protein and fat) in addition to carbohydrates may decrease the accuracy of the test, thus in this example the user interface 1104 includes a recommendation to select a food that consists mostly of carbohydrates, such as white rice.

At 1106, the artificial pancreas controller controls the user interface 1104 to display a second screen which indicates an initial blood glucose level of person 102 is 120 mg/dL, as well as a control 1108 configured to receive user input defining the amount of carbohydrates that person 102 will consume. In one or more implementations, the artificial pancreas controller 404 may ensure that the initial blood glucose measurement is within a target range, such as within 100 to 120 mg/dL before allowing the automated process to begin. For example, if it is determined that the blood glucose level is outside of the target range, the artificial pancreas controller 404 may terminate the automated process and instruct the user to try again at a later time when the blood glucose level is within range. As part of this, the artificial pancreas controller 404 may provide a recommendation to move the blood glucose levels within the target range, such as by increasing exercise, decreasing stress, and so forth.

In some cases, the artificial pancreas controller 404 can determine the carbohydrate-to-glucose ratio more accurately when a small amount of carbohydrates is consumed as part of the test (e.g., 5-10 grams of carbohydrates). Thus, at 1106 the user interface 1104 includes a recommendation to consume 10 grams of carbohydrates or less. Notably, the range of suggested carbohydrates may be based on other factors, such as the body weight or person 102. As such, the suggested amount of carbohydrates to consume may vary for different users. In some implementations, the user interface may display an additional prompt, which instructs the user to enter more detailed information, such as the type of food consumed, the weight of the consumed food (e.g., measured in grams or ounces), or the macronutrient makeup of the consumed food (e.g., amount of carbohydrates, protein, and fat). In this scenario, the artificial pancreas controller 404 may factor in the type of food and/or the amount of other macronutrients when determining the carbohydrate-to-glucose ratio.

At 1106, person 102 has provided input, via control 1108, indicating that 10 grams of carbohydrates will be consumed. At 1110, and in response to the input defining the amount of carbohydrates to be consumed, the artificial pancreas controller 404 controls the user interface 1104 to display instructions to consume the carbohydrates. The user interface 1104 also provides an indication that the blood glucose level of person 102 will be monitored and used to determine the carbohydrate-to-glucose ratio.

After determining the initial blood glucose measurement and the nutritional information describing an amount of carbohydrates to be consumed, the artificial pancreas controller 404 monitors the blood glucose level based on the glucose measurements 118 provided by the wearable glucose monitoring device 104 worn by person 102. Notably, after consuming the carbohydrates, the blood glucose measurements will increase up to a peak glucose measurement, before decreasing back downwards. In order to determine the peak glucose measurement, the artificial pancreas controller 404 may monitor the trend rate of the person's glucose measurements 118 as they increase and detect the peak glucose measurement when the trend rate decreases towards a value of 0. This is because the decrease in the trend rate indicates that the peak glucose measurement, caused by the consumption of carbohydrates, has been reached.

Once the peak glucose level is detected, the artificial pancreas controller 404 determines the carbohydrate-to-glucose ratio based on the initial glucose measurement, the peak glucose measurement, and the amount of carbohydrates consumed. For example, the carbohydrate-to-glucose ratio may be determined by dividing the number of carbohydrates (measured in grams) by the change in blood glucose measurements (e.g., the difference between the initial blood glucose measurement and the peak blood glucose measurement). In some cases, the results of the carbohydrate-to-glucose ratio is output by the artificial pancreas controller 404. By way of example, at 1112, the artificial pancreas controller 404 controls the user interface 1104 to display the determined carbohydrate-to-glucose ratio. In this example, the carbohydrate-to-glucose ratio for person 102 is determined to be 1:5, which signifies that each gram of carbohydrate consumed by person 102 will raise the blood glucose level of person 102 by 5 mg/dL. This may be determined, for example, by measuring the blood glucose level using the wearable glucose monitoring device 104 and detecting a peak glucose level of 170 mg/dL after the 10 grams of carbohydrates are consumed. Based on this, the amount of carbohydrates (10 grams) is divided by the change in glucose levels 50 mg/DL (170 mg/dL-120 mg/DL) in order to determine the carbohydrate to glucose ratio of 1:5. The carbohydrate-to-glucose ratio is stored in the shared storage 410 by the artificial pancreas controller 404 and usable by the artificial pancreas algorithm 416 to determine bolus insulin doses as described throughout.

In one or more implementations, the artificial pancreas controller 404 can determine the insulin sensitivity factor after detecting the peak glucose level as part of the automated process. For example, as depicted at 1112, the user interface 1104 may display a control that asks person 102 whether they would like to determine their insulin sensitivity factor now. If person 102 selects "yes", the artificial pancreas controller 404 may initiate the process to determine the insulin sensitivity factor. Alternately, the artificial pancreas controller 404 can determine the insulin sensitivity factor as part of a separate automated process (e.g., if person 102 selects the "no" control depicted in the user interface 1104 at 1112).

To determine the insulin sensitivity factor, the artificial pancreas controller 404 detects a peak glucose measurement, such as by detecting a leveling of the rate of increase of the glucose measurements 118 provided by the wearable glucose monitoring device 104 after carbohydrates are consumed by person 102 as part of the process to determine the carbohydrate-to-glucose ratio. Next, the artificial pancreas controller 404 estimates a bolus insulin dose that will drop the blood glucose level from the peak glucose measurement to a target glucose measurement. The artificial pancreas controller 404 may calculate a conservative estimate of the bolus insulin dose to prevent the blood glucose level from dropping too low into a hypoglycemic range. In some cases, the bolus insulin dose is estimated to cause the peak glucose measurement to drop to a target glucose measurement which corresponds to the initial glucose level of person 102. For example, if the initial blood glucose level of person 102 is 120 mg/dL and rises to a peak glucose level of 170 mg/DL, then the bolus insulin dose may be selected to return the blood glucose level to the initial level of 120 mg/dL.

The artificial pancreas controller 404 controls the insulin delivery system 106 to deliver the determined bolus insulin dose to person 102, and monitors the glucose measurements 118 provided by the wearable glucose monitoring device 104 worn by person 102—after the estimated bolus insulin dose is delivered to the person 102 via the insulin delivery system 106—to detect the target glucose measurement, corresponding to a leveling of the rate of decrease in the glucose measurements 118. The artificial pancreas controller 404 determines the insulin sensitivity factor based on an amount of insulin included in the bolus insulin dose and the difference between the peak glucose measurement and the target glucose measurement. For example, the change in the blood glucose level (from the peak glucose measurement to the base glucose measurement) may be divided by the units of insulin delivered in the bolus insulin dose. In some cases, the artificial pancreas controller 404 may include other factors when calculating the insulin sensitivity factor, such as the amount of time before the insulin started to have an effect on the blood glucose level, when the effect of the insulin peaked, and when the effect of the insulin began to drop.

Figure 12:
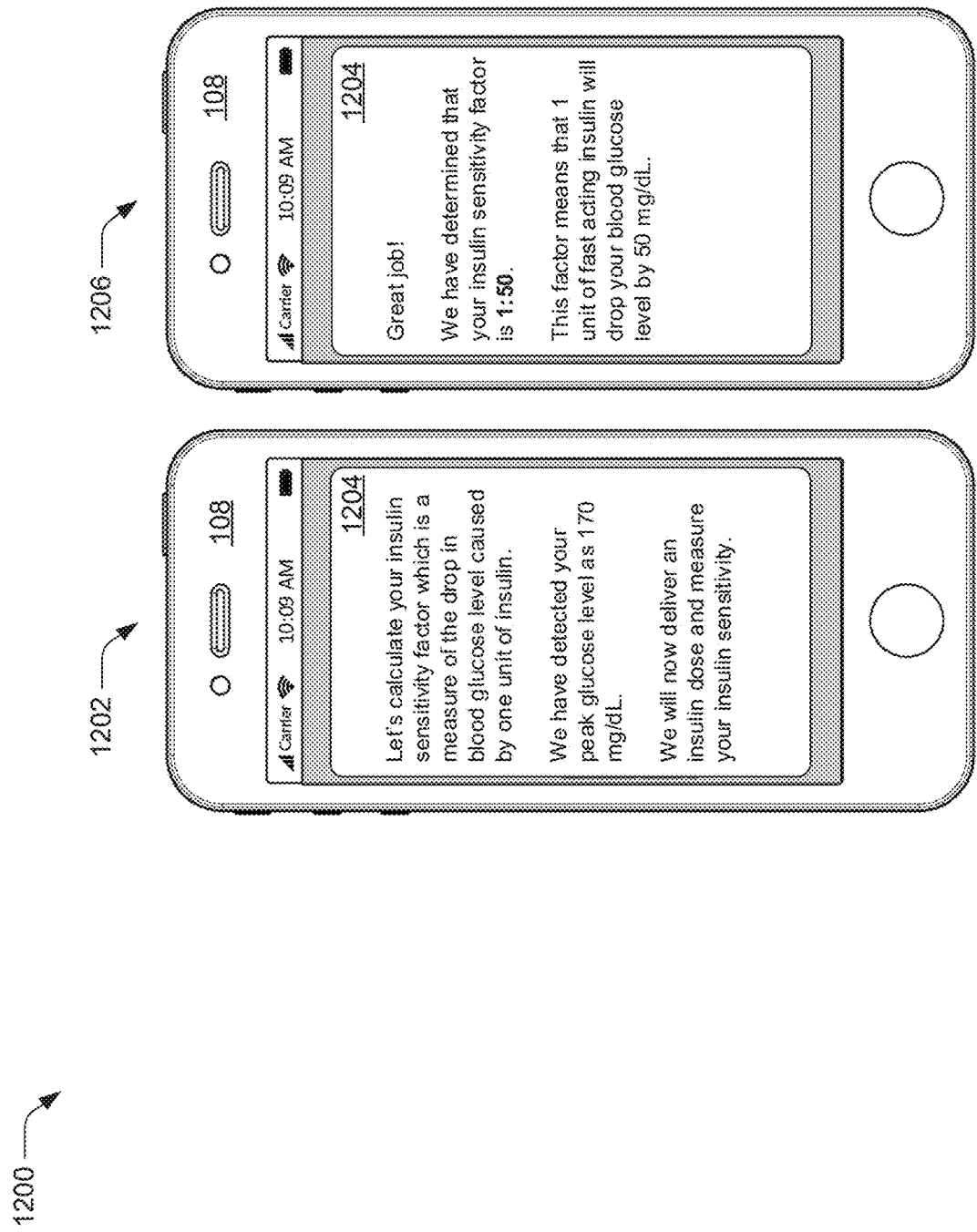
FIG. 12 depicts an example implementation of user interfaces displayed for determining insulin sensitivity of a person.

In the context of determining the insulin sensitivity factor, consider FIG. 12 which depicts an example 1200 of user interfaces displayed by the artificial pancreas controller 404 as part of the process to determine the insulin sensitivity factor for person 102. At 1202, the artificial pancreas controller 404 causes display of a user interface 1204 by the computing device 108. The user interface 1204 includes a welcome message which includes information regarding the insulin sensitivity factor and informs person 102 that a peak blood glucose level of 170 mg/dL has been detected. In addition, the user interface 1204 notifies person 102 that an insulin dose will be delivered in order to measure the insulin sensitivity factor. At 1206, the artificial pancreas controller 404 controls the user interface 1204 to display a second screen which includes an indication of the insulin sensitivity factor determined for person 102. In this example, the determined insulin sensitivity factor is 1:50 which indicates that one unit of fast acting insulin will drop the blood glucose level of person 102 by 50 mg/dL.

Notably, the process to determine the carbohydrate-to-glucose ratio and insulin sensitivity factor may be repeated multiple times by the artificial pancreas controller 404 in order to obtain the most accurate values. Additionally, the artificial pancreas controller 404 may repeat the test at different times of the day, since a person's insulin sensitivity may vary from breakfast, to lunch, to dinner, as well as based on other factors such as exercise or stress. In some cases, the test may be repeated multiple times to first confirm the results for a first meal event (e.g., breakfast), and then once confirmed, can be repeated multiple times to confirm results for other meal events, such as lunch and dinner.

The insulin sensitivity factor is stored in the shared storage 410 by the artificial pancreas controller 404 along with the carbohydrates-to-glucose ratio. Additionally, the artificial pancreas algorithm 416 may determine the carb ratio of the person 102 based on the carbohydrate-to-glucose ratio and the insulin sensitivity factor. As described throughout, the carb ratio describes how many predetermined units of measurement (e.g., grams) of carbohydrate are covered for the person 102 by a single insulin unit (IU), where "covered" refers to maintaining the person 102's glucose within a target range. The artificial pancreas algorithm 416 may access these parameters from the shared storage 410 and utilize the carbohydrate-to-glucose ratio and insulin sensitivity factor to determine the bolus insulin doses that are to be delivered to the user during the user's day to day activities. The artificial pancreas controller 404 may provide these values as part of input to the artificial pancreas algorithm 416, e.g., as values for features of input feature vectors. For example, based on the carbohydrate-to-glucose ratio, the artificial pancreas algorithm 416 can predict a peak glucose measurement for a future meal based on the initial glucose measurement of person 102 and the amount of carbohydrates to be consumed as part of the meal. Moreover, based on the insulin sensitivity factor, the artificial pancreas algorithm 416 may determine the amount of insulin to deliver via the insulin delivery system 106 in order to decrease the blood glucose level from the predicted peak glucose measurement back down to the initial glucose measurement.

While the carbohydrate-to-glucose ratio and the insulin sensitivity factor can be utilized by the artificial pancreas algorithm 416 to accurately predict the peak glucose measurement and the corresponding dose of insulin to deliver to match the expected rise in blood glucose levels when the only available information is an estimate of the amount of carbohydrates consumed, an even greater level of accuracy may be achieved by matching insulin doses to commonly consumed meals. Thus, in one or more implementations the artificial pancreas controller 404 provides an automated process to match bolus insulin doses to commonly consumed meals. To do so, the artificial pancreas controller 404 obtains information describing a meal to be consumed by person 102. This information may be obtained in a variety of different ways. In some cases, the information includes a description of the meal, along with nutritional information indicating the total amount of carbohydrates included in the meal. Alternately, the nutritional information may include additional information, such as the total amount of calories, fat, and protein. In one or more implementations, the information may include an image of the meal, from which the artificial pancreas controller 404 can estimate the amount of carbohydrates and other macronutrients. For example, person 102 may indicate that the meal is a particular type of cereal and include a picture of the bowl containing milk and cereal captured by a camera. From this, the artificial pancreas controller 404 can use various image recognition techniques to determine the amount of cereal and milk in the bowl. Based on the amount of cereal and milk estimated using the image recognition techniques, the artificial pancreas controller 404 can then determine the nutritional content of the meal (e.g., carbohydrates, protein, and fat) by accessing nutritional information for the cereal and milk from a database containing nutritional information for various food items.

Regardless of how the nutritional information for the meal is obtained, the artificial pancreas controller 404 determines a bolus insulin dose based on the nutritional information. For example, by calculating the total amount of carbohydrates for the meal based on the nutritional information, the artificial pancreas controller 404 can use the artificial pancreas algorithm 416 to predict the bolus insulin dose that will be needed to counteract the rise in blood glucose levels caused by consumption of the meal. The artificial pancreas controller 404 then controls the insulin delivery system 106 to deliver the determined bolus insulin dose to person 102. In some cases, the bolus insulin dose should be delivered 15 to 30 minutes before the meal is consumed which is the amount of time required for the insulin dose to take effect. Alternately, the ideal time to begin the meal may be determined by monitoring the effect of the insulin on the user, such as by determining when the insulin rate starts to go down. Thus, in some cases, the artificial pancreas controller 404 can monitor the effect of the insulin on the user, and then notify the user when it is time to begin consumption of the meal, such as by sending a notification to computing device 108.

After instructing the user to begin consumption of the meal, the artificial pancreas controller 404 monitors the blood glucose level based on glucose measurements 118 provided by the wearable glucose monitoring device 104 worn by person 102. The artificial pancreas controller 404 may detect the peak glucose measurement, and then monitor the glucose measurements as the blood glucose level drops from the peak glucose measurement. The artificial pancreas controller 404 detects a base glucose level when the trend rate of the decrease in blood glucose measurements nears a value of 0. The artificial pancreas controller 404 then compares the base glucose level to the initial glucose level which was measured prior to delivery of the bolus insulin dose and consumption of the meal. If the base glucose level is within a predefined error range of the initial glucose level, then the artificial pancreas controller 404 determines that the meal consumption has been matched, and the bolus insulin dose is associated with the meal information in the shared storage 410. In this way, the bolus insulin dose can be delivered to person 102 for future meals based on an indication that the particular meal is to be consumed.

Notably, if the base glucose level is not within the predefined error range, then the artificial pancreas controller 404 may generate a notification to repeat the test another time. During the next test for the meal, the artificial pancreas controller will adjust the bolus insulin dose based on the results of the previous test. This test can then be repeated multiple times until the bolus insulin dose is correctly matched to the meal. Additionally, the artificial pancreas controller 404 can be configured to provide feedback to person 102 describing how well the process is working.

Figure 13:
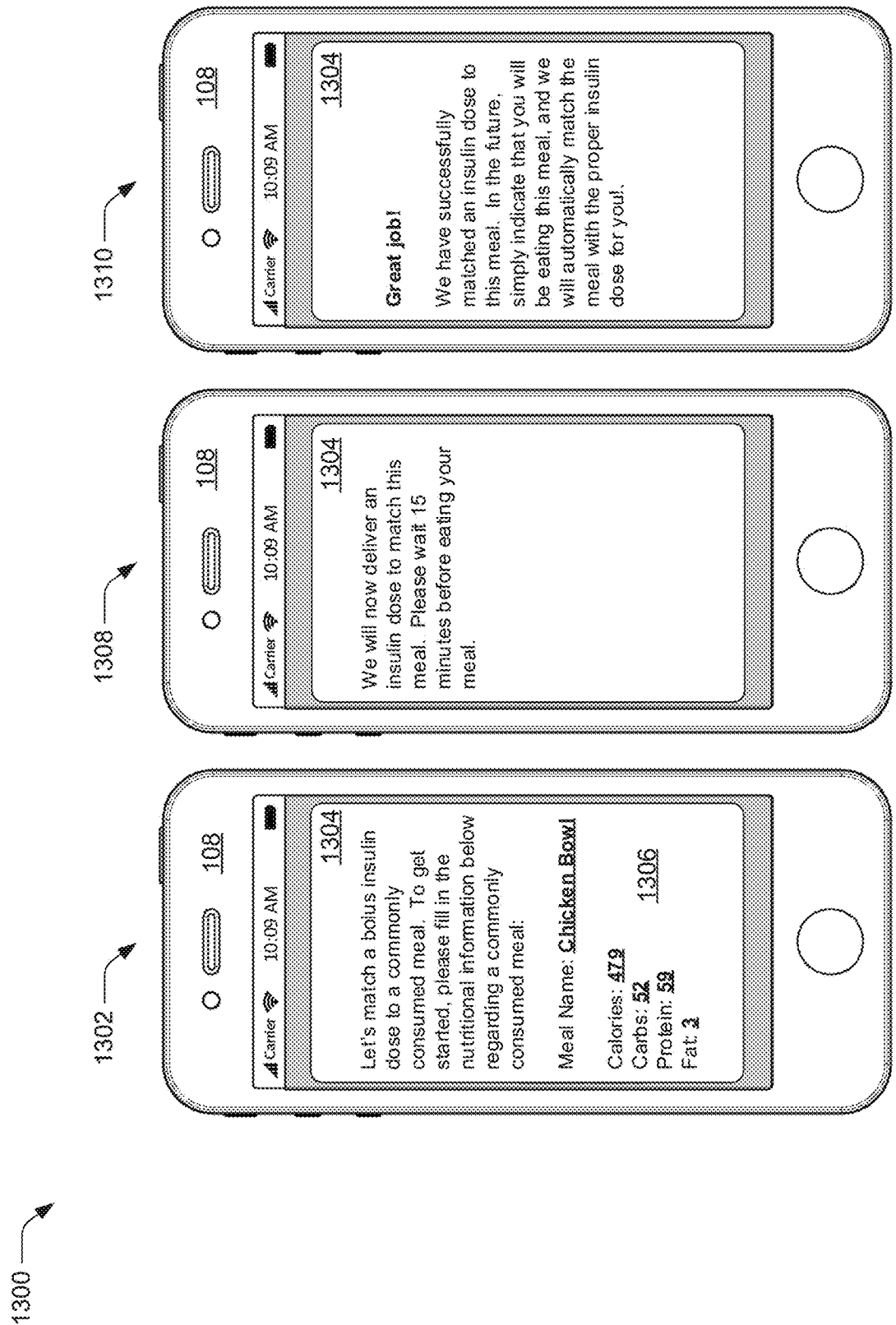
FIG. 13 depicts an example implementation of user interfaces displayed for matching an insulin dose to a meal.

In the context of matching insulin doses to commonly consumed meals, consider FIG. 13 which depicts an example 1300 of user interfaces displayed by the artificial pancreas controller as part of the process to match an insulin dose to a meal. At 1302, the artificial pancreas controller 404 causes display of a user interface 1304 by the computing device 108. The user interface 1304 includes a prompt 1306 to receive user input describing nutritional information for a commonly consumed meal. In this example, person 102 has determined nutritional information for a commonly consumed meal that includes 8 ounces of chicken breast, 1 cup of white rice, and 100 grams of broccoli. The person 102 provides input via the prompt 1306 describing the meal name as "Chicken Bowl", along with nutritional information for the meal which in this case indicates that the meal contains 479 calories, 52 grams of carbohydrates, 59 grams of protein, and 3 grams of fat. This nutritional information may be determined by person 102 in a variety of different ways, such as by utilizing an online nutritional calculator. However, as discussed throughout, the nutritional information may be determined in a variety of different ways without departing from the spirit or scope of the described techniques.

At 1308, the artificial pancreas controller 404 controls the user interface 1304 to indicate that a bolus insulin dose has been delivered and instructs person 102 to wait for 15 minutes before beginning consumption of the meal. At 1310, the artificial pancreas controller 404 controls the user interface 1304 to display an indication that the determined bolus insulin dose has been matched to the meal. Providing this feedback may increase user confidence that the artificial pancreas controller 404 is effectively controlling the blood glucose levels of person 102, which is likely to incentivize users to continue to provide meal information to the system.

In one or more implementations, the artificial pancreas controller 404 can automatically set various attributes for a new user, such as a temporary basal rate to titrate insulin, the carbohydrate-to-glucose ratio, the insulin sensitivity factor, and so forth. In other words, rather than requiring user input or a protocol to determines these attributes, the artificial pancreas controller 404 may automatically configure these values for the person 102. Then, based on the glucose measurements received from the wearable glucose monitoring device 104 worn by the person 102, the artificial pancreas controller 404 can adjust these attributes over time so that the attributes are customized to person 102. Additionally, the artificial pancreas controller 404 can surface data to the person 102, as well as other users such as the healthcare provider of person 102, which shows how changes to these various attribute affect glucose control for person 102. For example, if the artificial pancreas algorithm 416 lowers the basal rate for a patient from 0.8 U/hr to 0.7 U/hr from 3 pm to 5 pm, the artificial pancreas controller 404 may log this change as an event along with data and analysis that supports this change. Such data and analysis may include, for example, an identification of the basal change in a graph of data, along with an overlay showing previous weeks of glucose data with the time period following the basal change.

As described throughout, the various attributes learned by the artificial pancreas controller 404 using the automated processes described above can be maintained in the shared storage 410. Subsequently, these attributes can be accessed by the artificial pancreas algorithm 416 from the shared storage 410 and utilized to control insulin doses delivered to person 102 by the insulin delivery system 106. As the insulin doses are delivered to person 102, the artificial pancreas controller 404 continuously monitors the blood glucose measurements provided by the wearable glucose monitoring device 104 worn by person 102. Based on the blood glucose measurements, the artificial pancreas controller 404 may automatically adjust the various attributes stored in the shared storage 410 to account for situations in which the blood glucose levels are not maintained within the target range.

The artificial pancreas controller 404 may adjust insulin doses in response to detecting that the blood glucose levels of person 102 are below the target glucose range (e.g., hypoglycemic) or above the target glucose range (e.g., hyperglycemic). Out of range blood glucose levels may be detected by the artificial pancreas controller 404 after the active time of a delivered bolus insulin dose as well as within the active time of a delivered bolus insulin dose. When blood glucose levels outside of the target range are detected, the artificial pancreas controller 404 may take various actions to adjust the insulin doses delivered to person 102 by insulin delivery system 106.

The artificial pancreas controller 404 detects a hypoglycemic blood glucose measurement that is below the target range after the active time of a bolus insulin dose when blood glucose measurements provided by the wearable glucose monitoring device 104 worn by person 102 indicate that the person's blood glucose level is within the target range immediately after the bolus insulin dose has completed its course, but then falls below the target range when the bolus insulin dose is no longer active. When the hypoglycemic blood glucose level is detected, the artificial pancreas controller 404 determines the likely cause of the low blood glucose level, such as high basal insulin dose, exercise, and/or alcohol consumption. The artificial pancreas controller 404 can determine the likely cause of the low glucose level by analyzing the data stored in the shared storage 410, as well as various additional data associated with the person 102. Such additional data, for example, may include activity data (e.g., heart rate data or steps data automatically collected by various wearable devices worn by the user), as well as user provided data (e.g., data input by the user via various user interfaces provided by the artificial pancreas controller 404 or other services).

As an example, by processing the data stored in the shared storage 410 as well as the various additional data, the artificial pancreas controller 404 can determine that a high basal insulin dose is the likely cause for the low glucose levels when low blood glucose levels are detected multiple times after the active time of the bolus insulin dose. Similarly, exercise can be identified as the cause of the low blood glucose level based on a determination that the low blood glucose level occurs regularly on days in which the person 102 exercises. In some cases, the artificial pancreas controller 404 may perform additional pattern analysis, such as by determining that exercise on certain days is combined with additional walking while person 102 is at work. Similarly, alcohol can be identified as the cause of the low blood glucose levels based on correlated alcohol consumption with the low blood glucose levels. In cases where the artificial pancreas controller 404 is unable to determine the likely cause of the out of range reading based on the available data, the artificial pancreas controller 404 may prompt the user to answer various questions, such as questions related to exercise, alcohol consumption, sickness, stress, and so forth.

Once the cause for the low blood glucose level is determined, the artificial pancreas controller 404 may automatically adjust the insulin doses delivered to the person 102, such as by modifying the attributes describing the basal or bolus insulin doses in the shared storage 410. Generally, the insulin doses are adjusted by the artificial pancreas controller 404 when a pattern for the low blood glucose levels can be determined within an error threshold. In contrast, the artificial pancreas controller 404 can handle "one time" low blood glucose levels by providing a low blood glucose alert to person 102.

The artificial pancreas controller 404 detects a hypoglycemic blood glucose measurement that is below the target range during the active time of a bolus insulin dose when blood glucose measurements provided by the wearable glucose monitoring device 104 worn by person 102 indicate that the person's blood glucose level is below the target range while the bolus insulin dose is active. When the hypoglycemic blood glucose level is detected during the active time of the bolus insulin dose, the artificial pancreas controller 404 determines the likely cause of the low blood glucose level. The artificial pancreas controller 404 can determine the likely cause of the low glucose level by analyzing the data stored in the shared storage 410, as well as various additional data associated with the person 102. Such additional data, for example, may include activity data (e.g., heart rate data or steps data automatically collected by various wearable devices worn by the user), as well as user provided data (e.g., data input by the user via various user interfaces provided by the artificial pancreas controller 404 or other services).

In some cases, the artificial pancreas controller 404 may determine a mismatch between the carbohydrates of the meal and the bolus insulin dose. Another possibility is that the bolus insulin dose is acting before the meal causes the glucose level to rise. This may be due to consumption of a carbohydrates with a low glycemic index which causes the carbohydrates to be more slowly digested by person 102, or due to delayed consumption of the meal by person 102. Other possible causes include a mismatch between the exercise factor used in computation of the bolus insulin dose and the actual exercise completed by person 102.

Once the cause for the low blood glucose level is determined, the artificial pancreas controller 404 may automatically adjust the insulin doses delivered to the person 102, such as by modifying the attributes describing the basal or bolus insulin doses in the shared storage 410. Generally, the insulin doses are adjusted when a pattern for the low blood glucose levels can be determined. For example, if a low glucose level is measured multiple times for a specific meal, the artificial pancreas controller 404 may adjust the bolus insulin dose for the specific meal by decreasing the dose. In contrast, one time low blood glucose levels can be handled by providing a low blood glucose alert to person 102 as described throughout.

The artificial pancreas controller 404 detects a hyperglycemic blood glucose measurement that is above the target range after the active time of a bolus insulin dose when blood glucose measurements provided by the wearable glucose monitoring device 104 worn by person 102 indicate that the person's blood glucose level is within or below the target range immediately after the bolus insulin dose has completed its course, but then rises above the target range when the bolus insulin dose is no longer active. When the hyperglycemic blood glucose level is detected, the artificial pancreas controller 404 determines the likely cause of the high blood glucose level, such as an insufficient basal insulin dose, various health issues or illness, stress, lack of exercise, consumption of a meal that is high in fat, Gastroparesis, the dawn phenomenon, or the Simogyi effect, to name just a few.

Once the cause for the high blood glucose level is determined, the artificial pancreas controller 404 may automatically adjust the insulin doses delivered to the user, such as by modifying the attributes describing the basal or bolus insulin doses in the shared storage 410. Generally, the insulin doses are adjusted when a pattern for the high blood glucose levels can be determined. For example, if a high glucose level is measured multiple times for a specific meal, the artificial pancreas controller 404 may adjust the bolus insulin dose for the specific meal by increasing the dose. With regards to exercise, the basal insulin dose may have been determined assuming a certain amount and intensity of exercise by person 102. Subsequently, if the person's amount or intensity of exercise decreases, then the basal insulin dose may need to be increased to account for the higher blood glucose levels caused by the decrease in exercise by person 102. In contrast, one time high blood glucose levels can be handled by providing a high blood glucose alert to person 102 as described throughout. In cases where the artificial pancreas controller 404 is unable to determine the likely cause of the out of range reading based on the available data, the artificial pancreas controller may prompt the user to answer various questions, such as questions related to exercise, alcohol consumption, sickness, stress, and so forth.

The artificial pancreas controller 404 detects a hyperglycemic blood glucose measurement that is above the target range during the active time of a bolus insulin dose when blood glucose measurements provided by the wearable glucose monitoring device 104 worn by person 102 indicate that the person's blood glucose level is above the target range while the bolus insulin dose is active. When the hyperglycemic blood glucose level is detected during the active time of the bolus insulin dose, the artificial pancreas controller 404 determines the likely cause of the high blood glucose level. The artificial pancreas controller 404 can determine the likely cause of the high glucose level by analyzing the data stored in the shared storage 410, as well as various additional data associated with the person 102. Such additional data, for example, may include activity data (e.g., heart rate data or steps data automatically collected by various wearable devices worn by the user), as well as user provided data (e.g., data input by the user via various user interfaces provided by the artificial pancreas controller 404 or other services).

In some cases, the artificial pancreas controller 404 may determine a mismatch between the carbohydrates of the meal and the bolus insulin dose, in which case the bolus insulin dose for the meal is increased. Another possibility is that the bolus insulin dose is acting too late (e.g., the person's blood glucose levels rise before the insulin starts to act). Once the cause for the high blood glucose level is determined, the artificial pancreas controller 404 may automatically adjust the insulin doses delivered to the user, such as by modifying the attributes describing the basal or bolus insulin doses in the shared storage 410. Generally, the insulin doses are adjusted when a pattern for the high blood glucose levels can be determined. For example, if a high glucose level is measured multiple times for a specific meal, the artificial pancreas controller 404 may adjust the bolus insulin dose for the specific meal by increasing the dose. In contrast, one time high blood glucose levels can be handled by providing a high blood glucose alert to person 102 as described throughout.

Escalating Alerts

As noted above, the artificial pancreas controller 404 may be configured to cause output of escalating alerts using the different devices of the artificial pancreas system 402 (and potentially other remote devices), e.g., to decrease the occurrence of damaging health events due to hyper- and/or hypo-glycemia. One implementation example for providing such alerts is described in the following discussion.

The artificial pancreas controller 404 may provide an alert notification service using the wireless connections 412, 414 (e.g., Bluetooth) and by leveraging functionality of the wearable glucose monitoring device 104, the insulin delivery system 106, and/or the computing device 108. By way of example, the artificial pancreas controller 404 may receive an alert that originates at the insulin delivery system 106 (e.g., due to a measured level of insulin or device malfunction) over the wireless connection 414 and then cause the computing device 108 to output an indication of the alert. In this scenario, the insulin delivery system 106 may output a first indication of the alert (e.g., responsive to detecting a condition causing the alert) and the computing device 108 may output a second indication of the alert based on receipt of the alert by the artificial pancreas controller 404 and instructions from the controller to output the second indication. The artificial pancreas controller 404 is configured to manage alert escalation—so that it is managed at a single device. Management of this alert escalation may include determining where alerts are output (which devices), types of alerts output (e.g., tactile (vibrations), audible, visual (notifications)), and an order of output. This management also includes causing the alerts to be output according to the determination.

One or more of the wearable glucose monitoring device 104, the insulin delivery system 106, and/or the computing device 108 may also include functionality for a user (e.g., the person 102, his or her parent, or a health care provider) to acknowledge these alerts. As used herein, the term "acknowledging" may refer to providing user input in a manner that indicates the user has seen or otherwise sensed (e.g., felt a vibration) an alert and also indicates that the user is aware of possible effects which may be related to the alert, e.g., that hypo- or hyper-glycemia may soon occur if no intervening actions are performed. By way of example, these alerts can be acknowledged by pushing a physical button, providing some input in relation to a displayed user interface element (e.g., slide, press, double tap, and so forth), and/or providing a verbal acknowledgement, to name just a few. Such acknowledgement may "clear" the alert from all devices that are used to implement the alert notification service, such that if acknowledgment of the alert is received by the computing device 108, then the alert may also be cleared from the insulin delivery system 106 where the alert originated.

In one or more implementations, the artificial pancreas controller 404 may activate an application of the computing device 108, even if that application is not running at the time the alert is triggered. Examples of the application may include a glucose monitoring application or an insulin application, which may correspond to the glucose monitoring module 408 and/or the insulin module 406 (or various portions thereof). In scenarios where an alert is associated with a message in text, the text of the alert may be maintained on a master device (e.g., the device detecting the condition that caused the alert) such that other devices used to implement the service need not be exposed to the text (or translations of the text) in advance of the alert.

In accordance with the described techniques, consider the following alert escalation example. The artificial pancreas controller 404 causes the computing device 108 to vibrate responsive to detection of a condition associated with an alert. If no acknowledgement is received within an amount of time, then the artificial pancreas controller 404 causes the insulin delivery system 106 to vibrate. If no acknowledgement is received within an amount of time, then the artificial pancreas controller 404 causes the computing device 108 to output an alert sound via one or more speakers associated with the computing device 108. If no acknowledgement is received within an amount of time, then the artificial pancreas controller 404 causes the insulin delivery system 106 to output an alert sound via one or more speakers associated with the insulin delivery system 106. This process may continue by subsequently alternating audible output by the computing device 108 and the insulin delivery system 106 until acknowledgement is received. It is to be appreciated that the amount of time between outputs may be the same or may be different between the different outputs, e.g., the time between outputs may decrease. Additionally, the artificial pancreas controller 404 may increase a volume of the audible output as the process continues. The artificial pancreas controller 404 may escalate alerts among devices that are part of the artificial pancreas system 402 in a variety of ways without departing from the spirit or scope of the techniques described herein.

Onboard Artificial Pancreas Algorithm Implementation Example

As mentioned above, the artificial pancreas algorithm 416 may be implemented at the wearable glucose monitoring device 104, in one or more implementations. Thus, rather than being implemented at the computing device 108, as depicted in FIG. 4, the artificial pancreas algorithm 416 and the pump control module 418 may be implemented at or otherwise local to the wearable glucose monitoring device 104—the artificial pancreas algorithm 416 and the pump control module 418 may be included in computer-readable media of the wearable glucose monitoring device 104 and they may be run using one or more processors of the wearable glucose monitoring device 104. In this way, the artificial pancreas system 402 may operate using only the wearable glucose monitoring device 104 and the insulin delivery system 106 over at least one period of time, without interacting with the computing device 108 or another computing device. This may be advantageous in a variety of scenarios in which connecting to a computing device 108, or setting up a computing device to operate with the artificial pancreas algorithm 416 and the pump control module 418, is undesirable, such as when the artificial pancreas system 402 is utilized in a hospital setting, in scenarios where a user does not have easy access to power or the network 116 (e.g., camping, hiking, in rural areas, while driving, etc.), and so forth.

In such scenarios, the artificial pancreas algorithm 416 may, at the wearable glucose monitoring device 104, determine doses of insulin to be delivered to the person 102 based on the glucose measurements 118 produced by the wearable glucose monitoring device 104. The pump control module 418 may then generate instructions at the wearable glucose monitoring device 104 that instruct the insulin delivery system 106 to deliver the determined amount of insulin to the person 102 at one or more times. A transmitter of the wearable glucose monitoring device 104 may then transmit the instructions to the insulin delivery system 106 over a communicable coupling, such as over a Bluetooth Low Energy (BLE) link, near field communication (NFC) connection, or 5G, to name just a few.

At one or more intervals, the artificial pancreas algorithm 416 and/or the pump control module 418 may back up any settings that changed since a last update, such as by establishing a communicative coupling with the computing device 108 and communicating the settings to the computing device 108. The communicated settings can then be saved by the computing device 108, e.g., by persisting the settings locally on computer-readable media of the computing device 108 or the settings can be communicated to the glucose monitoring platform 112 for storage in the storage device 120. In this way, the person 102's settings may not simply be discarded when the wearable glucose monitoring device 104 expires, e.g., when it is time to replace the wearable glucose monitoring device 104 with a new one.

Examples of the interval at which the settings may be communicated to the computing device include every 7 days, every 10 days, every 14 days, and at expiration of the wearable glucose monitoring device 104, to name just a few. When a new wearable glucose monitoring device 104 is applied to the person, the saved settings may then be communicated from the computing device 108 to the new wearable glucose monitoring device 104, such that the artificial pancreas algorithm 416 and the pump control module 418 can be used from the persisted state. In this way, any learning or optimizing of the artificial pancreas algorithm 416 and/or the pump control module 418 may be maintained over time and over the use of multiple wearable glucose monitoring devices. Alternatively or in addition, the settings may be backed up at the insulin delivery system 106.

In one or more implementations, the artificial pancreas algorithm 416 and the pump control module 418 may operate in different modes from the wearable glucose monitoring device 104, including, by way of example and not limitation, a predictive low glucose suspend only mode, or a partially closed loop mode (e.g., where the person 102 delivers bolus insulin doses for meals), to name just a few.

Example Procedures

This section describes example procedures for machine learning in an artificial pancreas. Aspects of the procedures may be implemented in hardware, firmware, or software, or a combination thereof. The procedures are shown as a set of blocks that specify operations performed by one or more devices and are not necessarily limited to the orders shown for performing the operations by the respective blocks. In at least some implementations the procedures are performed by an artificial pancreas controller, such as artificial pancreas controller 404 that makes use of an insulin module 406 and a glucose monitoring module 408.

Figure 14:
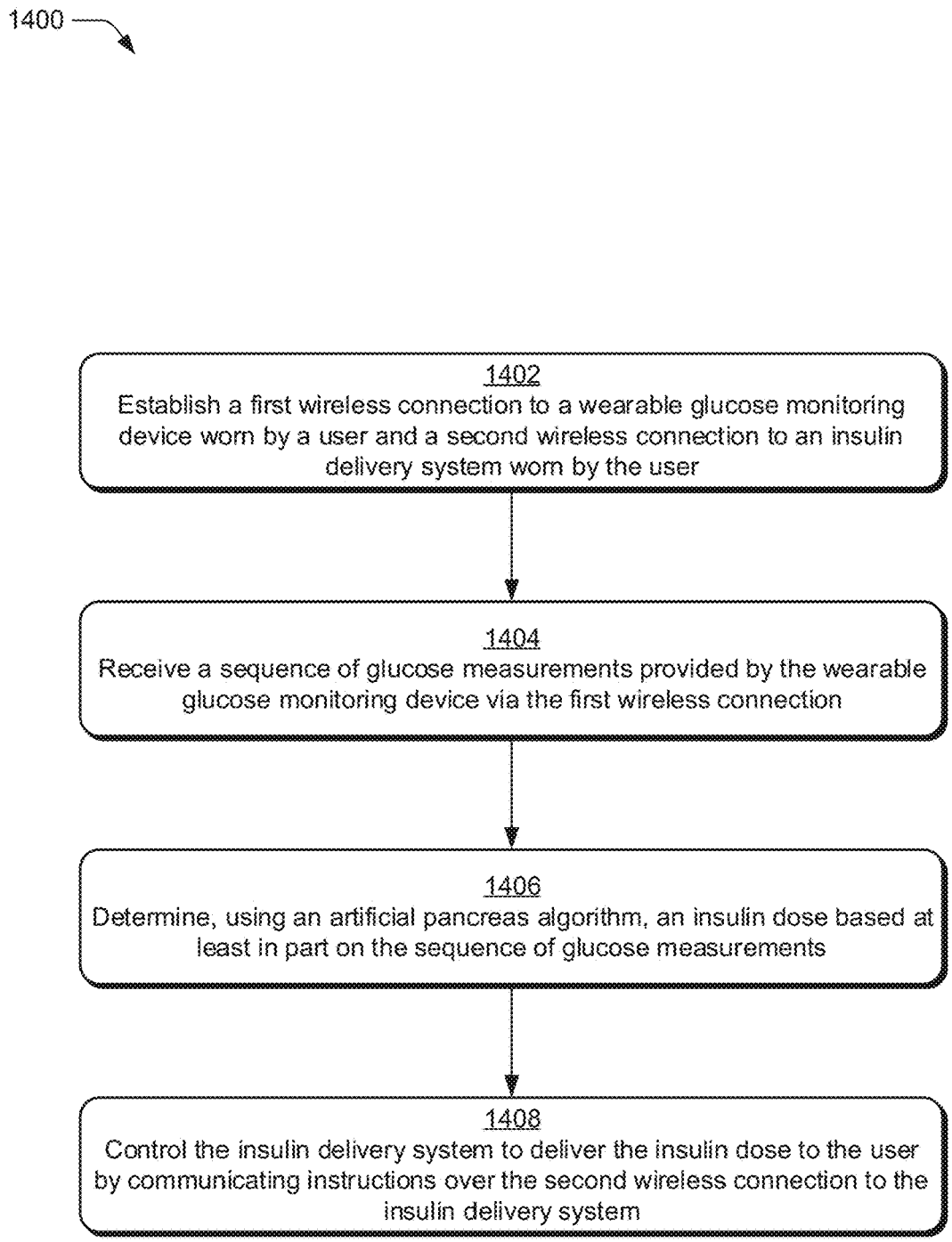
FIG. 14 depicts a procedure in an example implementation in which an insulin dose is determined and delivered to a user.

FIG. 14 depicts an example procedure 1400 in which an insulin dose is determined and delivered to a user.

A first wireless connection to a wearable glucose monitoring device worn by a user is established, and a second wireless connection to an insulin delivery system worn by the user is established (block 1402). By way of example, an artificial pancreas controller 404 implemented at computing device 108 establishes a first wireless connection 412 to a wearable glucose monitoring device 104 worn by person 102 and second wireless connection 414 to insulin delivery system 106.

A sequence of glucose measurements provided by the wearable glucose monitoring device is received via the first wireless connection (block 1404). By way of example, the wearable glucose monitoring device 104 is configured to monitor glucose of the person 102 continuously. The wearable glucose monitoring device 104 may be configured with a glucose sensor, for instance, that continuously detects analytes indicative of the person 102's glucose and enables generation of glucose measurements 118. The artificial pancreas controller 404 implemented at computing device 108 receives the glucose measurements 118 from the wearable glucose monitoring device 104. The wearable glucose monitoring device 104 may communicate these measurements in real-time, e.g., as they are produced using a glucose sensor. Alternately or in addition, the wearable glucose monitoring device 104 may communicate the glucose measurements 118 to the computing device 108 at set time intervals, e.g., every 30 seconds, every minute, every 5 minutes, every hour, every 6 hours, every day, and so forth.

An insulin dose is determined using an artificial pancreas algorithm based at least in part on the sequence of glucose measurements (block 1406). By way of example, an artificial pancreas algorithm 416, of the artificial pancreas controller 404, determines an insulin dose based at least in part on the sequence of glucose measurements. The artificial pancreas algorithm 416 determines the inulin dose to prevent the person 102's glucose measurements 118 from departing a target range. Generally, extreme or sustained departures from such a target range can result in dangerous health conditions and/or damage to a person's body, e.g., heart, blood vessels, eyes, kidneys, and nerves. Maintaining glucose levels within the target range, through timely insulin delivery, can thus help avoid those dangerous health conditions and bodily damage. In some cases, the artificial pancreas algorithm 416 determines the insulin dose based at least in part on previous insulin doses delivered to the user by the insulin delivery system (e.g., basal or bolus doses), a trend of glucose measurements provided by the wearable glucose monitoring device 104, or data identifying one or more events corresponding to the user, such as food consumption, carbohydrate consumption, exercise, stress, or illness. In one or more implementations, the artificial pancreas algorithm 416 predicts that an event has occurred based on the sequence of glucose measurements and determines the insulin dose based at least in part on the predicted event (e.g., food consumption or exercise).

The insulin delivery system is controlled to deliver the insulin dose to the user by communicating instructions over the second wireless connection to the insulin delivery system (block 1408). By way of example, the pump control manager 418 of the artificial pancreas controller 404 may generate instructions, based on the artificial pancreas algorithm 416's output, that instruct the insulin delivery system 106 to deliver an amount of insulin over a time period, e.g., three insulin units (IU) immediately, 0.15 IU every hour continuously, and so forth. The pump control manager 418 may also cause these instructions to be communicated over the wireless connection 414 to the insulin delivery system 106.

Figure 15:
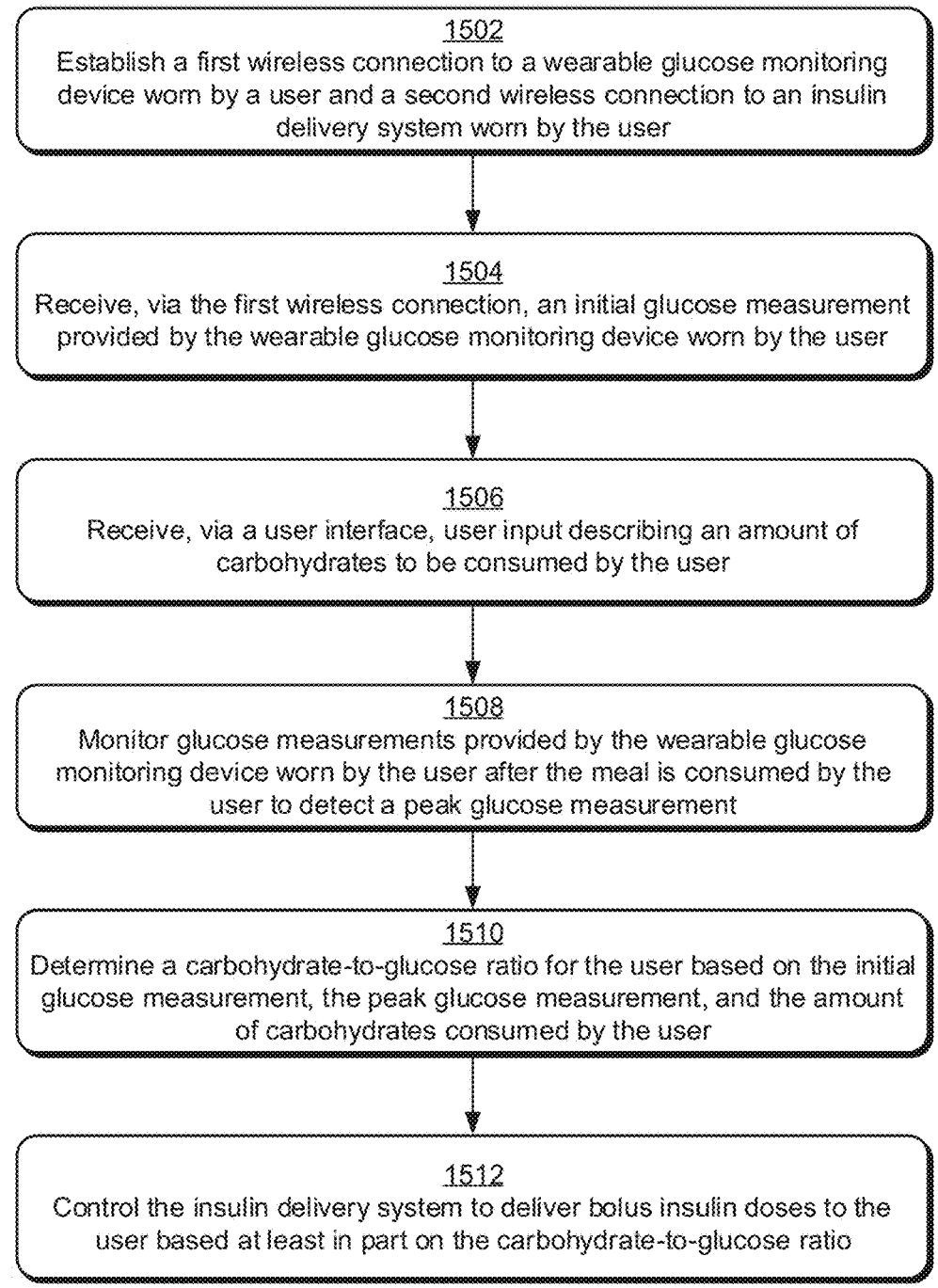
FIG. 15 depicts a procedure in an example implementation in which a carbohydrate-to-glucose ratio is determined and used to control delivery of bolus insulin doses.

FIG. 15 depicts an example procedure 1500 in which a carbohydrate-to-glucose ratio is determined and used to control delivery of bolus insulin doses.

A first wireless connection to a wearable glucose monitoring device worn by a user is established, and a second wireless connection to an insulin delivery system worn by the user is established (block 1502). By way of example, an artificial pancreas controller 404 implemented at computing device 108 establishes a first wireless connection 412 to a wearable glucose monitoring device 104 worn by person 102 and second wireless connection 414 to insulin delivery system 106.

An initial glucose measurement provided by the wearable glucose monitoring device worn by the user is received via the first wireless connection (block 1504) and user input describing an amount of carbohydrates to be consumed by the user is received via a user interface (block 1506). By way of example, the artificial pancreas controller 404 provides a protocol to determine optimal bolus insulin doses. Notably, carbohydrates and insulin affect people differently, and thus the artificial pancreas controller 404 is configured to determine the effect of carbohydrates and insulin on the blood glucose level of person 102 in order to accurately predict glucose levels and corresponding bolus doses of insulin to deliver to maintain the blood glucose level within the target range in response to various events, such as carbohydrate consumption, exercise, stress, or illness. As part of this, the artificial pancreas controller 404 employs a process to learn the carbohydrate-to-glucose ratio and insulin sensitivity factor for person 102.

Figure 11:
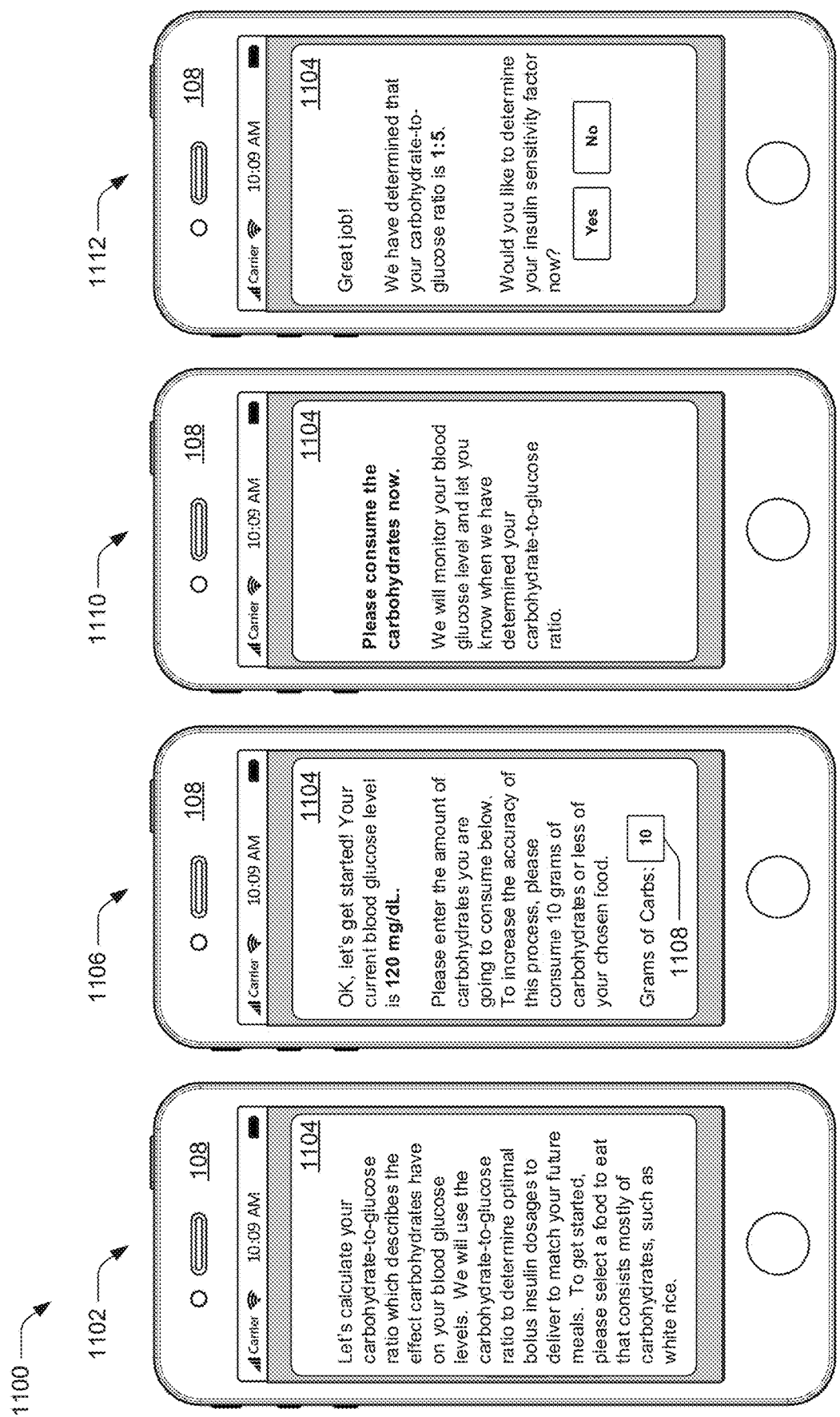
FIG. 11 depicts an example implementation of user interfaces displayed for determining a carbohydrate-to-glucose ratio for a person.

As part of the process to determine the carbohydrate-to-glucose ratio, the artificial pancreas controller 404 determines an initial glucose measurement based on the glucose measurements 118 provided by the wearable glucose monitoring device 104 worn by person 102, and obtains nutritional information describing an amount of carbohydrates to be consumed by person 102. For example, as depicted in FIG. 11, the artificial pancreas controller controls the user interface 1104 to display a second screen which indicates an initial blood glucose level of person 102 is 120 mg/dL, as well as a control 1108 configured to receive user input defining the amount of carbohydrates that person 102 will consume.

Glucose measurements provided by the wearable glucose monitoring device worn by the user are monitored after the meal is consumed by the user to detect a peak glucose measurement (block 1508). By way of example, after determining the initial blood glucose measurement and the nutritional information describing an amount of carbohydrates to be consumed, the artificial pancreas controller 404 monitors the blood glucose level based on the glucose measurements 118 provided by the wearable glucose monitoring device 104 worn by person 102. Notably, after consuming the carbohydrates, the blood glucose measurements will increase up to a peak glucose measurement, before decreasing back downwards. In order to determine the peak glucose measurement, the artificial pancreas controller 404 may monitor the trend rate of the user's glucose measurements 118 as they increase and detect the peak glucose measurement when the trend rate decreases towards a value of 0. This is because the decrease in the trend rate indicates that the peak glucose measurement, caused by the consumption of carbohydrates, has been reached.

A carbohydrate-to-glucose ratio for the user is determined based on the initial glucose measurement, the peak glucose measurement, and amount of carbohydrates consumed (block 1510). By way of example, the artificial pancreas controller 404 determines the carbohydrate-to-glucose ratio based on the initial glucose measurement, the peak glucose measurement, and the amount of carbohydrates consumed. For example, the carbohydrate-to-glucose ratio may be determined by dividing the number of carbohydrates (measured in grams) by the change in blood glucose measurements (e.g., the difference between the initial blood glucose measurement and the peak blood glucose measurement). In some cases, the results of the carbohydrate-to-glucose ratio is output by the artificial pancreas controller 404. In FIG. 11, for example, the artificial pancreas controller 404 controls the user interface 1104 to display the determined carbohydrate-to-glucose ratio.

The insulin delivery system is controlled to deliver bolus insulin doses to the user based at least in part on the carbohydrate-to-glucose ratio (block 1512). By way of example, the carbohydrate-to-glucose ratio is stored in the shared storage 410 by the artificial pancreas controller 404 and used by the artificial pancreas algorithm 416 to determine bolus insulin doses. The artificial pancreas controller 404 then controls the insulin delivery system 106 to deliver the determined bolus insulin doses to the user as described throughout.

Figure 16:
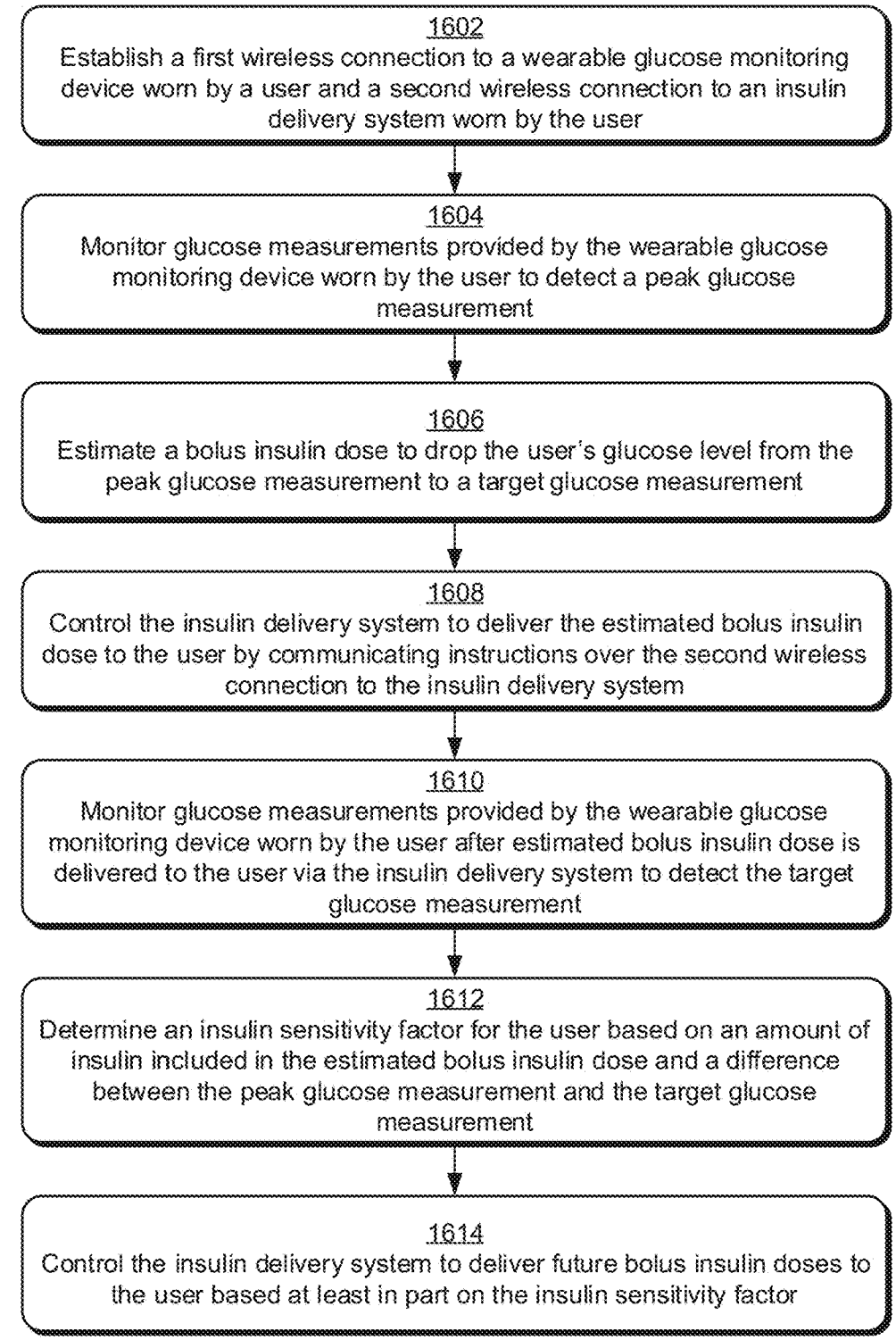
FIG. 16 depicts a procedure in an example implementation in which an insulin sensitivity factor is determined and used to control delivery of bolus insulin doses.

In one or more implementations, the artificial pancreas controller 404 can determine the insulin sensitivity factor after detecting the peak glucose level as part of the automated process. Alternately, the artificial pancreas controller 404 can determine the insulin sensitivity factor as part of a separate automated process. In the context of determining the insulin sensitivity factor, consider FIG. 16 which depicts an example procedure 1600 in which an insulin sensitivity factor is determined and used to control delivery of bolus insulin doses.

A first wireless connection to a wearable glucose monitoring device worn by a user is established, and a second wireless connection to an insulin delivery system worn by the user is established (block 1602). By way of example, an artificial pancreas controller 404 implemented at computing device 108 establishes a first wireless connection 412 to a wearable glucose monitoring device 104 worn by person 102 and second wireless connection 414 to insulin delivery system 106.

Glucose measurements provided by the wearable glucose monitoring device worn by the user are monitored to detect a peak glucose measurement (block 1604), and a bolus insulin dose to drop the user's glucose level from a peak glucose measurement to a target glucose measurement is estimated (block 1606). By way of example, the artificial pancreas controller 404 detects a peak glucose measurement, such as by detecting a leveling of the rate of increase of the glucose measurements 118 provided by the wearable glucose monitoring device 104 after carbohydrates are consumed by person 102 as part of the process to determine the carbohydrate-to-glucose ratio. Next, the artificial pancreas controller 404 estimates a bolus insulin dose that will drop the blood glucose level from the peak glucose measurement to the target glucose measurement. The artificial pancreas controller 404 may calculate a conservative estimate of the bolus insulin dose to prevent the blood glucose level from dropping too low into a hypoglycemic range. In some cases, the bolus insulin dose is estimated to cause the peak glucose measurement to drop to the target glucose measurement which corresponds to the initial glucose level of person 102. For example, if the initial blood glucose level of person 102 is 120 mg/dL and rises to a peak glucose level of 170 mg/DL, then the bolus insulin dose may be selected to return the blood glucose level to the initial level of 120 mg/dL.

The insulin delivery system is controlled to deliver the estimated bolus insulin dose to the user by communicating instructions over the second wireless connection to the insulin delivery system (block 1608). By way of example, the artificial pancreas controller 404 controls the insulin delivery system 106 to deliver the estimated bolus insulin dose to person 102 by communicating instructions over the second wireless connection to the insulin delivery system 106.

Glucose measurements provided by the wearable glucose monitoring device worn by the user are monitored after the estimated bolus insulin dose is delivered to the user via the insulin delivery system to detect the target glucose measurement (block 1610), and the insulin sensitivity factor for the user is determined based on an amount of insulin included in the estimated bolus insulin dose and a difference between the peak glucose measurement and the target glucose measurement (block 1612). By way of example, the artificial pancreas controller 404 controls the insulin delivery system 106 to deliver the estimated bolus insulin dose to person 102, and monitors the glucose measurements 118 provided by the wearable glucose monitoring device 104 worn by person 102—after the estimated bolus insulin dose is delivered to the person 102 via the insulin delivery system 106—to detect a target glucose measurement, corresponding to a leveling of the rate of decrease in the glucose measurements 118. The artificial pancreas controller 404 determines the insulin sensitivity factor based on an amount of insulin included in the estimated bolus insulin dose and the difference between the peak glucose measurement and the target glucose measurement. For example, the change in the blood glucose level (e.g., the difference between the peak glucose measurement and the target glucose measurement) may be divided by the units of insulin delivered in the estimated bolus insulin dose. In some cases, the artificial pancreas controller 404 may include other factors when calculating the insulin sensitivity factor, such as the amount of time before the insulin started to have an effect on the blood glucose level, when the effect of the insulin peaked, and when the effect of the insulin began to drop.

The insulin delivery system is controlled to deliver future bolus insulin doses to the user based at least in part on the insulin sensitivity factor (block 1614). By way of example, the insulin sensitivity factor is stored in the shared storage 410 by the artificial pancreas controller 404 and used by the artificial pancreas algorithm 416 to determine bolus insulin doses. The artificial pancreas controller 404 then controls the insulin delivery system 106 to deliver the determined bolus insulin doses to the user as described throughout.

Figure 17:
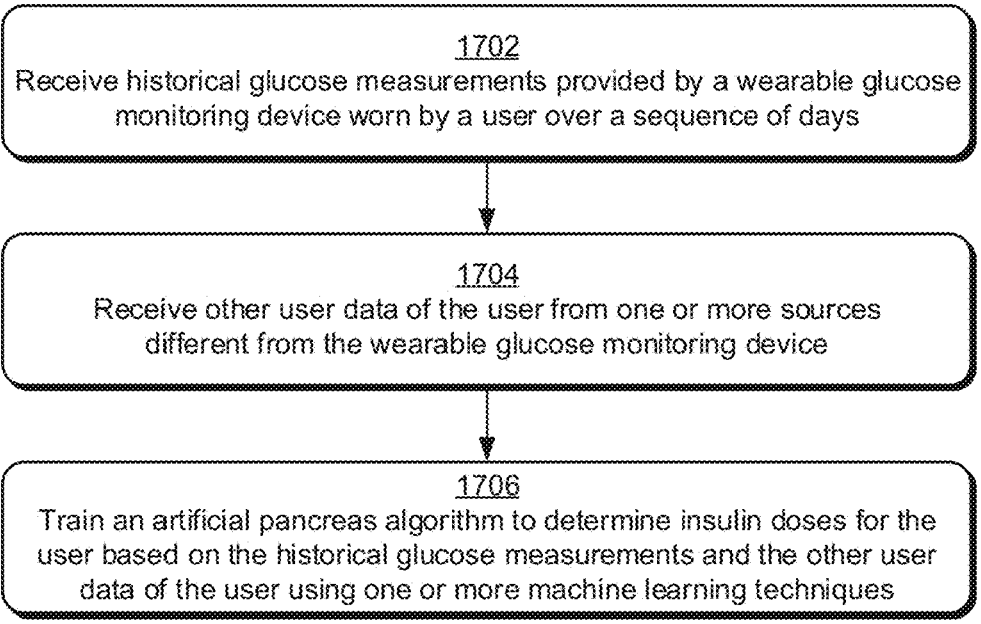
FIG. 17 depicts a procedure in an example implementation in which an artificial pancreas algorithm is trained to determine insulin doses for a user using one or more machine learning techniques.

FIG. 17 depicts an example procedure 1700 in which an artificial pancreas algorithm is trained to determine insulin doses for a user using one or more machine learning techniques.

Historical glucose measurements provided by a wearable glucose monitoring device worn by a user over a sequence of days are received (block 1702), and additional data of the user is received from one or more sources different from the wearable glucose monitoring device (block 1704). In accordance with the principles described herein, the other user data may include food consumption data, activity data, or insulin doses that are correlated to the glucose measurements, to name just a few.

An artificial pancreas algorithm is trained to determine insulin doses for the user based on the historical glucose measurements and the other user data of the user using one or more machine learning techniques (block 1706). By way of example, the artificial pancreas algorithm 416 and/or the models it comprises may be trained or otherwise learned initially using the glucose measurements 118 and other user data (e.g., delivered insulin doses, insulin measurements, target glucose ranges, insulin sensitivities, carb ratios, food consumption data, activity data, etc.) of the user population 110 maintained in the storage device 120. Further, this other user data may be correlated with the glucose measurements 118, for instance, based on timestamps of the glucose measurements and the other data. The initially trained artificial pancreas algorithm 416 may then be communicated over connection 420 (which may be wired, wireless, or a combination) for incorporation with the artificial pancreas controller 404. Once incorporated, the artificial pancreas algorithm 416 may be further trained so that it is customized for the person 102, i.e., the person associated with the computing device 108 and wearing the particular wearable glucose monitoring device 104 and the particular insulin delivery system 106.

For example, the artificial pancreas algorithm 416 may be further trained so that it is personalized for the person 102, in part, by obtaining target measurements, target measurement ranges, and/or starting doses from a health care provider of the person 102. Starting doses of insulin may be obtained for a basal titration process, for instance, and through the process adjusted as described in more detail below. Data for the basal titration process may be obtained from the health care provider (e.g., via a health care provider portal of the glucose monitoring platform 112) and/or via one or more user interfaces displayed via the computing device 108, e.g., in connection with setting up the artificial pancreas system 402 for use. In the latter scenario, the computing device 108 may receive input from a user (e.g., the person 102) via a series or sequence of these setup interfaces. The artificial pancreas algorithm 416 may also be further trained using similar data as is used from the user population 110, but that is obtained about the person 102, such as the person 102's historical glucose measurements 118, delivered insulin doses, insulin measurements, target glucose ranges, insulin sensitivities, carb ratios, food consumption data, activity data, and so on. Like the user population 110 the glucose measurements 118 of the person 102 may be correlated with the other data, such as based on timestamps of the glucose measurements 118 and the other data. Once trained, the artificial pancreas algorithm 416 is utilized to by the artificial pancreas controller 404 to determine insulin doses for the user, and deliver the insulin doses the user via the insulin delivery system 106.

FIG. 18 depicts an example procedure 1800 in which an insulin delivery request is encrypted and communicated for decryption by an application.

An encrypted message is generated by encrypting an insulin delivery request (block 1802). In accordance with the principles described herein, the insulin delivery request requests delivery of insulin by an insulin delivery system to a person wearing the insulin delivery system. By way of example, the glucose monitoring module 408 encrypts an insulin delivery request that requests delivery of insulin by the insulin delivery system 106 to the person 102. In this example, the glucose monitoring module 408 and at least the artificial pancreas algorithm 416 may be included as part of a first application. The glucose monitoring module 408 generates an encrypted message based on the encryption.

The encrypted message is communicated to an insulin application for decryption and for further communication of instructions, based on the insulin delivery request, to the insulin delivery system (block 1804). By way of example, the glucose monitoring module 408 communicates the encrypted message generated at block 1802 to the insulin module 406. Here, at least a portion of the insulin module 406—the pump control manager 418—may be included as part of a second application, e.g., corresponding to the insulin delivery system 106. The pump control manager 418 causes instructions to be communicated to the insulin delivery system 106 to deliver insulin to the person 102 in accordance with the instructions.

FIG. 19 depicts an example procedure 1900 in which an encrypted insulin delivery request is received, decrypted, and instructions for delivering insulin are communicated to an insulin delivery system based on the request.

An encrypted message comprising an insulin delivery request is received (block 1902). By way of example, the insulin module 406 receives an encrypted message comprising an insulin delivery request. The encrypted message is decrypted to reveal the insulin delivery request (block 1904). By way of example, the insulin module 406 decrypts the encrypted message received at block 1902 to reveal the insulin deliver request.

Instructions are communicated to an insulin delivery system over a wireless connection (block 1906). In accordance with the principles discussed herein, the instructions instruct the insulin delivery system to deliver insulin to a person wearing the insulin delivery system according to the insulin delivery request. By way of example, the pump control manager 418 communicates instructions to the insulin delivery system 106 over the wireless connection 414 to deliver insulin to the person 102 in accordance with the insulin delivery request revealed at block 1904.

Having described example procedures in accordance with one or more implementations, consider now an example system and device that can be utilized to implement the various techniques described herein.

Example System and Device

Figure 20:
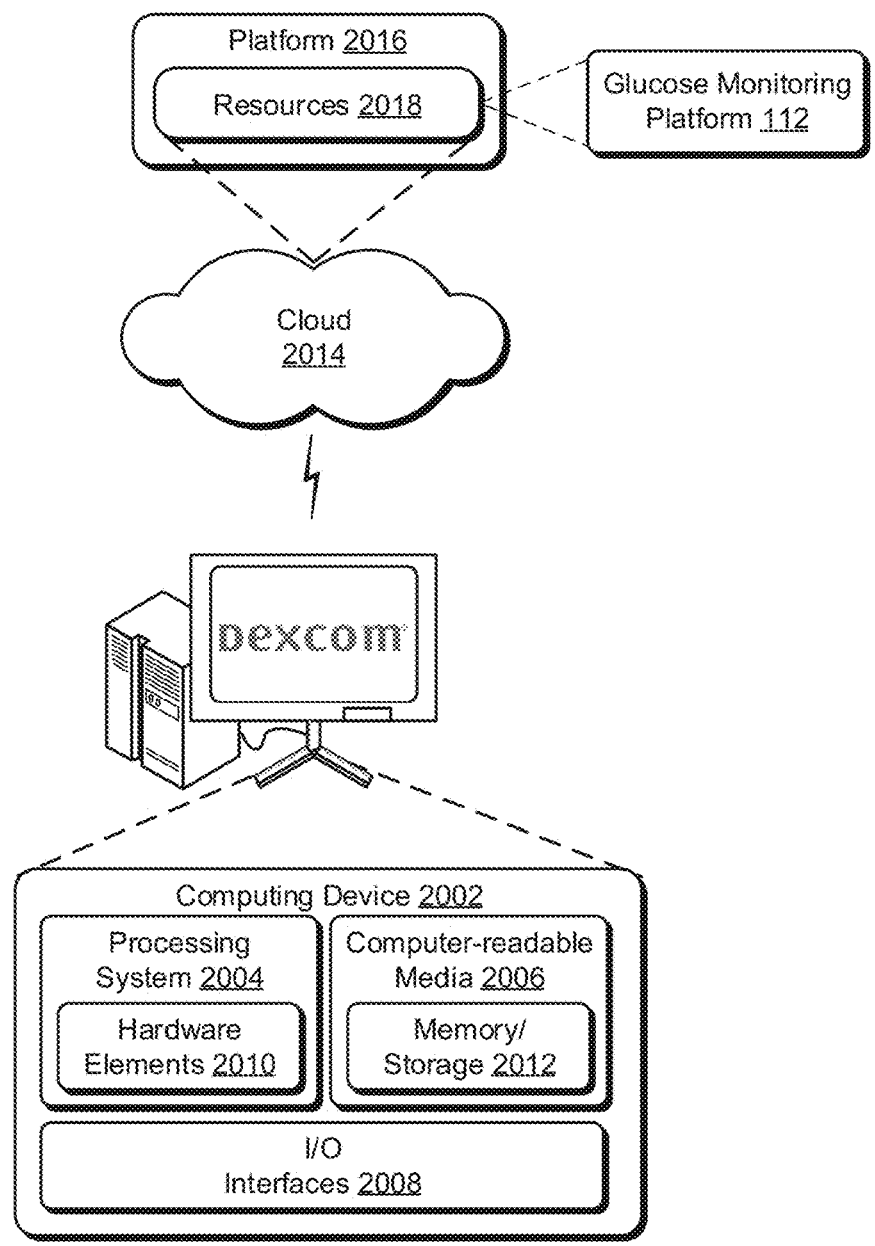
FIG. 20 illustrates an example system including various components of an example device that can be implemented as any type of computing device as described and/or utilized with reference to FIGS. 1-19 to implement embodiments of the techniques described herein.

FIG. 20 illustrates an example system generally at 2000 that includes an example computing device 2002 that is representative of one or more computing systems and/or devices that may implement the various techniques described herein. This is illustrated through inclusion of the glucose monitoring platform 112. The computing device 2002 may be, for example, a server of a service provider, a device associated with a client (e.g., a client device), an on-chip system, and/or any other suitable computing device or computing system.

The example computing device 2002 as illustrated includes a processing system 2004, one or more computer-readable media 2006, and one or more I/O interfaces 2008 that are communicatively coupled, one to another. Although not shown, the computing device 2002 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 2004 is representative of functionality to perform one or more operations using hardware. Accordingly, the processing system 2004 is illustrated as including hardware elements 2010 that may be configured as processors, functional blocks, and so forth. This may include implementation in hardware as an application specific integrated circuit or other logic device formed using one or more semiconductors. The hardware elements 2010 are not limited by the materials from which they are formed or the processing mechanisms employed therein. For example, processors may be comprised of semiconductor(s) and/or transistors (e.g., electronic integrated circuits (ICs)). In such a context, processor-executable instructions may be electronically-executable instructions.

The computer-readable media 2006 is illustrated as including memory/storage 2012. The memory/storage 2012 represents memory/storage capacity associated with one or more computer-readable media. The memory/storage component 2012 may include volatile media (such as random access memory (RAM)) and/or nonvolatile media (such as read only memory (ROM), Flash memory, optical disks, magnetic disks, and so forth). The memory/storage component 2012 may include fixed media (e.g., RAM, ROM, a fixed hard drive, and so on) as well as removable media (e.g., Flash memory, a removable hard drive, an optical disc, and so forth). The computer-readable media 2006 may be configured in a variety of other ways as further described below.

Input/output interface(s) 2008 are representative of functionality to allow a user to enter commands and information to computing device 2002, and also allow information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which may employ visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 2002 may be configured in a variety of ways as further described below to support user interaction.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. The features of the techniques described herein are platform-independent, meaning that the techniques may be implemented on a variety of commercial computing platforms having a variety of processors.

An implementation of the described modules and techniques may be stored on or transmitted across some form of computer-readable media. The computer-readable media may include a variety of media that may be accessed by the computing device 2002. By way of example, and not limitation, computer-readable media may include "computer-readable storage media" and "computer-readable signal media."

"Computer-readable storage media" may refer to media and/or devices that enable persistent and/or non-transitory storage of information in contrast to mere signal transmission, carrier waves, or signals per se. Thus, computer-readable storage media refers to non-signal bearing media. The computer-readable storage media includes hardware such as volatile and non-volatile, removable and non-removable media and/or storage devices implemented in a method or technology suitable for storage of information such as computer readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable signal media" may refer to a signal-bearing medium that is configured to transmit instructions to the hardware of the computing device 2002, such as via a network. Signal media typically may embody computer readable instructions, data structures, program modules, or other data in a modulated data signal, such as carrier waves, data signals, or other transport mechanism. Signal media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media.

As previously described, hardware elements 2010 and computer-readable media 2006 are representative of modules, programmable device logic and/or fixed device logic implemented in a hardware form that may be employed in some embodiments to implement at least some aspects of the techniques described herein, such as to perform one or more instructions. Hardware may include components of an integrated circuit or on-chip system, an application-specific integrated circuit (ASIC), a field-programmable gate array (FPGA), a complex programmable logic device (CPLD), and other implementations in silicon or other hardware. In this context, hardware may operate as a processing device that performs program tasks defined by instructions and/or logic embodied by the hardware as well as a hardware utilized to store instructions for execution, e.g., the computer-readable storage media described previously.

Combinations of the foregoing may also be employed to implement various techniques described herein. Accordingly, software, hardware, or executable modules may be implemented as one or more instructions and/or logic embodied on some form of computer-readable storage media and/or by one or more hardware elements 2010. The computing device 2002 may be configured to implement particular instructions and/or functions corresponding to the software and/or hardware modules. Accordingly, implementation of a module that is executable by the computing device 2002 as software may be achieved at least partially in hardware, e.g., through use of computer-readable storage media and/or hardware elements 2010 of the processing system 2004. The instructions and/or functions may be executable/operable by one or more articles of manufacture (for example, one or more computing devices 2002 and/or processing systems 2004) to implement techniques, modules, and examples described herein.

The techniques described herein may be supported by various configurations of the computing device 2002 and are not limited to the specific examples of the techniques described herein. This functionality may also be implemented all or in part through use of a distributed system, such as over a "cloud" 2014 via a platform 2016 as described below.

The cloud 2014 includes and/or is representative of a platform 2016 for resources 2018. The platform 2016 abstracts underlying functionality of hardware (e.g., servers) and software resources of the cloud 2014. The resources 2018 may include applications and/or data that can be utilized while computer processing is executed on servers that are remote from the computing device 2002. Resources 2018 can also include services provided over the Internet and/or through a subscriber network, such as a cellular or Wi-Fi network.

The platform 2016 may abstract resources and functions to connect the computing device 2002 with other computing devices. The platform 2016 may also serve to abstract scaling of resources to provide a corresponding level of scale to encountered demand for the resources 2018 that are implemented via the platform 2016. Accordingly, in an interconnected device embodiment, implementation of functionality described herein may be distributed throughout the system 2000. For example, the functionality may be implemented in part on the computing device 2002 as well as via the platform 2016 that abstracts the functionality of the cloud 2014.

CONCLUSION

Although the systems and techniques have been described in language specific to structural features and/or methodological acts, it is to be understood that the systems and techniques defined in the appended claims are not necessarily limited to the specific features or acts described. Rather, the specific features and acts are disclosed as example forms of implementing the claimed subject matter.

What is claimed is:

1. A method comprising:
receiving, by an insulin application of a computing device, an encrypted message comprising an insulin delivery request from a glucose monitoring application of the computing device;
decrypting, by the insulin application, the encrypted message to reveal the insulin delivery request; and
communicating instructions to an insulin delivery system over a wireless connection, the instructions instructing the insulin delivery system to deliver insulin to a person wearing the insulin delivery system according to the insulin delivery request.

2. The method as described in claim 1, wherein the insulin delivery request specifies an amount of the insulin to deliver to the person.

3. The method as described in claim 2, wherein the insulin delivery request specifies timing for delivering the amount of insulin to the person.

4. The method as described in claim 2, wherein the amount of insulin is determined based on processing a sequence of glucose measurements of the person using one or more machine learning models.

5. The method as described in claim 1, wherein the insulin application and the glucose monitoring application are separate applications on the computing device.

6. The method as described in claim 1, wherein the encrypted message is encrypted using a public key of the insulin application.

7. The method as described in claim 1, further comprising decrypting the encrypted message using a private key of the insulin application.

8. The method as described in claim 7, wherein the insulin application maintains the private key in a keychain.

9. A computing device comprising:
an insulin application of the computing device to:
receive an encrypted message comprising an insulin delivery request from a glucose monitoring application of the computing device;
decrypt the encrypted message to reveal the insulin delivery request; and
cause communication of instructions to an insulin delivery system over a wireless connection, the instructions instructing the insulin delivery system to deliver insulin to a person wearing the insulin delivery system according to the insulin delivery request.

10. The computing device as described in claim 9, wherein the insulin delivery request specifies an amount of the insulin to deliver to the person.

11. The computing device as described in claim 10, wherein the insulin delivery request specifies timing for delivering the amount of insulin to the person.

12. The computing device as described in claim 10, wherein the amount of insulin is determined based on processing a sequence of glucose measurements of the person using one or more machine learning models.

13. The computing device as described in claim 9, wherein the glucose monitoring application is a separate application of the computing device from the insulin application.

14. The computing device as described in claim 9, wherein the encrypted message is encrypted using a public key of the insulin application.

15. The computing device as described in claim 9, further comprising decrypting the encrypted message using a private key of the insulin application.

16. The computing device as described in claim 15, wherein the insulin application maintains the private key in a keychain.

17. One or more computer-readable storage media storing instructions that are executable by one or more processors to perform operations comprising:
- receiving, by an insulin application on a mobile device, an encrypted message comprising an insulin delivery request from a glucose monitoring application on the mobile device;
- decrypting, by the insulin application, the encrypted message to reveal the insulin delivery request; and
- communicating instructions to an insulin delivery system over a wireless connection, the instructions instructing the insulin delivery system to deliver insulin to a person wearing the insulin delivery system according to the insulin delivery request.

18. The one or more computer-readable storage media as described in claim 17, wherein the insulin delivery request specifies an amount of the insulin to deliver to the person.

19. The one or more computer-readable storage media as described in claim 18, wherein the insulin delivery request specifies timing for delivering the amount of insulin to the person.

20. The one or more computer-readable storage media as described in claim 18, wherein the amount of insulin is determined based on processing a sequence of glucose measurements of the person using one or more machine learning models.

21. The one or more computer-readable storage media as described in claim 17, wherein the glucose monitoring application is a separate application on the mobile device, and the glucose monitoring application and the insulin application are authorized to access shared storage to securely share data maintained in the shared storage.

22. The one or more computer-readable storage media as described in claim 17, wherein the encrypted message is encrypted using a public key of the insulin application.

23. The one or more computer-readable storage media as described in claim 17, further comprising decrypting the encrypted message using a private key of the insulin application.

24. The one or more computer-readable storage media as described in claim 23, wherein the insulin application maintains the private key in a keychain.

25. An apparatus comprising:
- a receiving means of an insulin application on a computing device for receiving an encrypted message comprising an insulin delivery request from a glucose monitoring device on the computing device;
- a decryption means of the insulin application for decrypting the encrypted message to reveal the insulin delivery request; and
- a communication means for communicating instructions to an insulin delivery system over a wireless connection, the instructions instructing the insulin delivery system to deliver insulin to a person wearing the insulin delivery system according to the insulin delivery request.

* * * * *